(12) United States Patent
Ascione et al.

(10) Patent No.: US 11,911,451 B2
(45) Date of Patent: Feb. 27, 2024

(54) COMPOSITION OF TUMOR-ASSOCIATED PROLIFERATIVE PEPTIDES AND RELATED ANTI-CANCER IMMUNOGEN FOR THE TREATMENT OF LUNG CANCERS AND OTHER CANCERS

(71) Applicant: ImmuLogix Ltd, Jersey City, NJ (US)

(72) Inventors: Richard Ascione, Jersey City, NJ (US); Shengmei Qi, Jersey City, NJ (US)

(73) Assignee: ImmuLogix Ltd, Jersey City, NJ (US)

( * ) Notice: Subject to any disclaimer, the term of this patent is extended or adjusted under 35 U.S.C. 154(b) by 44 days.

(21) Appl. No.: 16/640,988

(22) PCT Filed: Aug. 21, 2018

(86) PCT No.: PCT/IB2018/056313
§ 371 (c)(1),
(2) Date: Feb. 21, 2020

(87) PCT Pub. No.: WO2019/038671
PCT Pub. Date: Feb. 28, 2019

(65) Prior Publication Data
US 2021/0121546 A1    Apr. 29, 2021

Related U.S. Application Data

(60) Provisional application No. 62/548,493, filed on Aug. 22, 2017.

(51) Int. Cl.
*A61K 47/64* (2017.01)
*A61K 39/00* (2006.01)
*A61P 35/00* (2006.01)

(52) U.S. Cl.
CPC ...... *A61K 39/0011* (2013.01); *A61K 39/0016* (2013.01); *A61K 39/0018* (2013.01); *A61K 47/646* (2017.08); *A61P 35/00* (2018.01); *A61K 2039/6037* (2013.01)

(58) Field of Classification Search
None
See application file for complete search history.

(56) References Cited

FOREIGN PATENT DOCUMENTS

| EP | 0202642 A2 | 11/1986 |
| EP | 0811683 A1 | 12/1997 |
| WO | 2011/109106 A2 | 9/2011 |

OTHER PUBLICATIONS

International Search Report dated Feb. 8, 2019, from corresponding International Application No. PCT/ IB2018/056313.
Anonymous: "gastrin-releasing peptide isoform 1 preproprotein [Homo sapiens] NP_002082", Jun. 11, 2017, XP055530364.
Patel O et al.: "Gastrin-releasing peptide and cancer", BBA—Reviews on Cancer, Elsevier Science BV, Amsterdam, NL, vol. 1766, No. 1, Aug. 1, 2006, pp. 23-41, XP024964006.
Micheletti R et al.: "Identification of bombesin receptors on isolated muscle cells from human intestine", Regulatory Peptides, Elsevier Science BV, NL, vol. 21, No. 3-4, Jun. 1, 1988, pp. 219-226, XP023463140.
Guojun Wu et al.: "A novel vaccine targeting gastrin-releasing peptide: efficient inhibition of breast cancer growth in vivo", ENDOCRINE—Related Cancer, Bioscientifica LTD, GB, vol. 15, No. 1, Mar. 1, 2008, pp. 149-159, XP009151961.
Lu et al.: "Improved efficacy of DNA vaccination against prostate carcinoma by boosting with recombinant protein vaccine and by introduction of a novel adjuvant epitope", Vaccine, Elsevier, Amsterdam, NL, vol. 27, No. 39, Aug. 27, 2009, pp. 5411-5418, XP026614442.
Joseph Ischia et al.: "Gastrin-releasing peptide: Different forms, different functions", Biofactors., vol. 35, No. 1, Jan. 1, 2009, pp. 69-75, XP055391092.
Paola Moreno et al.: "Bombesin related peptides/receptors and their promising therapeutic roles in cancer imaging, targeting and treatment", Expert Opinion on Therapeutic Targets, vol. 20, No. 9, Mar. 28, 2016, pp. 1055-10-73, XP055529928.
Yamaguchi, K. Abe K, Kameya T, Adachi I, Taguchi S, Otsubo K, Yanaihara N. Production and molecular size heterogeneity of immunoreactive gastrin-releasing peptide in fetal and adult lungs and primary lung tumors. Cancer Res. 43 (1983) 3932-3939.
Rehfeld J F, Bardram L, and Hilsted L., Gastrin in Human Bronchogenic Carcinomas: Constant Expression but Variable Processing of Progastrin. Cancer Res. 1989 49, 2840-2843.
E. Rozengurt, Neuropeptides as growth factors for normal and cancerous cells, Trends Endocrinol. Metab. 13 (2002) 128-134.
Mattei J, Achcar R D, Cano C H, et al., Gastrin-Releasing Peptide Receptor Expression in Lung Cancer. Arch Pathol Lab Med vol. 138, Jan. 2014.
Mabry M, Nelkin B D, Falco J P, Barr L F, Baylin S B. Transitions between lung cancer phenotypes-implications for tumor progression. Cancer Cells. Feb. 1991; 3(2):53-8.
Moody T W. Peptide hormones and lung cancer. Panminerva Med. Mar. 2006; 48(1): 19-26.
Hanahan D, and Weinberg R A. The Hallmarks of Cancer: The Next Generation. Cell 2011 vol. 144, Issue 5:646-74.
J. Zhou, J. Chen, M. Mokotoff, E. D. Ball, Targeting gastrin-releasing peptide receptors for cancer treatment, Anti-cancer Drugs 15 (2004) 921-927.
J. C. Reubi, S. Wenger, J. Schmuckli-Maurer, J. C. Schaer, M. Gugger, Bombesin receptor subtypes in human cancers: detection with the universal radioligand (125)I-[D-TYR(6), beta-ALA(11), PHE(13), Nle (14)] bombesin(6-14), Clin. Cancer Res. 8 (2002) 1139-1146.

(Continued)

*Primary Examiner* — S. Devi
(74) *Attorney, Agent, or Firm* — Troutman Pepper Hamilton Sanders LLP

(57) ABSTRACT

The present invention relates to immunogens directed against lung cancer associated proliferative peptides and growth factors and its uses thereof in conjunction with chemotherapeutics in the early and advanced treatment of various malignant diseases, especially including lung cancers, both small cell lung carcinomas (SCLC), non-small cell lung (NSCLC) cancers and neuroendocrine-type cancers.

13 Claims, 8 Drawing Sheets
Specification includes a Sequence Listing.

(56) References Cited

OTHER PUBLICATIONS

Gonzalez N, Moody T W, Igarashi H, Ito T, Jensen R T. Bombesin-related peptides and their receptors: recent advances in their role in physiology and disease states. Curr Opin Endocrinol Diabetes Obes. Feb. 2008; 15 (1):58-64.

Cuttitta F, Carney D N, Mulshine J, et al. Bombesin-like peptides can function as autocrine growth factors in human small-cell lung cancer. Nature. 1985; 316(6031):823-826.

Moody T W, Pert C B, Gazdar A F, Carney D N, Minna J D. High levels of intracellular bombesin characterize human small-cell lung carcinoma. Science. 1981; 214(4526):1246.

Sunday M E, Choi N, Spindel E R, Chin W W, Mark E J. Gastrin-releasing peptide gene expression in small cell and large cell undifferentiated lung carcinomas. Hum Pathol. 1991; 22(10): 1030-1039.

Chaudhry A, Carrasquillo J A, Avis I L, Shuke N, Reynolds J C, Bartholomew R, Larson S M, Cuttitta F, Johnson B E, Mulshine J L. Phase I and imaging trial of a monoclonal antibody directed against gastrin-releasing peptide in patients with lung cancer. Clin Cancer Res. Nov. 1999; 5(11):3385-93.

Smith A M, Morris T, Justin T, Michaeli D, and Watson S A., Gastrimmune-induced antigastrin-17 antibodies inhibit acid secretion in a rat fistula model. Aliment Pharmacol Ther 2001; 15: 1981-1988.

Van Solinge W W, Odum L, and Rehfeld J F. Ovarian Cancers Express and Process Progastrin. Cancer Research 1993 53, 1823-1828.

Dalm S U, Verzijlbergen J F, and De Jong M. Receptor Targeted Nuclear Imaging of Breast Cancer. Int. J. Mol. Sci. 2017, 18(2), 260-77.

Yashi M, Muraishi O, Kobayashi Y, Tokue A, Nanjo H. Elevated serum progastrin-releasing peptide (31-98) in metastatic and androgen-independent prostate cancer patients. Prostate. May 1, 2002; 51(2):84-97.

Hampton, M. B.; Kettle, A. J.; Winterbourn, C. C. Inside the neutrophil phagosome: oxidants, myeloperoxidase and bacterial killing. Blood 92:3007-3017; 1998.

Ramos-Álvarez I, Moreno P, Mantey S A, Nakamura T, Nuche-Berenguer B, Moody T W, Coy D H, Jensen R T. Insights into bombesin receptors and ligands: Highlighting recent advances. Peptides. Oct. 2015; 72:128-44.

```
                          SEQUENCE LISTING

<160> NUMBER OF SEQ ID NOS: 75

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 1

Cys Pro Pro Pro Pro Ser Ser Gln Pro Lys Ala Leu Gly Asn Gln Gln
1               5                   10                  15

Pro Ser Trp Asp Ser Glu Asp Ser Ser Asn Phe Lys Asp
            20                  25

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
```

```
<223> OTHER INFORMATION: D-amino acid
<220> FEATURE:
<221> NAME/KEY: MOD_RES
<222> LOCATION: (4)..(4)
<223> OTHER INFORMATION: D-amino acid

<400> SEQUENCE: 2

Cys Pro Pro Pro Pro Ser Ser Gln Pro Lys Ala Leu Gly Asn Gln Gln
1               5                   10                  15

Pro Ser Trp Asp Ser Glu Asp Ser Ser Asn Phe Lys Asp
            20                  25

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid

<400> SEQUENCE: 3

Cys Pro Pro Pro Pro Ser Ser Gln Pro Lys Ala Leu Gly Asn Gln Gln
1               5                   10                  15

Pro Ser Trp Asp Ser Glu Asp Ser Ser Asn Phe Lys Asp
            20                  25

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid

<400> SEQUENCE: 4

Cys Pro Pro Pro Pro Ser Ser Gln Pro Lys Ala Leu Gly Asn Gln Gln
1               5                   10                  15

Pro Ser Trp Asp Ser Glu Asp Ser Ser Asn Phe Lys Asp
            20                  25

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: D-amino acid
<220> FEATURE:
<221> NAME/KEY: MOD_RES
<222> LOCATION: (28)..(28)
<223> OTHER INFORMATION: D-amino acid
<220> FEATURE:
<221> NAME/KEY: MOD_RES
<222> LOCATION: (29)..(29)
```

<223> OTHER INFORMATION: D-amino acid

<400> SEQUENCE: 5

Ser Ser Gln Pro Lys Ala Leu Gly Asn Gln Gln Pro Ser Trp Asp Ser
1               5                   10                  15

Glu Asp Ser Ser Asn Phe Lys Asp Ser Ser Pro Pro Pro Cys
            20                  25                  30

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: D-amino acid
<220> FEATURE:
<221> NAME/KEY: MOD_RES
<222> LOCATION: (27)..(27)
<223> OTHER INFORMATION: D-amino acid
<220> FEATURE:
<221> NAME/KEY: MOD_RES
<222> LOCATION: (28)..(28)
<223> OTHER INFORMATION: D-amino acid

<400> SEQUENCE: 6

Gln Pro Lys Ala Leu Gly Asn Gln Gln Pro Ser Trp Asp Ser Glu Asp
1               5                   10                  15

Ser Ser Asn Phe Lys Asp Ser Ser Pro Pro Pro Cys
            20                  25

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: D-amino acid
<220> FEATURE:
<221> NAME/KEY: MOD_RES
<222> LOCATION: (28)..(28)
<223> OTHER INFORMATION: D-amino acid

<400> SEQUENCE: 7

Gln Pro Lys Ala Leu Gly Asn Gln Gln Pro Ser Trp Asp Ser Glu Asp
1               5                   10                  15

Ser Ser Asn Phe Lys Asp Ser Ser Pro Pro Pro Cys
            20                  25

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: D-amino acid

<400> SEQUENCE: 8

Gln Pro Lys Ala Leu Gly Asn Gln Gln Pro Ser Trp Asp Ser Glu Asp
1               5                   10                  15

Ser Ser Asn Phe Lys Asp Ser Ser Pro Pro Pro Cys
            20                  25

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (20)..(20)
<223> OTHER INFORMATION: Methionine amide

<400> SEQUENCE: 9

Cys Pro Pro Pro Pro Ser Ser Tyr Pro Arg Gly Asn His Trp Ala Val
1               5                   10                  15

Gly His Leu Met
            20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (20)..(20)
<223> OTHER INFORMATION: Methionine amide

<400> SEQUENCE: 10

Cys Pro Pro Pro Pro Ser Ser Tyr Pro Arg Gly Asn His Trp Ala Val
1               5                   10                  15

Gly His Leu Met
            20

<210> SEQ ID NO 11
<211> LENGTH: 20

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (20)..(20)
<223> OTHER INFORMATION: Methionine amide

<400> SEQUENCE: 11

Cys Pro Pro Pro Pro Ser Ser Tyr Pro Arg Gly Asn His Trp Ala Val
1               5                   10                  15

Gly His Leu Met
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (20)..(20)
<223> OTHER INFORMATION: Methionine amide

<400> SEQUENCE: 12

Cys Pro Pro Pro Pro Ser Ser Tyr Pro Arg Gly Asn His Trp Ala Val
1               5                   10                  15

Gly His Leu Met
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (8)..(8)
<223> OTHER INFORMATION: L-nitrophenylalanine
```

```
<220> FEATURE:
<221> NAME/KEY: MOD_RES
<222> LOCATION: (20)..(20)
<223> OTHER INFORMATION: Methionine amide

<400> SEQUENCE: 13

Cys Pro Pro Pro Ser Ser Phe Pro Arg Gly Asn His Trp Ala Val
1               5                   10                  15

Gly His Leu Met
            20

<210> SEQ ID NO 14
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 14

Cys Pro Pro Pro Pro Ser Ser Gly Thr Val Leu Thr Lys Met Tyr Pro
1               5                   10                  15

Arg Gly Asn His Trp Ala Val Gly His Leu
            20                  25

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 15

Cys Pro Pro Pro Pro Ser Ser Ala Gly Gly Gly Thr Val Leu Thr Lys
1               5                   10                  15

Met Tyr Pro Arg Gly Asn His Trp Ala Val Gly His Leu
            20                  25
```

```
<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: L-hydroxyproline
<220> FEATURE:
<221> NAME/KEY: MOD_RES
<222> LOCATION: (3)..(3)
<223> OTHER INFORMATION: L-hydroxyproline
<220> FEATURE:
<221> NAME/KEY: MOD_RES
<222> LOCATION: (4)..(4)
<223> OTHER INFORMATION: L-hydroxyproline
<220> FEATURE:
<221> NAME/KEY: MOD_RES
<222> LOCATION: (5)..(5)
<223> OTHER INFORMATION: L-hydroxyproline

<400> SEQUENCE: 16

Cys Pro Pro Pro Pro Ser Ser Ala Gly Gly Gly Thr Val Leu Thr Lys
1               5                   10                  15

Met Tyr Pro Arg Gly Asn His Trp Ala Val Gly His Leu
            20                  25

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 17

Cys Pro Pro Pro Pro Ser Ser Val Pro Leu Pro Ala Gly Gly Gly Thr
1               5                   10                  15

Val Leu Thr Lys Met Tyr Pro Arg Gly Asn His
            20                  25

<210> SEQ ID NO 18
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
```

```
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (9)..(9)
<223> OTHER INFORMATION: L-nitrophenylalanine
<220> FEATURE:
<221> NAME/KEY: MOD_RES
<222> LOCATION: (16)..(16)
<223> OTHER INFORMATION: D-amino acid

<400> SEQUENCE: 18

Cys Pro Pro Pro Pro Ser Ser Ala Phe Gly Trp Met Asp Phe Gly Arg
1               5                   10                  15

Arg Ser Ala Glu Asp Glu Asn
            20

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (9)..(9)
<223> OTHER INFORMATION: L-nitrophenylalanine
<220> FEATURE:
<221> NAME/KEY: MOD_RES
<222> LOCATION: (16)..(16)
<223> OTHER INFORMATION: D-amino acid

<400> SEQUENCE: 19

Cys Pro Pro Pro Pro Ser Ser Ala Phe Gly Trp Met Asp Phe Gly Arg
1               5                   10                  15

Arg Ser Ala Glu Asp Glu Asn
            20

<210> SEQ ID NO 20
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
```

```
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: L-nitrophenylalanine

<400> SEQUENCE: 20

Cys Pro Pro Pro Pro Ser Ser Ala Phe Gly Trp Met Asp Phe Gly Arg
1               5                   10                  15

Arg Ser Ala Glu Asp Glu Asn
            20

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (9)..(9)
<223> OTHER INFORMATION: L-nitrophenylalanine
<220> FEATURE:
<221> NAME/KEY: MOD_RES
<222> LOCATION: (16)..(16)
<223> OTHER INFORMATION: D-amino acid

<400> SEQUENCE: 21

Cys Pro Pro Pro Pro Gly Thr Ala Phe Gly Trp Met Asp Phe Gly Arg
1               5                   10                  15

Arg Ser Ala Glu Asp Glu Asn
            20

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: L-hydroxyproline
<220> FEATURE:
<221> NAME/KEY: MOD_RES
<222> LOCATION: (3)..(3)
<223> OTHER INFORMATION: L-hydroxyproline
<220> FEATURE:
<221> NAME/KEY: MOD_RES
<222> LOCATION: (4)..(4)
<223> OTHER INFORMATION: L-hydroxyproline
<220> FEATURE:
<221> NAME/KEY: MOD_RES
<222> LOCATION: (5)..(5)
<223> OTHER INFORMATION: L-hydroxyproline
<220> FEATURE:
<221> NAME/KEY: MOD_RES
<222> LOCATION: (9)..(9)
<223> OTHER INFORMATION: L-nitrophenylalanine
<220> FEATURE:
<221> NAME/KEY: MOD_RES
<222> LOCATION: (16)..(16)
<223> OTHER INFORMATION: D-amino acid

<400> SEQUENCE: 22
```

Cys Pro Pro Pro Ser Ser Ala Phe Gly Trp Met Asp Phe Gly Arg
1               5                   10                  15

Arg Ser Ala Glu Asp Glu Asn
            20

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-pyroglutamic acid
<220> FEATURE:
<221> NAME/KEY: MOD_RES
<222> LOCATION: (15)..(15)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (18)..(18)
<223> OTHER INFORMATION: D-amino acid

<400> SEQUENCE: 23

Glu Gly Pro Trp Ile Glu Glu Glu Glu Ala Tyr Ser Ser Pro Pro
1               5                   10                  15

Pro Pro Cys

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-pyroglutamic acid
<220> FEATURE:
<221> NAME/KEY: MOD_RES
<222> LOCATION: (12)..(12)
<223> OTHER INFORMATION: L-nitrophenylalanine
<220> FEATURE:
<221> NAME/KEY: MOD_RES
<222> LOCATION: (15)..(15)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (18)..(18)
<223> OTHER INFORMATION: D-amino acid

<400> SEQUENCE: 24

Glu Gly Pro Trp Leu Glu Glu Glu Glu Ala Phe Gly Ser Pro Pro
1               5                   10                  15

Pro Pro Cys

```
<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-pyroglutamic acid
<220> FEATURE:
<221> NAME/KEY: MOD_RES
<222> LOCATION: (12)..(12)
<223> OTHER INFORMATION: L-nitrophenylalanine
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (18)..(18)
<223> OTHER INFORMATION: D-amino acid

<400> SEQUENCE: 25

Glu Gly Pro Trp Leu Glu Glu Glu Glu Ala Phe Gly Ser Pro Pro
1               5                   10                  15

Pro Pro Cys

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-pyroglutamic acid
<220> FEATURE:
<221> NAME/KEY: MOD_RES
<222> LOCATION: (12)..(12)
<223> OTHER INFORMATION: L-nitrophenylalanine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (18)..(18)
<223> OTHER INFORMATION: D-amino acid

<400> SEQUENCE: 26

Glu Gly Pro Trp Leu Glu Glu Glu Glu Ala Phe Gly Ser Pro Pro
1               5                   10                  15

Pro Pro Cys

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: L-pyroglutamic acid
<220> FEATURE:
<221> NAME/KEY: MOD_RES
<222> LOCATION: (12)..(12)
<223> OTHER INFORMATION: L-nitrophenylalanine
<220> FEATURE:
<221> NAME/KEY: MOD_RES
<222> LOCATION: (18)..(18)
<223> OTHER INFORMATION: D-amino acid

<400> SEQUENCE: 27

Glu Gly Pro Trp Ile Glu Glu Glu Glu Ala Phe Gly Ser Pro Pro
1               5                   10                  15

Pro Pro Cys

<210> SEQ ID NO 28
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (19)..(19)
<223> OTHER INFORMATION: L-nitrophenylalanine
<220> FEATURE:
<221> NAME/KEY: MOD_RES
<222> LOCATION: (21)..(21)
<223> OTHER INFORMATION: D-amino acid

<400> SEQUENCE: 28

Cys Pro Pro Pro Pro Ser Ser Glu Glu Glu Glu Ala Tyr Gly Trp
1               5                   10                  15

Met Asp Phe Gly Arg Arg Ser Ala Glu Asp Glu Asn
            20                  25

<210> SEQ ID NO 29
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
```

```
<222> LOCATION: (4)..(4)
<223> OTHER INFORMATION: D-amino acid
<220> FEATURE:
<221> NAME/KEY: MOD_RES
<222> LOCATION: (19)..(19)
<223> OTHER INFORMATION: L-nitrophenylalanine
<220> FEATURE:
<221> NAME/KEY: MOD_RES
<222> LOCATION: (21)..(21)
<223> OTHER INFORMATION: D-amino acid

<400> SEQUENCE: 29

Cys Pro Pro Pro Pro Ser Ser Glu Glu Glu Glu Glu Ala Tyr Gly Trp
1               5                   10                  15

Met Asp Phe Gly Arg Arg Ser Ala Glu Asp Glu Asn
            20                  25

<210> SEQ ID NO 30
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (19)..(19)
<223> OTHER INFORMATION: L-nitrophenylalanine
<220> FEATURE:
<221> NAME/KEY: MOD_RES
<222> LOCATION: (21)..(21)
<223> OTHER INFORMATION: D-amino acid

<400> SEQUENCE: 30

Cys Pro Pro Pro Pro Ser Ser Glu Glu Glu Glu Glu Ala Tyr Gly Trp
1               5                   10                  15

Met Asp Phe Gly Arg Arg Ser Ala Glu Asp Glu Asn
            20                  25

<210> SEQ ID NO 31
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (19)..(19)
<223> OTHER INFORMATION: L-nitrophenylalanine
<220> FEATURE:
<221> NAME/KEY: MOD_RES
<222> LOCATION: (21)..(21)
<223> OTHER INFORMATION: D-amino acid

<400> SEQUENCE: 31

Cys Pro Pro Pro Pro Ser Ser Glu Glu Glu Glu Glu Ala Tyr Gly Trp
1               5                   10                  15

Met Asp Phe Gly Arg Arg Ser Ala Glu Asp Glu Asn
```

<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: L-nitrophenylalanine
<220> FEATURE:
<221> NAME/KEY: MOD_RES
<222> LOCATION: (21)..(21)
<223> OTHER INFORMATION: D-amino acid

<400> SEQUENCE: 32

Cys Pro Pro Pro Pro Ser Ser Glu Glu Glu Glu Glu Ala Tyr Gly Trp
1               5                   10                  15

Met Asp Phe Gly Arg Arg Ser Ala Glu Asp Glu Asn
            20                  25

<210> SEQ ID NO 33
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 33

Cys Pro Pro Pro Pro Ser Ser Pro Arg Ser Gln Gln Pro Asp Ala Pro
1               5                   10                  15

Leu Gly Thr Gly Ala Asn Arg
            20

<210> SEQ ID NO 34
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: D-amino acid
<220> FEATURE:
<221> NAME/KEY: MOD_RES
<222> LOCATION: (20)..(20)
<223> OTHER INFORMATION: D-amino acid
<220> FEATURE:
<221> NAME/KEY: MOD_RES
<222> LOCATION: (21)..(21)

```
<223> OTHER INFORMATION: D-amino acid
<220> FEATURE:
<221> NAME/KEY: MOD_RES
<222> LOCATION: (22)..(22)
<223> OTHER INFORMATION: D-amino acid

<400> SEQUENCE: 34

Pro Arg Ser Gln Gln Pro Asp Ala Pro Leu Gly Thr Gly Ala Asn Arg
1               5                   10                  15

Ser Ser Pro Pro Pro Pro Cys
            20

<210> SEQ ID NO 35
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 35

Cys Pro Pro Pro Pro Ser Ser Ala Ser Trp Lys Pro Arg Ser Gln Gln
1               5                   10                  15

Pro Asp Ala Pro Leu Gly Thr Gly Ala Asn Arg
            20                  25

<210> SEQ ID NO 36
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: D-amino acid
<220> FEATURE:
<221> NAME/KEY: MOD_RES
<222> LOCATION: (24)..(24)
<223> OTHER INFORMATION: D-amino acid
<220> FEATURE:
<221> NAME/KEY: MOD_RES
<222> LOCATION: (25)..(25)
<223> OTHER INFORMATION: D-amino acid
<220> FEATURE:
<221> NAME/KEY: MOD_RES
<222> LOCATION: (26)..(26)
<223> OTHER INFORMATION: D-amino acid

<400> SEQUENCE: 36

Ala Ser Trp Lys Pro Arg Ser Gln Gln Pro Asp Ala Pro Leu Gly Thr
1               5                   10                  15

Gly Ala Asn Arg Ser Ser Pro Pro Pro Pro Cys
            20                  25
```

```
<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 37

Cys Pro Pro Pro Pro Ser Ser Gly Thr Gly Ala Asn Arg Asp Leu Glu
1               5                   10                  15

Leu Pro Trp Leu Glu Gln
            20

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: D-amino acid
<220> FEATURE:
<221> NAME/KEY: MOD_RES
<222> LOCATION: (20)..(20)
<223> OTHER INFORMATION: D-amino acid
<220> FEATURE:
<221> NAME/KEY: MOD_RES
<222> LOCATION: (21)..(21)
<223> OTHER INFORMATION: D-amino acid

<400> SEQUENCE: 38

Gly Thr Gly Ala Asn Arg Asp Leu Glu Leu Pro Trp Leu Glu Gln Ser
1               5                   10                  15

Ser Pro Pro Pro Pro Cys
            20

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-pyroglutamic acid
```

```
<220> FEATURE:
<221> NAME/KEY: MOD_RES
<222> LOCATION: (12)..(12)
<223> OTHER INFORMATION: L-nitrophenylalanine
<220> FEATURE:
<221> NAME/KEY: MOD_RES
<222> LOCATION: (19)..(19)
<223> OTHER INFORMATION: D-amino acid

<400> SEQUENCE: 39

Glu Gly Pro Trp Leu Glu Glu Glu Glu Ala Phe Gly Ser Ser Pro
1               5                   10                  15

Pro Pro Pro Cys
            20

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (7)..(7)
<223> OTHER INFORMATION: D-amino acid
<220> FEATURE:
<221> NAME/KEY: MOD_RES
<222> LOCATION: (8)..(8)
<223> OTHER INFORMATION: D-amino acid

<400> SEQUENCE: 40

Cys Pro Pro Pro Pro Pro Pro Arg Arg Ser Ala Glu Asp Glu Asn
1               5                   10                  15

<210> SEQ ID NO 41
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: D-amino acid
<220> FEATURE:
<221> NAME/KEY: MOD_RES
<222> LOCATION: (26)..(26)
<223> OTHER INFORMATION: D-amino acid
<220> FEATURE:
<221> NAME/KEY: MOD_RES
<222> LOCATION: (27)..(27)
<223> OTHER INFORMATION: D-amino acid
```

```
<220> FEATURE:
<221> NAME/KEY: MOD_RES
<222> LOCATION: (28)..(28)
<223> OTHER INFORMATION: D-amino acid

<400> SEQUENCE: 41

Gln Pro Lys Ala Leu Gly Asn Gln Gln Pro Ser Trp Asp Ser Glu Asp
1               5                   10                  15

Ser Ser Asn Phe Lys Asp Ser Ser Pro Pro Pro Cys
            20                  25

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: D-amino acid
<220> FEATURE:
<221> NAME/KEY: MOD_RES
<222> LOCATION: (29)..(29)
<223> OTHER INFORMATION: D-amino acid
<220> FEATURE:
<221> NAME/KEY: MOD_RES
<222> LOCATION: (30)..(30)
<223> OTHER INFORMATION: D-amino acid
<220> FEATURE:
<221> NAME/KEY: MOD_RES
<222> LOCATION: (31)..(31)
<223> OTHER INFORMATION: D-amino acid

<400> SEQUENCE: 42

Gln Pro Lys Ala Leu Gly Asn Gln Gln Pro Ser Trp Asp Ser Glu Asp
1               5                   10                  15

Ser Ser Asn Phe Lys Asp Ser Ser Pro Ser Pro Pro Pro Pro Cys
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: D-amino acid
<220> FEATURE:
<221> NAME/KEY: MOD_RES
<222> LOCATION: (30)..(30)
<223> OTHER INFORMATION: D-amino acid
<220> FEATURE:
<221> NAME/KEY: MOD_RES
<222> LOCATION: (31)..(31)
<223> OTHER INFORMATION: D-amino acid

<400> SEQUENCE: 43

Gln Pro Lys Ala Leu Gly Asn Gln Gln Pro Ser Trp Asp Ser Glu Asp
1               5                   10                  15

Ser Ser Asn Phe Lys Asp Ser Ser Pro Ser Pro Pro Pro Pro Cys
            20                  25                  30

<210> SEQ ID NO 44
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: D-amino acid
<220> FEATURE:
<221> NAME/KEY: MOD_RES
<222> LOCATION: (31)..(31)
<223> OTHER INFORMATION: D-amino acid

<400> SEQUENCE: 44

Gln Pro Lys Ala Leu Gly Asn Gln Gln Pro Ser Trp Asp Ser Glu Asp
1               5                   10                  15

Ser Ser Asn Phe Lys Asp Ser Ser Pro Ser Ser Pro Pro Pro Cys
            20                  25                  30

<210> SEQ ID NO 45
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: D-amino acid
<220> FEATURE:
<221> NAME/KEY: MOD_RES
<222> LOCATION: (26)..(26)
<223> OTHER INFORMATION: D-amino acid

<400> SEQUENCE: 45

Gln Pro Lys Ala Leu Gly Asn Gln Gln Pro Ser Trp Asp Ser Glu Asp
1               5                   10                  15

Ser Ser Asn Phe Lys Asp Pro Pro Pro Cys
            20                  25

<210> SEQ ID NO 46
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: D-amino acid

<400> SEQUENCE: 46

Gln Pro Lys Ala Leu Gly Asn Gln Gln Pro Ser Trp Asp Ser Glu Asp
1               5                   10                  15

Ser Ser Asn Phe Lys Asp Ser Ser Pro Ser Ser Pro Pro Pro Cys
            20                  25                  30

<210> SEQ ID NO 47
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
```

```
<220> FEATURE:
<221> NAME/KEY: MOD_RES
<222> LOCATION: (9)..(9)
<223> OTHER INFORMATION: L-nitrophenylalanine
<220> FEATURE:
<221> NAME/KEY: MOD_RES
<222> LOCATION: (16)..(16)
<223> OTHER INFORMATION: D-amino acid

<400> SEQUENCE: 47

Cys Pro Pro Pro Pro Ser Ser Ala Phe Gly Trp Met Asp Phe Gly Arg
1               5                   10                  15

Arg Ser Ala Glu Asp Glu Asn
            20

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-pyroglutamic acid
<220> FEATURE:
<221> NAME/KEY: MOD_RES
<222> LOCATION: (15)..(15)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (18)..(18)
<223> OTHER INFORMATION: D-amino acid

<400> SEQUENCE: 48

Glu Gly Pro Trp Ile Glu Glu Glu Glu Glu Ala Tyr Gly Ser Pro Pro
1               5                   10                  15

Pro Pro Cys

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-pyroglutamic acid
<220> FEATURE:
<221> NAME/KEY: MOD_RES
<222> LOCATION: (12)..(12)
<223> OTHER INFORMATION: L-nitrophenylalanine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (18)..(18)
<223> OTHER INFORMATION: D-amino acid

<400> SEQUENCE: 49
```

```
Glu Gly Pro Trp Ile Glu Glu Glu Glu Ala Phe Gly Ser Pro Pro
1               5                   10                  15

Pro Pro Cys

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-pyroglutamic acid
<220> FEATURE:
<221> NAME/KEY: MOD_RES
<222> LOCATION: (12)..(12)
<223> OTHER INFORMATION: L-nitrophenylalanine
<220> FEATURE:
<221> NAME/KEY: MOD_RES
<222> LOCATION: (18)..(18)
<223> OTHER INFORMATION: D-amino acid

<400> SEQUENCE: 50

Glu Gly Pro Trp Leu Glu Glu Glu Glu Ala Phe Gly Ser Pro Pro
1               5                   10                  15

Pro Pro Cys

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (14)..(14)
<223> OTHER INFORMATION: L-nitrophenylalanine
<220> FEATURE:
<221> NAME/KEY: MOD_RES
<222> LOCATION: (21)..(21)
<223> OTHER INFORMATION: D-amino acid

<400> SEQUENCE: 51

Cys Pro Pro Pro Pro Ser Ser Glu Glu Glu Glu Ala Phe Gly Trp
1               5                   10                  15

Met Asp Phe Gly Arg Arg Ser Ala Glu Asp Glu Asn
            20                  25

<210> SEQ ID NO 52
<211> LENGTH: 28
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (14)..(14)
<223> OTHER INFORMATION: L-nitrophenylalanine
<220> FEATURE:
<221> NAME/KEY: MOD_RES
<222> LOCATION: (21)..(21)
<223> OTHER INFORMATION: D-amino acid

<400> SEQUENCE: 52

Cys Pro Pro Pro Pro Ser Ser Glu Glu Glu Glu Glu Ala Phe Gly Trp
1               5                   10                  15

Met Asp Phe Gly Arg Arg Ser Ala Glu Asp Glu Asn
            20                  25

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (14)..(14)
<223> OTHER INFORMATION: L-nitrophenylalanine
<220> FEATURE:
<221> NAME/KEY: MOD_RES
<222> LOCATION: (21)..(21)
<223> OTHER INFORMATION: D-amino acid

<400> SEQUENCE: 53

Cys Pro Pro Pro Pro Ser Ser Glu Glu Glu Glu Glu Ala Phe Gly Trp
1               5                   10                  15

Met Asp Phe Gly Arg Arg Ser Ala Glu Asp Glu Asn
            20                  25

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:

```
<221> NAME/KEY: MOD_RES
<222> LOCATION: (14)..(14)
<223> OTHER INFORMATION: L-nitrophenylalanine
<220> FEATURE:
<221> NAME/KEY: MOD_RES
<222> LOCATION: (21)..(21)
<223> OTHER INFORMATION: D-amino acid

<400> SEQUENCE: 54

Cys Pro Pro Pro Pro Ser Ser Glu Glu Glu Glu Glu Ala Phe Gly Trp
1               5                   10                  15

Met Asp Phe Gly Arg Arg Ser Ala Glu Asp Glu Asn
            20                  25

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: L-nitrophenylalanine
<220> FEATURE:
<221> NAME/KEY: MOD_RES
<222> LOCATION: (21)..(21)
<223> OTHER INFORMATION: D-amino acid

<400> SEQUENCE: 55

Cys Pro Pro Pro Pro Ser Ser Glu Glu Glu Glu Glu Ala Phe Gly Trp
1               5                   10                  15

Met Asp Phe Gly Arg Arg Ser Ala Glu Asp Glu Asn
            20                  25

<210> SEQ ID NO 56
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: D-amino acid
<220> FEATURE:
<221> NAME/KEY: MOD_RES
<222> LOCATION: (20)..(20)
<223> OTHER INFORMATION: D-amino acid
<220> FEATURE:
<221> NAME/KEY: MOD_RES
<222> LOCATION: (21)..(21)
<223> OTHER INFORMATION: D-amino acid

<400> SEQUENCE: 56

Pro Arg Ser Gln Gln Pro Asp Ala Pro Leu Gly Thr Gly Ala Asn Arg
1               5                   10                  15

Cys Pro Pro Pro Pro Ser Ser
            20

<210> SEQ ID NO 57
<211> LENGTH: 23
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 57

Cys Pro Pro Pro Pro Ser Ser Pro Arg Ser Gln Gln Pro Asp Ala Pro
1               5                   10                  15

Leu Gly Thr Gly Ala Asn Arg
            20

<210> SEQ ID NO 58
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (19)..(19)
<223> OTHER INFORMATION: D-amino acid
<220> FEATURE:
<221> NAME/KEY: MOD_RES
<222> LOCATION: (20)..(20)
<223> OTHER INFORMATION: D-amino acid

<400> SEQUENCE: 58

Gly Thr Gly Ala Asn Arg Asp Leu Glu Leu Pro Trp Leu Glu Gln Cys
1               5                   10                  15

Pro Pro Pro Pro Ser Ser
            20

<210> SEQ ID NO 59
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: D-amino acid
<220> FEATURE:
<221> NAME/KEY: MOD_RES
<222> LOCATION: (21)..(21)
<223> OTHER INFORMATION: D-amino acid
<220> FEATURE:
<221> NAME/KEY: MOD_RES
```

```
<222> LOCATION: (22)..(22)
<223> OTHER INFORMATION: D-amino acid
<220> FEATURE:
<221> NAME/KEY: MOD_RES
<222> LOCATION: (23)..(23)
<223> OTHER INFORMATION: D-amino acid

<400> SEQUENCE: 59

Ser Ser Gly Thr Gly Ala Asn Arg Asp Leu Glu Leu Pro Trp Leu Glu
1               5                   10                  15

Gln Ser Ser Pro Pro Pro Pro Cys
            20

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-pyroglutamic acid
<220> FEATURE:
<221> NAME/KEY: MOD_RES
<222> LOCATION: (12)..(12)
<223> OTHER INFORMATION: L-nitrophenylalanine
<220> FEATURE:
<221> NAME/KEY: MOD_RES
<222> LOCATION: (15)..(15)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (18)..(18)
<223> OTHER INFORMATION: D-amino acid

<400> SEQUENCE: 60

Glu Gly Pro Trp Leu Glu Glu Glu Glu Ala Phe Gly Cys Pro Pro
1               5                   10                  15

Pro Pro Ser Ser
            20

<210> SEQ ID NO 61
<211> LENGTH: 7
<212> TYPE: PRT
<213> ORGANISM: Unknown
<220> FEATURE:
<223> OTHER INFORMATION: Description of Unknown:
      bombesin sequence

<400> SEQUENCE: 61

Trp Ala Val Gly His Leu Met
1               5

<210> SEQ ID NO 62
<211> LENGTH: 6
<212> TYPE: PRT
<213> ORGANISM: Unknown
<220> FEATURE:
<223> OTHER INFORMATION: Description of Unknown:
      Progastrin family sequence
```

```
<400> SEQUENCE: 62

Ser Ala Glu Asp Glu Asn
1               5

<210> SEQ ID NO 63
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Pro Lys Ala Leu Gly Asn Gln Gln Pro Ser Trp Asp Ser Glu Asp
1               5                   10                  15

Ser Ser Asn Phe Lys Asp
            20

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Methionine amide

<400> SEQUENCE: 64

Tyr Pro Arg Gly Asn His Trp Ala Val Gly His Leu Met
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-nitrophenylalanine
<220> FEATURE:
<221> NAME/KEY: MOD_RES
<222> LOCATION: (13)..(13)
<223> OTHER INFORMATION: Methionine amide

<400> SEQUENCE: 65

Phe Pro Arg Gly Asn His Trp Ala Val Gly His Leu Met
1               5                   10

<210> SEQ ID NO 66
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Thr Val Leu Thr Lys Met Tyr Pro Arg Gly Asn His Trp Ala Val
1               5                   10                  15

Gly His Leu
```

```
<210> SEQ ID NO 67
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Gly Gly Gly Thr Val Leu Thr Lys Met Tyr Pro Arg Gly Asn His
1               5                   10                  15

Trp Ala Val Gly His Leu
            20

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: L-hydroxyproline
<220> FEATURE:
<221> NAME/KEY: MOD_RES
<222> LOCATION: (3)..(3)
<223> OTHER INFORMATION: L-hydroxyproline
<220> FEATURE:
<221> NAME/KEY: MOD_RES
<222> LOCATION: (4)..(4)
<223> OTHER INFORMATION: L-hydroxyproline
<220> FEATURE:
<221> NAME/KEY: MOD_RES
<222> LOCATION: (5)..(5)
<223> OTHER INFORMATION: L-hydroxyproline

<400> SEQUENCE: 68

Cys Pro Pro Pro Pro Ser Ser
1               5

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Pro Leu Pro Ala Gly Gly Gly Thr Val Leu Thr Lys Met Tyr Pro
1               5                   10                  15

Arg Gly Asn His
            20

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: L-nitrophenylalanine

<400> SEQUENCE: 70

Ala Phe Gly Trp Met Asp Phe Gly Arg Arg Ser Ala Glu Asp Glu Asn
```

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-pyroglutamic acid

<400> SEQUENCE: 71

Glu Gly Pro Trp Ile Glu Glu Glu Glu Glu Ala Tyr Gly
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-pyroglutamic acid
<220> FEATURE:
<221> NAME/KEY: MOD_RES
<222> LOCATION: (12)..(12)
<223> OTHER INFORMATION: L-nitrophenylalanine

<400> SEQUENCE: 72

Glu Gly Pro Trp Leu Glu Glu Glu Glu Glu Ala Phe Gly
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Pro Pro Pro Pro Ser Ser
1               5

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Arg Ser Gln Gln Pro Asp Ala Pro Leu Gly Thr Gly Ala Asn Arg
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 75

Gly Thr Gly Ala Asn Arg Asp Leu Glu Leu Pro Trp Leu Glu Gln
1               5                   10                  15
```

COMPOSITION OF TUMOR-ASSOCIATED PROLIFERATIVE PEPTIDES AND RELATED ANTI-CANCER IMMUNOGEN FOR THE TREATMENT OF LUNG CANCERS AND OTHER CANCERS

CROSS REFERENCE TO RELATED APPLICATIONS

This is a U.S. National Phase Application under 35 U.S.C. § 371 of International Patent Application No. PCT/IB2018/056313, filed Aug. 21, 2018, which claims priority of U.S. Patent Application No. 62/548,493, filed Aug. 22, 2017. The entire contents of which are hereby incorporated by reference.

SEQUENCE LISTING

This application contains a Sequence Listing which has been submitted in ASCII format via EFS-Web and is hereby incorporated by reference in its entirety. Said ASCII document, created on Dec. 22, 2021 was named 256583_000002_.txt and is 41,220 bytes in size.

FIELD OF THE INVENTION

The present invention relates to immunotherapeutic peptides and their use in immunotherapy, in particular the immunotherapy of cancer. The present invention discloses tumor-growth factor associated peptide epitopes, alone or in combination with other tumor-growth factor associated peptides that serve as active pharmaceutical ingredients of vaccine compositions, which stimulate anti-tumor immune responses inhibiting growth and proliferation. In particular, the composition of the peptides of the present invention can be used in vaccine compositions for eliciting anti-tumor immune responses against growth of lung, gastric and other cancers.

For the purposes of the present invention, all references as cited herein are incorporated by reference in their entireties.

BACKGROUND OF THE INVENTION

The leading cause of cancer death in China is malignant lung neoplasms, and it leads among all others world-wide, as the predominant cause of all cancer deaths. Sadly, the mortality of lung cancer is increasing every year in China as well as in other major countries, such as the United States and Russia. Liu and coworkers had estimated that nearly 800,000 Chinese men would die of lung cancer in 1998 Hao J, Zhao P, Chen W [Chinese Cancer Registry Annual Report 2012. Beijing Military Medical Science Press]; 2013 [Chinese]. Similarly, others have predicted that China, where one-third of the world's smokers reside, will have millions of lung cancer deaths annually by the middle of the 21st century. The average number of cigarettes smoked by every adult male in China is 11 per day, with 67% of the male population being smokers, equivalent to the highest rate ever seen in the United States.

As the world's largest producer and consumer of tobacco. China bears a substantial proportion of the global burden of smoking-related disease. Of China's population of 1.3 billion, more than 350 million men and 30 million women are smokers, making China the world's largest actual and potential national market for cigarettes. The average smoker is estimated to spend about 25% of their income on cigarettes. China is considered to be in an early stage of a tobacco epidemic, but the burden of disease attributable to smoking in China will assume greater prominence in coming years. It is estimated that deaths due to smoking will increase from about 1 million worldwide in 1995 to more than 7 million in 2025. Jemal A. Bray F, Center MM, Ferlay J, Ward E. Forman D. Global cancer statistics. CA Cancer J Clin, 2011; 61(2):69-90. At current smoking rates, by the year 2025, 2 million smoking-related deaths are predicted to occur in China, and at least 50 million Chinese smokers alive today are expected to die prematurely. Data from China's disease surveillance point (DSP) system indicate that China is experiencing an epidemic of diseases caused by tobacco. She J, Yang P, Hong Q, Bai C. Lung cancer in China: challenges and interventions. Chest. 2013; 143(4):1117-1126.

Lung cancers are histopathologically classified into the following four main tissue types: lung squamous-cell carcinoma (SCC) and small-cell lung carcinoma (SCLC) developing in the hilar area of the lung, and non small cell lung (adeno)carcinoma (NSCLC) and bronchogenic large-cell lung carcinoma (LCLC) developing in the lung. The most common cause of lung cancer is long-term exposure to tobacco smoke, which causes 80-90% of lung cancers. Nonsmokers account for 10-15% of lung cancer cases, and these cases are often attributed to a combination of air pollution, genetic factors, radon gas, as well as second hand smoke. Lung cancer accounts for the most cancer-related deaths in both men and women. In fact, according to GLOBOCAN 2008 Jemal A, Siegel R, Xu J, Ward E. Cancer statistics, 2010. CA Cancer J Clin. 2010; 60:277-300 the most commonly diagnosed cancers worldwide are lung cancer (1.61 million, 12.7% of the total), and the most common causes of cancer deaths are also from lung cancers (1.38 million, 18.2% of the total), with stomach cancer and liver cancers making up second place (738,000 deaths, 9.7% and 696,000 deaths, 9.2%, respectively).

Immunological treatment against specific cancer-promoting growth factors and hormones is known to be useful in the therapy and recurrence of certain cancers, especially breast cancer, lung cancer, and certain types of GI cancer. In addition, immunological approaches to the treatment and prevention of pulmonary and aero-digestive diseases also may be effective in the treatment of these chronic conditions.

Several treatment approaches have been employed successfully, especially ones that use targeted human or humanized monoclonal antibodies (huMAbs). Given the great expense and technical difficulties of setting up manufacture and delivery of commercial huMAbs, however, more affordable, alternative strategies are needed, particularly for the developing countries and developed countries that are seeking to minimize excessively rising health care costs, yet maintain efficacious therapies.

For lung cancers and related malignant diseases, these immunological approaches entail the generation of specific antibodies to neutralize the biological activity of disease promoting gastrointestinal peptide family of hormones. The antibodies that are required have to be specific for a particular growth factor or hormone, or hormone precursor. One or more factors or even a family of hormones can be selectively targeted to treat a particular disease, for example, small cell lung carcinoma (SCLC) and non-small cell lung carcinoma (NSCLC), which have in the past been considered to be derived from distinct cell lineages, because of differences in histology and clinical behavior. Small cell tumors were believed to originate from neuroendocrine cells within the lung; these neuroendocrine cells in turn were thought to originate from the neural crest and to migrate to the lung during fetal development. Non-small cell lung tumors were believed to originate from cells within the basal cell layer of the bronchial epithelium, which were capable of differentiating into the ciliated, mucin producing, bronchiolar exocrine cells, and alveolar cells during normal development, and into squamous metaplastic cells following tissue injury. Recent evidence suggests however that this dual model of lung development is incorrect, and that pulmonary neuroendocrine cells are derived from the endoderm and is intrinsic to the lung. These cells are in fact, the first differentiated type to be observed during formation of the lungs in the fetus, and appear to influence the maturation of other lung cell types through secretion of bioactive peptides, many seemingly related to the gastrin family of proteins, factors such as the gastrin-releasing peptides (GRP) Yamaguchi, K. Abe K, Kameya T. Adachi I, Taguchi S, Otsubo K, Yanaihara N. Production and molecular size heterogeneity of immunoreactive gastrin-releasing peptide in fetal and adult lungs and primary lung tumors. Cancer Res. 43 (1983) 3932-3939 and gastrin and their precursor peptides Rehfeld J F, Bardram L, and Hilsted L., Gastrin in Human Bronchogenic Carcinomas: Constant Expression but Variable Processing of Progastrin. Cancer Res. 1989 49, 2840-2843.

GRP, is one member of the bombesin family of bioactive peptides, and is an important growth-modulating factor in developing lung epithelium K. Yamaguchi, K. Abe, T. Kameya, I. Adachi, S. Taguchi, K. Otsubo. N. Yanaihara, Production and molecular size heterogeneity of immunoreactive gastrin-relcasing peptide in fetal and adult lungs and primary lung tumors, Cancer Res. 43 (1983) 3932-393. Several lines of evidence also suggest that multipotent stem cells may exist in the lung that are capable of differentiating into both mature neuroendocrine cells and other mature cells, such as ciliated cells. Some lung tumors contain both SCLC and NSCLC elements as separate parts of the same malignancy. The neuroendocrine phenotype can also be found in up to 15% of NSCLC tumors E. Rozengurt, Neuropeptides as growth factors for normal and cancerous cells, Trends Endocrinol. Metab. 13 (2002) 128-134. In addition, SCLC tumors have been shown to contain receptors for epidermal growth factor (EGFR), a common signaling pathway in NSCLC as well.

SCLC transitions towards a NSCLC phenotype have also been observed during the progression of lung cancer disease; drug-resistant cells with features of large cell carcinoma have been found to predominate SCLC patients after relapse Mattei J, Achcar R D, Cano CH, et al., Gastrin-Releasing Peptide Receptor Expression in Lung Cancer. Arch Pathol Lab Med Vol 138, January 2014. Studies by Mabry and coworkers suggest that SCLC cells can be experimentally manipulated to display a NSCLC phenotype by the introduction of a mutated Harvey-Ras (hRAS) gene in cell cultures that overexpress the c- or N-myc genes. These transitioned cells display a NSCLC histology and begin expressing the genes for the epidermal growth factor receptor and transforming growth factor-α. The secretion of GRP and expression of its receptor are relatively diminished in these cultures, but levels are higher in those that retain the more aggressive neuroendocrine phenotype that appear to be more chemo-resistant and stem cell-like Mabry M, Nelkin BD, Falco JP, Barr LF, Baylin SB. Transitions between lung cancer phenotypes--implications for tumor progression. Cancer Cells. 1991 Feb.;3(2):53-8. Review. PubMed PMID: 1851429.

These observations suggest there are significant similarities in the biology of NSCLC and SCLC. Because release of GRP and neuroendocrine hyperplasia have been suggested as early events in lung carcinogenesis, and because cells within the bronchial mucosa can respond to GRP, GRP or related peptides may be implicated in the development and/or progression of NSCLC as well as SCLC. Further, published reports, have demonstrated that NSCLC cell line can be induced to produce GRP, and take on some of the morphological features of a secretory tumor, under conditions in which all sources of growth factors are removed from the medium. It has also been demonstrated that both purified GRP and conditioned medium (CM) from A549-Ro cells containing GRP can induce proliferation in cells derived from NSCLCs, and that NSCLCs express receptors for GRP as well as other gastrin family and GRP-family related peptides. These findings demonstrate that NSCLC can share features with SCLC, and that the gastrins and GRP may be a common mitogenic molecule for many lung cell types, and thus gastrin family members such as GRP may be a target for therapy of NSCLC as well as SCLC Moody TW. Peptide hormones and lung cancer. Panminerva Med. 2006 Mar.;48(1):19-26. Although NSCLC is the predominant type of lung cancer in China, SCLC and its related neuroendocrine-malignant types, still constitute some 30% to 40% of all lung cancers, particularly in late stage malignant pulmonary disease. Despite major improvements in targeted treatments of lung cancer, and also with conventional chemotherapies, over 90% of these SCLC/NSCLC patients die of their malignancy, making these diseases among the worlds deadliest.

Of particular significance, is that small-cell lung carcinoma rapidly proliferates and causes remote metastasis in its early stage, and therefore, in many cases, this carcinoma is discovered to be an advanced cancer, which has already metastasized systemically, even at the time of initial diagnosis. With regard to the practical cure rate of this type of cancer, the cure rate in patients with limited disease small-cell lung carcinoma in which the lesion is limited only to one side of the lung field is approximately 10-20%; however in patients with extensive disease, small-cell lung carcinoma in which the lesion has metastasized to both lungs or to other organs is almost always fatal.

Furthermore, since small-cell lung carcinoma is highly sensitive to anticancer drugs, and shows good responsiveness, chemotherapy is considered as the first choice of therapy. By contrast, non-small-cell lung carcinoma (NSCLC) shows a low response rate for chemotherapy, and thus surgery is considered as the first choice of therapy, where possible.

Consequently, small-cell lung carcinoma is a cancer, which particularly necessitates early discovery and early treatment even among various types of lung cancers. Therefore, differential diagnosis of small-cell lung carcinoma and non-small-cell lung carcinoma is extremely important for making decision on the therapeutic strategy.

The seminal Hallmarks of Cancer article postulates that cancer growth is made independent of exquisitely regulated cell signaling processes that permit the malignant cell (or its tumor micro-environmental neighbors) to produce both its stimulatory growth factor(s) and its cognate receptor(s) Hanahan D, and Weinberg RA. The Hallmarks of Cancer: Then Next Generation. Cell 2011 Volume 144, Issue 5:646-74 and that this autocrine or paracrine interaction results in dysfunctional and unregulated proliferation. The recognition of a number of hormonal factors in this malignant process involving the gastrin family in GI cancers and the gastrin-releasing peptides (GRP) in pulmonary cancers as being the prototypical autocrine growth factors was widely studied and well-validated Patel 0, Shulkes A, Baldwin GS. Gastrin-releasing peptide and cancer. Biochim Biophys Acta. 2006; 1766(1):23-41. GRP family involvement in lung cancers was originally based on the detection of bombesin family polypeptides such as GRP and its cognate receptor, as well as the anti-proliferative effect of GRP antibodies, in small cell lung carcinoma (SCLC) (13). In support of this functional role, GRP has been also described as a potent mitogen for several other types of carcinomas including colon, pancreas, prostate and breast J. Zhou, J. Chen. M. Mokotoff, E. D. Ball, Targeting gastrin-releasing peptide receptors for cancer treatment. Anti-cancer Drugs 15 (2004) 921-927, and the signaling pathways involved in mitogenesis have been studied extensively. Recent data show that GRP is not only an autocrine mitogen, but also has paracrine and endocrine effects, and functions as a morphogen and a proangiogenic agent. The presence of high affinity GRP receptors in many cancers has also allowed the development of reagents for diagnosis, radiotherapy and chemotherapy J. C. Reubi, S. Wenger, J. Schmuckli-Maurer, J. C. Schaer. M. Gugger, Bombesin receptor subtypes in human cancers: detection with the universal radioligand (125)I-[D-TYR(6), beta-ALA (11), PHE(13), NLE (14)] bombesin(6-14), Clin. Cancer Res. 8 (2002) 1139-1146.

The discovery of GRP, and the availability of antiserum against this peptide, led to the demonstration of immunoreactivity in tissue extracts and the immunocytochemical localization of GRP. The occurrence of GRP immunoreactivity in human lung has been well documented in both adult N. Bunnett, Gastrin-releasing peptide, Gut Peptides: Biochemistry and Physiology, Raven Press Ltd, New York, 1994 and fetal tissue K. Yamaguchi. K. Abe. T. Kameya. I. Adachi, S. Taguchi, K. Otsubo, N. Yanaihara. Production and molecular size heterogeneity of immunoreactive gastrin-releasing peptide in fetal and adult lungs and primary lung tumors. Cancer Res. 43 (1983) 3932-3939. Yamaguchi and co-workers using a radioimmunoassay specific for the C-terminus of GRP detected immunoreactive GRP in all (5/5) fetal lung samples K. Yamaguchi, K. Abe, T. Kameya, I. Adachi. S. Taguchi, K. Otsubo. N. Yanaihara, Production and molecular size heterogeneity of immunoreactive gastrin-releasing peptide in fetal and adult lungs and primary lung tumors, Cancer Res. 43 (1983) 3932-3939. GRP has also been detected in other human tissues including the pancreas, thymus, prostate and urethra Gonzalez N, Moody TW, Igarashi H, I to T, Jensen RT. Bombesin-related peptides and their receptors: recent advances in their role in physiology and disease states. Curr Opin Endocrinol Diabetes Obes. 2008 Feb.;15(1):58-64.

The GRP-like peptides play many physiological roles in addition to the stimulation of gastric acid secretion. As well as stimulating the release of a variety of hormones including gastrin, somatostatin and CCK, the GRP-like peptides promote exocrine secretion from the pancreas, and smooth muscle contraction in stomach, small intestine, and several other tissues Ramos-Alvarez I, Moreno P, Mantey SA, Nakamura T, Nuche-Berenguer B, Moody TW, Coy DH, Jensen RT. Insights into bombesin receptors and ligands: Highlighting recent advances. Peptides. 2015 Oct.;72:128-44. Relative to the effects of GRP on cancer, we will consider only the abilities of GRP-like peptides to stimulate cell mitogenesis, cell proliferation and to inhibit apoptosis Ischia J, Patel 0, Shulkes A, Baldwin GS. Gastrin-releasing peptide: different forms, different functions. Biofactors. 2009 Jan-Feb;35(1):69-75.

Human SCLC cells have been shown to contain significant concentrations of GRP. Using RT-PCR amplification, GRP mRNA was detected in several SCLC cell lines (LU165. SBC1, SBC2, and SBC3) but not in some non-SCLC cell lines (A549, ABC1, EBC1, and Oka-1). GRP-like immunoreactivity has also been described in many SCLC and carcinoid cell lines, Cuttitta F, Carney DN, Mulshine J, et al. Bombesin-like peptides can function as autocrine growth factors in human small-cell lung cancer. Nature. 1985; 316(6031):823-826. Similar patterns of GRP expression, consisting mainly of GRP18-27 and some GRP14-27, together with large fragments of C-terminal proGRP, were observed by gel filtration chromatography in extracts of three SCLC cell lines (NIC-H345, NIC-H69, and NIC-H510) Moody TW, Pert CB, Gazdar AF, Carney DN, Minna JD. High levels of intracellular bombesin characterize human small-cell lung carcinoma. Science. 1981;214(4526): 1246.

In patients with SCLC. GRP mRNA was detected in 50% (16/32) of blood samples, 18% (2/11) of marrow samples, and all pleural effusion samples (6/6) Mattei J, Achcar RD, Cano CH, et al., Gastrin-Releasing Peptide Receptor Expression in Lung Cancer. Arch Pathol Lab Med Vol 138, January 2014. Blood samples from 58% (11/19) of the patients with extensive disease gave positive results as compared to 38% (5/13) of patients with limited disease. In contrast, less than 3% (1/38) of blood samples from patients with non-SCLC lung adenocarcinoma gave a positive result. Immunoreactive GRP was found in 74% of human SCLC examined (23/31), and 29% (9/31) of these contained large amounts of immunoreactive GRP (0.1 to 13 nmol/g) Sunday ME, Choi N, Spindel ER, Chin WW, Mark EJ. Gastrin-releasing peptide gene expression in small cell and large cell undifferentiated lung carcinomas. Hum Pathol. 1991; 22(10):1030-1039. Using an assay that measures pro-GRP31-98 (part of the C terminal flanking peptide of GRP) a number of groups have reported elevated circulating concentrations of proGRP Chaudhry A, Carrasquillo JA, Avis IL, Shuke N, Reynolds JC, Bartholomew R, Larson SM, Cuttitta F, Johnson BE, Mulshine JL. Phase I and imaging trial of a monoclonal antibody directed against gastrin-releasing peptide in patients with lung cancer. Clin Cancer Res. 1999 Nov.; 5(11):3385-93. The observation that proGRP concentrations were increased in more than 80% of patients with SCLC and decreased following resection suggests that it may be a useful marker for diagnosis, treatment and monitoring Rehfeld JF, Bardram L, and Hilsted L., Gastrin in Human Bronchogenic Carcinomas: Constant Expression but Variable Processing of Progastrin. Cancer Res. 1989 49, 2840-2843. Indeed, it is now considered to be a significant prognostic marker Smith AM, Morris T, Justin T, Michaeli D, and Watson SA.,Gastrimmune-induced anti-gastrin-17 antibodies inhibit acid secretion in a rat fistula model. Aliment Pharmacol Ther 2001; 15: 1981±1988. Interestingly as noted above, SCLC cell lines also produce large amounts of C-terminal flanking GRP peptides van Solinge WW, Odum L, and Rehfeld JF. Ovarian Cancers Express and Process Progastrin. Cancer Research 1993 53, 1823-1828. It is now well established that GRP is a potent mitogen for various cancer cells in culture and in experimental models of animal carcinogenesis. Thus GRP inhibition would therefore seem to be an effective treatment target for several malignancies, especially for lung cancers where high levels of GRP are found secreted and GRP was seen to be mitogenic. In a study in which a human SCLC cell line (NCI-H69) was subcutaneously implanted into the flanks of nude mice, bombesin treatment significantly increased tumor weight and DNA content Dalm SU, Verzijlbergen JF, and De Jong M. Receptor Targeted Nuclear Imaging of Breast Cancer. Int. J. Mol. Sci. 2017. 18(2), 260-77. A study using the synthetic octapeptides as GRP antagonists were able to inhibit the in vitro and in vivo growth of GRP receptor-positive SCLC. Additionally, GRP analogues inhibited the increase in cytosolic $Ca^{2+}$ and the growth of SCLC in vitro by approximately 70% and also inhibited the growth of SCLC xenografts in nude mice in vivo by approximately 50%. Subcutaneous treatment of nude mice xenografted with H69 SCLC cells with the GRP antagonists for 5 weeks resulted in decreases in tumor volume of 50-70%. Tumor burden was also significantly decreased in both treated groups Yashi M, Muraishi 0, Kobayashi Y, Tokue A, Nanjo H. Elevated serum progastrin-releasing peptide (31-98) in metastatic and androgen-independent prostate cancer patients. Prostate. 2002 May 1;51(2):84-97. Substantially less data has been available for other gastrin family hormones and peptides, as proliferative and pro-mitotic factors in these malignant diseases, but the fact that their receptors are detected in many tumors and that such factors are nearly ubiquitously present during and following meals makes them ideal components to fuel malignant diseases.

Recent data has shown that gastrin family prohormones and prohormone-derived peptides, which were originally thought to be inactive are in fact, active via novel receptor-functional proteins Yashi M, Nukui A, Kurokawa S, Ochi M, Ishikawa S, Goto K, Kobayashi Y, Muraishi 0, Tokue A. Elevated serum progastrin-releasing peptide (31-98) level is a predictor of short response duration after hormonal therapy in metastatic prostate cancer. Prostate. 2003 Sep. 1; 56(4): 305-12. Thus although the amidated forms of peptide hormones were thought for many years to be the only biologically active species, in the last decade several glycine-extended hormone precursors such as gastrin and secretin have been shown to be active Hampton, M. B.; Kettle, A. J.; Winterbourn, C. C. Inside the neutrophil phagosome: oxidants, myeloperoxidase and bacterial killing. Blood 92:3007-3017; 1998. In the case of GRP, processing of the prohormone gives rise to both amidated and glycine-extended forms, including GRP1-27gly and GRP18-27gly. Studies have shown that the glycine-extended form of bombesin is biologically active in Swiss 3T3 cells, in pancreatic acini and in the SCLC cell line NCI-H345 Moody TW, Pert CB, Gazdar AF, Carney DN, Minna JD. High levels of intracellular bombesin characterize human small-cell lung carcinoma. Science. 1981;214(4526):1246. Recently, Patel and co-workers have shown that the glycine-extended form of GRP (GRPgly) stimulates proliferation and migration in colorectal cell lines.

From the above literature, it is apparent that GRP receptors are over-expressed in small cell lung, prostate, gastric, breast, pancreatic and colorectal cancers. In fact early clinical trials using a mouse antibody against GRP had been conducted in patients with lung cancers.

Several antibody-based strategies have been investigated. Early work from Cuttitta and co-workers showed that a mouse monoclonal antibody (MAb) against GRP was able to block proliferation of SCLC cell lines. The efficacy of the same antibody has also been investigated in phase I and 1I trials with SCLC patients. Of the thirteen patients observed in the phase II trial, stable disease was achieved in four, and the disease was eradicated in one. In an alternative approach, a GRP-R agonist or antagonist was coupled to a monoclonal antibody against the Fc receptor, in order to redirect immune effector cells to tumor cells that expressed the GRP-R. In both cases lysis of SCLC tumor cells in vitro was enhanced.

From the above literature, given that it is apparent that GRP receptors are over-expressed in small cell lung and neuroendocrine rich lung cancers, as well as prostate, gastric, pancreatic, colorectal and other cancers and that GRP is both mitogenic and anti-apoptotic, warrants its inhibition and its justified targeting. Even a very limited patient study with a mouse MAb showed both safety and some efficacy that strongly warrants further human investigations.

Current lung cancer treatment options are determined by the type (small cell or non-small cell) and stage of cancer and include surgery, radiation therapy, chemotherapy, and costly targeted biological therapies such as bevacizumab (Avastin®) and erlotinib (Tarceva®). In limited cases, or localized cancers, surgery is usually the primary treatment of choice. Recent studies indicate that survival with early-stage, non-small cell lung cancer is improved by chemotherapy following surgery. Because in most cases, the lung cancer disease has usually spread by the time it is discovered, radiation therapy and chemotherapy are often used, sometimes, if possible, in combination with surgery. Chemotherapy alone or combined with radiation is the usual treatment of choice for small cell and non-small cell lung cancers. Using this regimen, a large percentage of patients experience remission, however recurrence of disease usually occurs.

The 1-year relative survival for lung cancer has slightly increased from 37% in 1975-1979 to 42% in 2002, largely due to improvements in surgical techniques and combined therapies. However, the 5-year survival rate for all stages combined is only 16% in the United States and 5% in the UK, EU and Asia. Early diagnosis does improve survival rates. There is a 49% survival for cases detected while the disease is still localized: however, only about 10% of lung cancers are typically diagnosed at this early stage. Unfortunately the vast majority of lung cancer patients present with advanced disease and thus 5 year survival rate is unacceptably low. This situation begs for improvement in new therapies, such as those that would utilize GRP family blocking to restrict proliferation and effect apoptosis sensitivity. Other cancers that express GRP receptors and GRP peptide growth factors also would benefit as well.

There also remains a need for new efficacious and safe treatment option for gastric cancer, prostate carcinoma as well as for other GRP family secreting cancers like small cell lung cancer (SCLC) and non-small-cell lung cancer (NSCLC). Not to mention the GRPR receptor containing human breast cancers, prostate cancers, colorectal cancers, pancreatic cancers, pancreatic ductal adenocarcinomas, ovarian cancers, hepatocellular carcinomas, liver cancers, and esophageal carcinomas.

Importantly, there remains a need for efficacious, but reasonably priced treatment options that enhance the well-being of the patients without using high cost biologics and high dosage chemotherapeutic agents or other agents that have severe and unacceptable debilitating side effects. Recently, a novel class of drugs, molecular-targeted monoclonal antibody reagents, such as Avastin (bevacizumab) and Erbitux (cetuximab), have been approved for use, and many other monoclonal antibodies are in late-stage clinical development for different stages of lung and GI cancers. Combinations of several of these antibodies increase the number of potential treatment options to be expected for the future.

Additional antibodies are also in early clinical trials with anti-tyrosine kinase drugs as predominate anti-cancer agents. Although these targeted therapies are proving to be of limited effectiveness, their availability and affordability are concerns for most patients especially among the economically disadvantaged, where governmental resources are limited. Thus there is a need to derive more affordable treatments, yet retain the effective nature of targeted drugs, and preserve the limited adverse effects associated with such targeted treatments.

Monoclonal antibodies (MAbs) presently used in oncology in general have an excellent chance of not interfering with active immunotherapy. In fact, there is preclinical evidence suggesting that depletion of VEGF (by bevacizumab) contributes positively to DC-mediated activation of T-cells.

SUMMARY OF THE INVENTION

This and further objects are in a first aspect of the present invention achieved by providing a pharmaceutical immunogenic composition, comprising a polypeptide immunogen and a pharmaceutically acceptable vehicle, wherein the polypeptide immunogen comprises (A) one or more mimetic peptide(s) being selected from the group consisting of SEQ ID NO 1 to SEQ ID NO 75, and/or comprising a variant amino acid sequence that is at least 90% identical to that of SEQ ID NO 1 to SEQ ID NO 75, and (B) an immunogenic carrier coupled to said mimetic peptide.

In another embodiment of the invention, the pharmaceutical immunogenic composition, the one or more mimetic peptide(s) consists of an equal mixture of the amino acid sequences: CYS-pro-pro-pro-pro-SER-SER-GLN-PRO-LYS-ALA-LEU-GLY-ASN-GLN-GLN—PRO-SER-TRP-ASP-SER-GLU-ASP-SER-SER-ASN-PHE-LYS-ASP (ONKO-5a) (SEQ ID NO.: 1) and Cys-pro-pro-pro-pro-SER-SER-TYR-PRO-ARG-GLY-ASN-HIS-TRP-ALA-VAL-GLY-HIS-LEU-MET-NH$_2$ (SEQ ID NO.: 9).

In yet another embodiment of the invention, the pharmaceutical immunogenic composition, said polypeptide immunogen comprises at least one or more oligopeptides having an overall length of from 8 to 100, optionally from 8 to 30, wherein said mimetic peptides comprises one or more oligopeptides as amino acid sequences that is selected from the group consisting of: SEQ ID No.: 1 to SEQ ID NO.:75.

In yet another embodiment of the invention, the pharmaceutical composition comprises at least one or more peptides consisting of D-amino acid sequences according to SEQ ID NO.:1 to SEQ ID NO.: 75.

It is contemplated that at least the immunogen administered may include a defined mixture of immunogens. The preferred pharmaceutical immunogenic composition according to claim 1, wherein at least the immunogen administered may include a defined mixture of one or more immunogens selected from oligopeptide sequences: SEQ ID NO.:1 to SEQ ID NO.:75.

The immunogenic peptide according to the invention may be conjugated to an immunogenic proteinaceous carrier component; a preferred pharmaceutical immunogenic substance(s), generally greater than 6000 Daltons in size, such as diphtheria toxoid (DT); tetanus toxoid (TT) pertussis toxoid (PT) or any of their commercially approved combinations (e.g., TD, DPT, T-dap, BCG, etc.).

In another aspect of the invention, malignant growth may be inhibited by a method of using an immunogen generating specific anti-growth stimulating factors of Lung, GI and other cancer cells in a mammal, comprising the step of generating patient immune cells to produce a growth-inhibitory amount of antibody(s) and immune activated T-cells, wherein said antibody(s) is/are stimulated in patients administered with said immunogens that:

(i) binds the family of gastrins and gastrin releasing peptides, or bombesin-like peptide specifically and its precursor peptides which are not cross-reactive with substance P;

(ii) has singly and/or in combination, specificity for a peptide having the amino acid sequences of carboxyl terminal heptapeptide region Trp-Ala-Val-Gly-His-Leu-Met (SEQ ID NO: 61) of bombesin; and/or for the type I II and III of progastrin releasing peptide (ProGRP) family peptides;

(iii) has singly and/or in combination, immunogens with specificity for other gastrin-family peptides having amino acid sequences sharing similarity and/or identity to carboxy-terminal hexapeptide region SER-ALA-GLU-ASP-GLU-ASN (SEQ ID NO: 62) of Progastrin family of peptides;

(iv) has in combination, immunogens with specificity for other gastrin-family peptides having amino acid sequences sharing similarity and/or identity to unprocessed precursors of the preprohormone prohormone or such members that are partially convertase processed belonging to the Progastrin family and the Progastrin Releasing Peptide family of peptides;

(v) has in combination, immunogens with specificity for other gastrin-family peptides having amino acid sequences sharing similarity and/or identity to the proconvertase processed precursors of the preprohormone Progastrin family and Progastrin Releasing Peptide family of peptides;

(vi) immunogens engender antibodies in mammals that blocks the binding of said Gastrin Family and Gastrin Releasing Peptide Family and their precursors to their receptor and/or said binding proteins present on small cell lung cancer cells (SCLC), neuroendocrine, non-small cancer lung (NSCLC) cancer cells and other cancers, such as the GI cancers, pulmonary cancers, reproductive cancers, brain and bone and urothelial cancers.

(vii) immunogens engender antibodies in mammals that blocks the binding of said gastrin and/or gastrin-family peptides and its precursors to receptor and/or said binding proteins present on small cell lung cancer cells (SCLC), neuroendocrine, non-small cancer lung (NSCLC) cancer cells and other cancers, such as the GI cancers, pulmonary cancers, reproductive cancers, brain and bone and urothelial cancers.

In a further embodiment, the pharmaceutically acceptable carrier of the immunogenic composition may comprise an emulsion of an aqueous phase, in which said immunogen is present, and an oily phase. The oily phase may comprise at least one of squalene, squalane, sorbitan monooleate, Polysorbate 40, Polysorbate 80, and one or more of the vitamin E family of tocopherols.

Furthermore, the oily phase may comprise at least one or more emulsifier components.

In another embodiment of the invention, the immunogenic composition comprises a pharmaceutical composition wherein either said oily phase and/or said aqueous phase contains at least one adjuvant. The at least one or more suitable adjuvant(s) may be designed to stimulate the innate and adaptive immune arms by selecting individually or in combination from the group consisting of: colony-stimulating factors, optionally comprising (R)-enantiomer of Biltricide (Praziquantel), imiquimod, resimiquimod, STINGVax and/or Granulocyte Macrophage Colony Stimulating Factor (GM-CSF), 1018 ISS, aluminium salts, mixed tocopherols, cholecalciferol. Amplivax™, AS15, BCG, CP-870,893, CpG7909, CyaA, dSLIM, GM-CSF, IC30, IC31, Cyclic dinucleotides, such as cyclic diguanylate monophosphate (c-di-GMP) or other such innate immune agonists (e.g., Poly ICLC, GLA, MEDI9197, VTX2337, CpG(SD-101); Chitosan nanoparticles, ImuFact™ IMP321, IS Patch, ISCOMATRIX™, JuvImmune™, LipoVac™, MF59, monophosphoryl lipid A, Montanide™ IMS 1312, Montanide™ ISA 206, Montanide™ ISA 50V, Montanide™ ISA-51, OK-432, OM-174, OM-197-MP-EC, ONTAK®, PepTel® vector system, PLG microparticles, resiquimod, SRL172, Virosomes and other Virus-like particles, YF-17 DBCG, Aquila's QS21 stimulon, Ribi's Detox. Quil, Superfos, cholera toxin, and/or immunological adjuvants, MF59, and cytokines, as well as anti-check point antibody inhibitors (e.g., anti-PD-1L, anti-PD-L2, anti-PD-1, anti-CTLA-4) singly or in combination; The preferred immunogenic composition according to claim 1, wherein said adjuvant(s) is/are selected from the group consisting of Ergamisol, cyclic diguanylate Chitosan, Praziquantel, uric acid, mannan and derivatives of mannan, and vitamin D3, Nor-MDP, imiquimod, cyclic diguanylate, threonyl- N-acetyl-muramyl-L-alanyl-D-isoglutamine, Isoprinosine, trehalose dimycolate, QS-21, alpha-galactosylceramide, and alpha-glucosylceramide.

The immunogen(s) according to the invention is/are used with non-immunosuppressive chemotherapeutics that are selected from the group consisting of (but not limited to): cyclophosphamides, anthracyclins; doxorubicin, platinums; cisplatins, thalidomides; revlimid, fluropyrimidines; pemetrexed etc. (i.e., capable of inducing immune cell death in malignant cells, L. Galluzzi et., al., *Nature Reviews Immunology* 17, pp. 97-111 (2017)).

The pharmaceutical composition according to invention may comprise a nano-sized (i.e., less than 1 micron) emulsified immunogen that is capable of being administered intramuscularly, intradermally, intratumorally, orally, dermally, nasally, buccally, rectally, intravenously, intra-arterially, intra-peritoneally, vaginally, by inhalation, and/or by topical administration.

In yet another aspect of the invention, the pharmaceutical immunogenic composition may be used in the treatment and/or prevention of a cancer. The cancer is preferably, small cell lung cancer (SCLC), non-small-cell lung cancer (NSCLC), bronchogenic large-cell lung carcinoma (LCLC), squamous cell carcinomas or carcinomatous, gastric cancers, prostate cancer, colon cancer, pancreatic cancers, pancreato-biliary ductal adenocarcinoma, breast, ovarian cancer, urothelial, brain, bone or hepatocellular carcinoma, or malignant solid tumors of the GI tract, lung, reproductive organs and/or metastasis thereof. A third aspect of the invention provides a method for treatment and/or preventing a cancer in a patient comprising administering to the patient a therapeutically effective amount of said nano-emulsified immunogenic pharmaceutical composition of claim 1, either alone or in combination with standard of care chemotherapeutic agents and/or radiation therapeutics at full strength or metronomically at lower dosages.

In a further embodiment, the nano-emulsified immunogenic pharmaceutical composition can be used in the method as an anti-cancer vaccine treatment designed to reduce initial and/or recurrent malignant disease.

The cancer is preferably, small cell lung cancer (SCLC), non-small-cell lung cancer (NSCLC), bronchogenic large-cell lung carcinoma (LCLC), squamous cell carcinomas or carcinomatous, gastric cancers, prostate cancer, colon cancer, pancreatic cancers, pancreato-biliary ductal adenocarcinoma, breast, ovarian cancer, urothelial, brain, bone or hepatocellular carcinoma, or malignant solid tumors of the GI tract, lung, reproductive organs and/or metastasis thereof.

In further embodiments of the invention said cancers are of pulmonary or gastro-intestinal origin disseminated into lung, liver or peritoneum or said cancers are of pulmonary, reproductive or urothelial origin disseminated into brain, bone or mesothelium.

It is contemplated that said immunogen may be used with non-immunosuppressive and/or targeted chemotherapeutics that are selected from the group consisting of (but not limited to): kinase inhibitors, receptor tyrosine kinase inhibitors, cyclophosphamides, anthracyclins; doxorubicin, folate inhibitors, taxols, abraxane, platinums; oxaliplatin, cisplatins, thalidomides; revlimid, fluropyrimidines; oral fluoropyridimines pemetrexed etc. (i.e., those FDA approved chemotherapies capable of inducing immune cell death in malignant cells);complementary FDA approved monoclonal antibodies that do not interfere with immunogen induced antibody titers.

The pharmaceutical composition according to the invention may further comprise a vaccine-like agent or immunogen that is emulsified with particulates (alum adjuvants, calcium polyphosphates, nanoparticulated chitosan) suspensions, capable of being administered intramuscularly, intradermally, intratumorally, orally, dermally, nasally, buccally, rectally, intravenously, intra-arterially, intra-peritoneally, vaginally, by inhalation, and/or by topical administration.

The method for treating and/or preventing a cancer in a patient may comprise administering to the patient a therapeutically effective amount of an immunogenic pharmaceutical composition described herein, either alone or in combination with standard of care FDA approved chemotherapeutic agents and/or combined with radiation therapeutics.

Further, said immunogenic pharmaceutical composition can be an anti-cancer therapeutic or prophylactic vaccine treatment.

In the method for treating and/or preventing a cancer in a patient, the cancer is preferably, small cell lung cancer (SCLC), non-small-cell lung cancer (NSCLC), bronchogenic large-cell lung carcinoma (LCLC), squamous cell carcinomas or carcinomatous, gastric cancers, prostate cancer, colon cancer, pancreatic cancers, pancreato-biliary ductal adenocarcinoma, ovarian cancer, hepatocellular carcinoma, brain, bone, urothelial and/or malignant solid tumors of the lung and/or metastasis of the stated cancers thereof.

Further, said cancers are of haematogenous or lymphatic malignancies; in conjunction with FDA standard of care chemotherapeutics at standard or metronomic lower dosages or FDA approved targeted therapeutics.

SEQUENCES

To be written N-terminus→C-terminus sequence (where lower case letters, is to designate the pro=D isomer of Proline, and all upper case letters designate the L isomer of the amino acids in one and three letter codes (cf. www.fao.org/docrep/004/Y2775E/y2775e0e.htm)

GRP & Gastrin Family Sequences

1. CppppSSQPKALGNQQPSWDSEDSSNFKD (SEQ ID NO: 1) ProGRP[1,2,3] Onka 5a
29 amino acids;
Cys-pro-pro-pro-pro-Ser-Ser-Gln-Pro-Lys-Ala-Leu-Gly-Asn-Gln-Gln-Pro-Ser-Trp-Asp-Ser-Glu-Asp-Ser-Ser-Asn-Phe-Lys-Asp// (SEQ ID NO: 1)

| GRP & Gastrin Family Sequences |
|---|
| 2. CpppPSSQPKALGNQQPSWDSEDSSNFKD (SEQ ID NO: 2) ProGRP[1,2,3] Onka 5b<br>29 amino acids;<br>Cys-pro-pro-pro-Pro-Ser-Ser-Gln-Pro-Lys-Ala-Leu-Gly-Asn-Gln-Gln-Pro-Ser-Trp-Asp-<br>Ser-Glu-Asp-Ser-Ser-Asn-Phe-Lys-Asp// (SEQ ID NO: 2)<br><br>3. CppPPSSQPKALGNQQPSWDSEDSSNFKD ProGRP[1,2,3] Onka 5c<br>29 amino acids;<br>Cys-pro-pro-Pro-Pro-Ser-Ser-Gln-Pro-Lys-Ala-Leu-Gly-Asn-Gln-Gln-Pro-Ser-Trp-Asp-<br>Ser-Glu-Asp-Ser-Ser-Asn-Phe-Lys-Asp// (SEQ ID NO: 3)<br><br>4. CpPPPSSQPKALGNQQPSWDSEDSSNFKD (SEQ ID NO: 4) ProGRP[1,2,3] Onka 5d<br>Cys-pro-Pro-Pro-Pro-Ser-Ser-Gln-Pro-Lys-Ala-Leu-Gly-Asn-Gln-Gln-Pro-Ser-Trp-Asp-<br>Ser-Glu-Asp-Ser-Ser-Asn-Phe-Lys-Asp// (SEQ ID NO: 4)<br><br>5. SSQPKALGNQQPSWDSEDSSNFKDSSpppC (SEQ ID NO: 5) ProGRP[1,2,3] Onka 5e<br>29 amino acids;<br>Gln-Pro-Lys-Ala-Leu-Gly-Asn-Gln-Gln-Pro-Ser-Trp-Asp-Ser-Glu-Asp-Ser-Ser-Asn-<br>Phe-Lys-Asp-Ser-Ser-pro-pro-pro-pro-Cys// (SEQ ID NO: 41)<br><br>6. QPKALGNQQPSWDSEDSSNFKDSSPpppC (SEQ ID NO: 6) ProGRP[1,2,3] Onka 5f<br>29 amino acids;<br>Gln-Pro-Lys-Ala-Leu-Gly-Asn-Gln-Gln-Pro-Ser-Trp-Asp-Ser-Glu-Asp-Ser-Ser-Asn-<br>Phe-Lys-Asp-Ser-Ser-Pro-pro-pro-pro-Cys// (SEQ ID NO: 6)<br><br>7. QPKALGNQQPSWDSEDSSNFKDSSPPppC (SEQ ID NO: 7) ProGRP[1,2,3] Onka 5g<br>29 amino acids;<br>Gln-Pro-Lys-Ala-Leu-Gly-Asn-Gln-Gln-Pro-Ser-Trp-Asp-Ser-Glu-Asp-Ser-Ser-Asn-<br>Phe-Lys-Asp- Pro-Pro-pro-pro-Cys// (SEQ ID NO: 45)<br><br>8. QPKALGNQQPSWDSEDSSNFKDSSPPPpC (SEQ ID NO: 8) ProGRP[1,2,3] Onka 5h<br>29 amino acids;<br>Gln-Pro-Lys-Ala-Leu-Gly-Asn-Gln-Gln-Pro-Ser-Trp-Asp-Ser-Glu-Asp-Ser-Ser-Asn-<br>Phe-Lys-Asp-Ser-Ser-Pro-Pro-Pro-pro-Cys// (SEQ ID NO: 8)<br><br>9. CppppSSYPRGNHWAVGHLM (SEQ ID NO: 9)-NH2 (AMIDE)* GRP Onko-7a<br>20 amino acids;<br>CYS-pro-pro-pro-pro-SER-SER-TYR-PRO-ARG-GLY-ASN-HIS-TRP-ALA-VAL-<br>GLY-HIS-LEU-MET-NH2// (SEQ ID NO: 9)<br><br>10. CpppPSSYPRGNHWAVGHLM-NH2 (AMIDE)* (SEQ ID NO: 10) GRP Onko-7b<br>20 amino acids;<br>CYS-pro-pro-pro-PRO-SER-SER-TYR-PRO-ARG-GLY-ASN-HIS-TRP-ALA-VAL-<br>GLY-HIS-LEU-MET-NH$_2$// (SEQ ID NO: 10)<br><br>11. CppPPSSYPRGNHWAVGHLM-NH2 (AMIDE)* (SEQ ID NO: 11) GRP Onko-7c<br>20 amino acids;<br>CYS-pro-pro-Pro-Pro-SER-SER-TYR-PRO-ARG-GLY-ASN-HIS-TRP-ALA-VAL-<br>GLY-HIS-LEU-MET-NH$_2$// (SEQ ID NO: 11)<br><br>12. CpPPPSSYPRGNHWAVGHLM-NH2 (AMIDE)* (SEQ ID NO: 12) GRP Onko-7d<br>20 amino acids;<br>CYS-pro-Pro-Pro-Pro-SER-SER-TYR-PRO-ARG-GLY-ASN-HIS-TRP-ALA-VAL-<br>GLY-HIS-LEU-MET-NH$_2$// (SEQ ID NO: 12)<br><br>13. CppppSS**F\*PRGNHWAVGHLM**-NH2 (AMIDE)* (SEQ ID NO: 13) GRP Onko-7e<br>20 amino acids;<br>CYS-pro-pro-pro-pro-SER-SER-nPhe-PRO-ARG-GLY-ASN-HIS-TRP-ALA-VAL-<br>GLY-HIS-LEU-MET-NH$_2$// (SEQ ID NO: 13)<br><br>14. CppppSSGTVLTKMYPRGNHWAVGHL (SEQ ID NO: 14) GRP Onko-7f<br>26 amino acids;<br>CYS-pro-pro-pro-pro-SER-SER-GLY-THR-VAL-LEU-THR-LYS-MET-TYR-PRO-<br>ARG-GLY-ASN-HIS-TRP-ALA-VAL-GLY-HIS-LEU// (SEQ ID NO: 14)<br><br>15. CppppSSAGGGTVLTKMYPRGNHWAVGHL (SEQ ID NO: 15) GRP Onko-7g<br>29 amino acids;<br>CYS-pro-pro-pro-pro-SER-SER-ALA-GLY-GLY-GLY-THR-VAL-LEU-THR-LYS-<br>MET-TYR-PRO-ARG-GLY-ASN-HIS-TRP-ALA-VAL-GLY-HIS-LEU// (SEQ ID NO: 15)<br><br>16. Cp\*p\*p\*p\*SSAGGGTVLTKMYPRGNHWAVGHL (SEQ ID NO: 16) GRP Onko-7h<br>29 amino acids;<br>CYS-hPRO-hPRO-hPRO-hPRO-SER-SER-ALA-GLY-GLY-GLY-THR-VAL-LEU-<br>THR-LYS-MET-TYR-PRO-ARG-GLY-ASN-HIS-TRP-ALA-VAL-GLY-HIS-LEU//<br>(SEQ ID NO: 16) |

GRP & Gastrin Family Sequences

17. CppppSSVPLPAGGGTVLTKMYPRGNH (SEQ ID NO: 17) GRP Onko-7i
27 amino acids;
CYS-pro-pro-pro-pro-SER-SER-VAL-PRO-LEU-PRO-ALA-GLY-GLY-GLY-THR-VAL-LEU-THR-LYS-MET-TYR-PRO-ARG-GLY-ASN-HIS// (SEQ ID NO: 17)

18. CppppSS**AF*GWMDFGrRSAEDEN** (SEQ ID NO: 18) Onko-1a
23 amino acids;
CYS-pro-pro-pro-pro-SER-SER-ALA-nPHE-GLY-TRP-MET-ASP-PHE-GLY-arg-ARG-SER-ALA-GLU-ASP-GLU-ASN// (SEQ ID NO: 18)

19. CpppPSS**AF*GWMDFGrRSAEDEN** (SEQ ID NO: 19) Onka-1b
23 amino acids;
CYS-pro-pro-pro-PRO-SER-SER-ALA-nPHE-GLY-TRP-MET-ASP-PHE-GLY-arg-ARG-SER-ALA-GLU-ASP-GLU-ASN// (SEQ ID NO: 19)

20. CppPPSS**AF*GWMDFGRRSAEDEN** (SEQ ID NO: 20) Onko-1c
23 amino acids;
CYS-pro-pro-PRO-PRO-SER-SER-ALA-nPHE-GLY-TRP-MET-ASP-PHE-GLY-arg-ARG-SER-ALA-GLU-ASP-GLU-ASN// (SEQ ID NO: 20)

21. CpPPPGT**AF*GWMDFGrRSAEDEN** (SEQ ID NO: 21) Onko-1d
23 amino acids;
CYS-pro-PRO-PRO-PRO-GLY-THR-ALA-NPHE-GLY-TRP-MET-ASP-PHE-GLY-arg-ARG-SER-ALA-GLU-ASP-GLU-ASN// (SEQ ID NO: 21)

22. CP*P*P*P*SS**AF*GWMDFGrRSAEDEN** (SEQ ID NO: 22) Onko-1e
23 amino acids;
CYS-hPRO-hPRO-hPRO-hPRO-SER-SER-ALA-nPHE-GLY-TRP-MET-ASP-PHE-GLY-arg-ARG-SER-ALA-GLU-ASP-GLU-ASN// (SEQ ID NO: 22)

23. pyroEGPWIEEEEEAYSSppppC (SEQ ID NO: 23) Onko-2a
19 amino acids;
pyroGLU-GLY-PRO-TRP-ILE-GLU-GLU-GLU-GLU-GLU-ALA-TYR-SER-SER-pro-pro-pro-pro-CYS// (SEQ ID NO: 23)

24. pyroEGPWLEEEEEAF*GSppppC (SEQ ID NO: 24) Onko-2b
19 amino acids;
pyroGLU-GLY-PRO-TRP-LEU-GLU-GLU-GLU-GLU-GLU-ALA-nPHE-GLY-SER-pro-pro-pro-pro-CYS// (SEQ ID NO: 24)

25. pyroEGPWLEEEEEAF*GSPpppC (SEQ ID NO: 25) Onko-2c
19 amino acids;
pyroGLU-GLY-PRO-TRP-LEU-GLU-GLU-GLU-GLU-GLU-ALA-nPHE-GLY-SER-PRO-pro-pro-pro-CYS// (SEQ ID NO: 25)

26. pyroEGPWLEEEEEAF*GSPPppC (SEQ ID NO: 26) Onko-2d
19 amino acids;
pyroGLU-GLY-PRO-TRP-LEU-GLU-GLU-GLU-GLU-GLU-ALA-nPHE-GLY-SER-PRO-PRO-pro-pro-CYS// (SEQ ID NO: 26)

27. pyroEGPWIEEEEEAF*GSPPPpC (SEQ ID NO: 27) Onko-2e
19 amino acids;
pyroGLU-GLY-PRO-TRP-ILE-GLU-GLU-GLU-GLU-GLU-ALA-nPHE-GLY-SER-PRO-PRO-PRO-pro-CYS// (SEQ ID NO: 27)

28. CppppSS**EEEEEAF*GWMDFGrRSAEDEN** (SEQ ID NO: 51) Onko-1f
28 amino acids;
CYS-pro-pro-pro-pro-SER-SER-GLU-GLU-GLU-GLU-GLU-ALA-nPHE-GLY-TRP-MET-ASP-PHE-GLY-arg-ARG-SER-ALA-GLU-ASP-GLU-ASN// (SEQ ID NO: 51)

29. CpppPSS**EEEEEAF*GWMDFGrRSAEDEN** (SEQ ID NO: 52) Onko-1g
28 amino acids;
Cys-pro-pro-pro-PRO-SER-SER--GLU-GLU-GLU-GLU-GLU-ALA-nPHE-GLY-TRP-MET-ASP-PHE-GLY-arg-ARG-SER-ALA-GLU-ASP-GLU-ASN// (SEQ ID NO: 52)

30. CppPPSS**EEEEEAF*GWMDFGrRSAEDEN** (SEQ ID NO: 53) Onko-1h
28 amino acids;
Cys-pro-pro-PRO-PRO-SER-SER-GLU-GLU-GLU-GLU-GLU-ALA-nPHE-GLY-TRP-MET-ASP-PHE-GLY-arg-ARG-SER-ALA-GLU-ASP-GLU-ASN// (SEQ ID NO: 53)

31. CpPPPSS**EEEEEAF*GWMDFGrRSAEDEN** (SEQ ID NO: 54) Onko-1i
28 amino acids;
Cys-pro-PRO-PRO-PRO-SER-SER-GLU-GLU-GLU-GLU-GLU-ALA-nPHE-GLY-TRP-MET-ASP-PHE-GLY-arg-ARG-SER-ALA-GLU-ASP-GLU-ASN//
(SEQ ID NO: 54)

-continued

| GRP & Gastrin Family Sequences |
|---|

32. CPPPPSS**EEEEEAF\*GWMDFGrRSAEDEN** (SEQ ID NO: 55) Onko-1j
28 amino acids;
CYS-PRO-PRO-PRO-PRO-SER-SER-GLU-GLU-GLU-GLU-GLU-ALA-nPHE-GLY-
TRP-MET-ASP-PHE-GLY-arg-ARG-SER-ALA-GLU-ASP-GLU-ASN//
(SEQ ID NO: 55)

33. CppppSSPRSQQPDAPLGTGANR (SEQ ID NO: 33) Onko-1k
23 amino acids;
CYS-pro-pro-pro-pro-SER-SER-PRO-ARG-SER-GLN-GLN-PRO-ASP-ALA-PRO-
LEU-GLY-THR-GLY-ALA-ASN-ARG// (SEQ ID NO: 33)

34. PRSQQPDAPLGTGANRSSppppC (SEQ ID NO: 34) Onko-1L
23 amino acids;
PRO-ARG-SER-GLN-GLN-PRO-ASP-ALA-PRO-LEU-GLY-THR-GLY-ALA-ASN-
ARG-SER-SER-pro-pro-pro-pro-CYS// (SEQ ID NO: 34)

35. CppppSSASWKPRSQQPDAPLGTGANR (SEQ ID NO: 35)Onko-1m
27 amino acids;
CYS-pro-pro-pro-pro-SER-SER-ALA-SER-TRP-LYS-PRO-ARG-SER-GLN-GLN-
PRO-ASP-ALA-PRO-LEU-GLY-THR-GLY-ALA-ASN-ARG// (SEQ ID NO: 35)

36. ASWKPRSQQPDAPLGTGANRSSppppC (SEQ ID NO: 36) Onko-1n
27 amino acids;
ALA-SER-TRP-LYS-PRO-ARG-SER-GLN-GLN-PRO-ASP-ALA-PRO-LEU-GLY-
THR-GLY-ALA-ASN-ARGSER-SER-pro-pro-pro-pro-CYS// (SEQ ID NO: 36)

37. CppppSSGTGANRDLELPWLEQ (SEQ ID NO: 37) Onko-1o
22 amino acids;
Cys-pro-pro-pro-pro-SER-SER-GLY-THR-GLY-ALA-ASN-ARG-ASP-LEU-GLU-
LEU-PRO-TRP-LEU-GLU-GLN// (SEQ ID NO: 37)

38. GTGANRDLELPWLEQSSppppC (SEQ ID NO: 38) Onko-1p
22 amino acids;
GLY-THR-GLY-ALA-ASN-ARG-ASP-LEU-GLU-LEU-PRO-TRP-LEU-GLU-GLN
SER-SER-pro-pro-pro-pro-CYS// (SEQ ID NO: 38)

39. pyro**EGPWLEEEEEAF\*G**SSPPPpC (SEQ ID NO: 39) Onko-2f
20 amino acids;
pyroGLU-GLY-PRO-TRP-LEU-GLU-GLU-GLU-GLU-GLU-ALA-nPHE-GLY-SER-
SER-PRO-PRO-PRO-pro-CYS// (SEQ ID NO: 39)

40. CpppppprRSAEDEN (SEQ ID NO: 40)Onko-1
15 amino acids;
CYS-pro-pro-pro-pro-pro-pro-arg-ARG-SER-ALA-GLU-ASP-GLU-ASN//
(SEQ ID NO: 40)

Where:
Substituted Amino acids Met-NH2 = methionine amide
Substituted Amino acids (F\*) nPhe = L-nitrophenylalanine
Substituted Amino acids (P\*) hPro = L-hydroxyproline
Substituted Amino acids (pyroE) pyro-Glu = L-pyroglutamic acid

BRIEF DESCRIPTION OF THE FIGURES

FIG. 1B) Onko-5e-TT; FIG. 1C) Onko-7a-TT; and FIG. 1D)Onko-7e-TT FIG. 2A to FIG. 2E depicts antibody responses and kinetics in mice as measured by ELISA and are in response to three immunizations with immunogens comprising each of the conjugates FIG. 2A) Onko-5d-TT.

DETAILED DESCRIPTION OF THE INVENTION

Figure 1A:
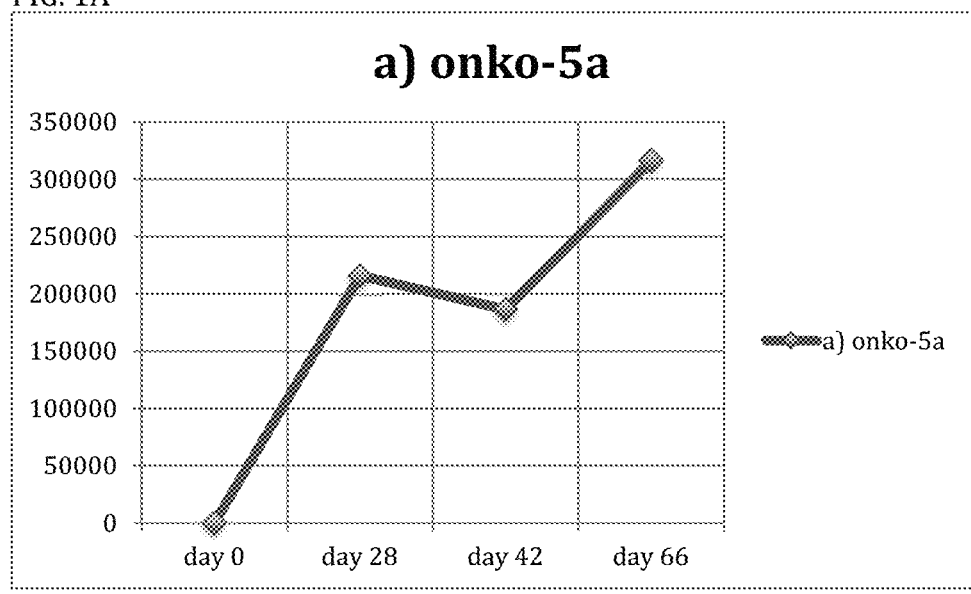
FIG. 1A to FIG. 1D depicts antibody responses and kinetics in mice as measured by ELISA and are in response to three initial immunizations with immunogens comprising each of the 20 conjugates FIG. 1A) Onko-5a-TT.

As used herein and except as noted otherwise all terms are defined as given below. The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 20, 30, or more amino acids in length, but typically less than 100 amino acids in length.

The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 6 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus an "immunogen" within the present invention), if it is capable of inducing an immune response. In the case of the present invention, immunogenicity is more specifically defined as the ability to induce a B and/or T-cell response. Thus, an "immunogen" would be a molecule that is capable of inducing an immune response, and in the case of the present invention, a molecule capable of inducing a B and/or T-cell response.

Immunization against specific cancer promoting growth factors and hormones are known to be useful and effective in the treatment and amelioration of certain malignant diseases and cancers, especially for lung, gastro-intestinal (GI) and reproductive types of cancer (e.g., ovarian, prostate, breast). Additionally, immunological approaches to the treatment of malignant lung, gastro-intestinal diseases have been seen also to be effective in the treatment of these as diseases in the short term. A number of approaches towards such immunological treatment have been successfully employed, most significantly the ones that use targeted humanized monoclonal antibodies (huMAbs) to block specific growth factors or their receptors. However, given the expense and difficulties of setting up manufacture and delivery of commercial huMAbs, alternative, yet effective but less expensive strategies are urgently needed especially for malignant diseases affecting large numbers of patients especially in developing countries where resources for monoclonal manufacture are limited or prohibitively expensive for the majority of the population.

For lung and GI cancers and related diseases these non-monoclonal active immunological approaches, entail using immunogens for the generation of specific polyclonal antibodies to bind to and inhibit the biological activity of disease promoting polypeptide growth factors or hormones. The antibodies required have to be specific for a particular growth factor or hormone, or hormone precursor. One or more factors or hormones can be selectively targeted to treat a particular disease. For example, the human hormone gastrin releasing peptide ("huGRP") or its precursors ("huProGRP") are involved in lung cancer stimulated proliferation as well as gastrointestinal disease processes including gastric cancer disease, by virtue of its ability to stimulate small cell lung cancer growth and also in other GRP-receptor containing cancers and hence cause increased proliferation and inhibition of apoptosis. Additionally, huGRP has been shown to stimulate the growth of some neuroendocrine non-small cell lung cancer cancers, and thus specific anti-huGRP and anti-huProGRP antibodies, which are able to block the action of huGRP and huProGRP (i.e., The huGRP family) factors can then be used to treat diseases in which huGRP family is involved. The anti-huGRP family antibodies can be administered to the patient (i.e., by passive immunization) or they can be induced in the patient by active immunization, using said immunogen formulations. Similarly, the gastrin (Gas) family has been shown to stimulate the growth of some non-small cell lung cancer cancers, and thus specific anti-huGas and anti-huProgastrin (huProG) antibodies, which are able to block the action of huGas and huProG (i.e., The human Gastrin family) factors can then be used to treat diseases in which huGRP family is involved. Moreover these immunogens can be used in combination concurrently or successively to inhibit these nearly ubiquitous anti-apoptotic and pro-mitotic inducing factors.

Active immunization against growth factors or gastrointestinal peptide hormones is accomplished by administering to the patient an immunogen that contains chemical structures that induce antibodies, which bind to the targeted growth factor or hormone. Such chemical structures are constructed as immunological peptide mimic of the targeted factor or hormone, and can be composed of any molecule that immunologically cross-reacts with the target or epitope of that target. These immunological peptide mimics (immunomimics) may inherently possess the capacity to induce antibodies, e.g., they may be immunogenic, often however, immunomimics are not inherently immunogenic, and must be linked to immunogenic carrier molecules to render the complex immunogenic.

The immunomimics are typically composed of two functional regions: an immunologically reactive peptide mimic and a set of peptide spacers. The function of the immunomimic is to induce antibodies that bind to the targeted peptide structure. Any chemical structures that immunologically cross-reacts with the unique epitopes of huGRP or huProGRP or other gastrin-family amino acid epitopes can serve as an immunomimic. In a preferred embodiment the immunomimic peptide is a fragment of huGRP which contains within it the carboxy-terminal epitope(s) of huGRP that is designed to stimulate a cross-reactive antibody that will bind to human GRP as well as other epitopes within and common to human ProGRP portion of the GRP precursor polypeptide. The "spacer" peptides portion of the immunogen serves as a linkage point through which the immunomimic is covalently attached to the carrier molecule, which is typically a larger immunogenic ("carrier") protein. The spacer residues will also affect the immune response against the epitope portion of the immunogen by properly orienting the immunomimic peptide conjugated chemically to the carrier protein.

Recently immunizations using a proprietary N-terminal nonapeptide portion of huG17 coupled via a spacer to diphtheria toxoid had been reported to successfully inhibit experimental ulcers in rats and GI human cancer xenografts in immunocompromised mice and in humans with GI cancers. A number of clinical trials using this immunogen (known as "G17DT") in patients with GI cancer were performed with significant results, but the latest U.S. Phase III Trial with this immunogen failed to reach statistical significance in the treatment of late stage pancreatic cancer. Although showing some successes in early clinical trials, the G17DT approach used did not take into account the marked heterogeneity of gastrin-family gene expression, particular in GI malignant diseases. While in normal gastric cells and tissue the most abundant secreted/circulating gastrin species are G17 and G34; in malignant disease the unprocessed precursors of the gastrin-family seem to predominate in humans. Numerous reports abound showing that these normal gastrin hormone species may, in fact, be less than 50%, or in certain cases as low as 10%-20% of the gastrin forms in circulation. The majority gastrin-family species are incompletely processed intermediates, known as progastrins that have been shown to have independent (of the "traditional" gastrin receptors) substantial growth promoting activities. Thus the antibodies raised by the G17DT would likely capture only G17 and C-terminally extended glycine-forms, and yet not capture the major circulating species of unprocessed/partly processed forms of gastrin-family peptides (progastrins, progastrin releasing peptides or related processed GRP peptides) that are abundant in the circulation of cancer patients. It was this type limitation that the immunogenic compositions of the invention seek to avoid and address by targeting both processed forms of GRP and intermediate precursor forms of proGRP found in circulation in cancer patients, along with some of the gastrin-family related peptides, (i.e., progastrins, which are being stimulated by GRP-family peptides) the former being, especially notable circulating in lung cancers. Moreover, it is known that antibody therapeutics, either by passively administered huMAbs or engendered actively by immunogens, are primarily cytostatic and of restricted cytotoxicity; thus requiring the deployment of traditional chemotherapeutics in conjunction with such immunologic antibody therapies. However, there are only limited types of chemotherapeutics that can be used, which do not inhibit immune response, and thus this combination therapy requires the use of non-immunosuppressive chemotherapeutics.

We have determined that certain specific peptide immunomimics of huGRP coupled to a specific spacer peptide are improved immunogens which result in an unexpectedly improved immune response compared to others. Additionally, the novel immunogen compositions of this present invention address the very hormones and growth stimulating peptides of the gastrin family that are being stimulated by the circulating elevated precursors of GRP, particularly notable in lung cancers, by inclusion of immunogens to interdict the circulating gastrin-family and its precursors. Thus combinations of GRP and ProG immunogens can be synergistic in the inhibition of growth factors that stimulate pulmonary as well as other aero-digestive and reproductive cancers.

Modifications in the gastrin family amino acids by including D-isomers of select residues, can be used to enhance the immunogenicity of the immunogens, even enhancing titers of stimulated antibody, while enabling the stimulation of cross-reacting antibodies to inhibit the natural amino acid containing growth stimulating peptides.

One specific improved immunogen generates polyclonal antibodies against progastrin releasing peptides (proGRP) and processed species of proGRP, and comprises a peptide identified as SEQ ID NO: 1 in the sequence listing above of the amino acid residues: CYS-pro-pro-pro-pro-SER-SER-GLN-PRO-LYS-ALA-LEU-GLY-ASN-GLN-GLN—PRO-SER-TRP-ASP-SER-GLU-ASP-SER-SER-ASN-PHE-LYS-ASP (Onko-5a)- where lowercase amino acids (in standard 3 letter code) represent D-isomer amino acids, and uppercase amino acids are the L-isomer form; SEQ ID NO.: 1 These sequences are identified as a proGRP oligopeptide immunogen moiety capable of engendering antibodies targeting isoforms I, II, and III is a 29 amino acid oligopeptide with an N-terminal 7 amino acid spacer sequences included, to be coupled to an immunogenic carrier protein, (eg., diphtheria toxoid, tetanus toxoid, pertussin pertussis toxoid, etc.) Tetanus toxoid is the preferred immunogenic carrier in this "progastrin releasing peptide" (proGRP) immunogen with indicated residues derived from internal sequences [gastrin-releasing peptide.isoform 1, preproprotein [Homo sapiens] of a 148 amino acid human preproGRP protein [Accession: NP_002082.2 GI:31542860] SEQ ID NO: 1 (Onko-5a).

Another immunogen generates polyclonal antibodies against progastrin releasing peptides (proGRP) and processed species of proGRP, and comprises a peptide identified as SEQ ID NO: 2 in the sequence listing above of the amino acid residues: CYS-pro-pro-pro-PRO-SER-SER-GLN-PRO-LYS-ALA-LEU-GLY-ASN-GLN-GLN—PRO-SER-TRP-ASP-SER-GLU-ASP-SER-SER-ASN-PHE-LYS-ASP (Onko-5b)- where lower case amino acids (in standard 3 letter code) represent D-isomer amino acids, and uppercase amino acids are the L-isomer form; SEQ ID NO.: 2 These sequences are identified as a proGRP oligopeptide immunogen moiety capable of engendering antibodies targeting isoforms I, II, and III is a 29 amino acid oligopeptide with an N-terminal 7 amino acid spacer sequences included, to be coupled to an immunogenic carrier protein, (eg., diphtheria toxoid, tetanus toxoid, pertussin (pertussis toxoid), etc.) Tetanus toxoid is the preferred immunogenic carrier in this "progastrin releasing peptide" (proGRP) immunogen with indicated residues derived from internal sequences [gastrin-releasing peptide.isoform 1, preproprotein [Homo sapiens] of a 148 amino acid human preproGRP protein [Accession: NP_02082.2 GI:31542860] SEQ ID NO: 2 (Onko-5b).

Another immunogen generates polyclonal antibodies against internal amino terminal epitopes of the processed human gastrin releasing peptide (ProGRP); it comprises a peptide identified as SEQ ID NO: 3 in the Sequence Listing, of the sequence: CYS-pro-pro-PRO—PRO-SER-SER-GLN-PRO-LYS-ALA-LEU-GLY-ASN-GLN-GLN—PRO-SER-TRP-ASP-SER-GLU-ASP-SER-SER-ASN-PHE-LYS-ASP-This sequence identified as a proGRP oligopeptide immunogen moiety with an N-terminal 7 amino acid spacer sequences included, capable of engendering antibodies targeting isoforms I, II, and III; it is a 29 amino acid oligopeptide coupled to an immunogenic carrier protein (e.g., diphtheria toxoid, tetanus toxoid, pertussin, etc. ). Tetanus toxoid is the preferred immunogenic carrier in this internal portion of huProGRP" (within residues 1-148 of the preprogastrin releasing peptide) [Accession: NP_002082.2 GI:31542860] SEQ ID NO.: 3 (Onko-5c).

The sequence identified as SEQ ID NO.: 4 in the Sequence Listing is CYS-pro-PRO—PRO—PRO-SER-SER-GLN-PRO-LYS-ALA-LEU-GLY-ASN-GLN-GLN—PRO-SER-TRP-ASP-SER-GLU-ASP-SER-SER-ASN-PHE-LYS-ASP; This sequences identified as a proGRP oligopeptide immunogen moiety with an N-terminal 7 amino acid spacer sequences included; capable of engendering antibodies targeting isoforms I, II, and III is a 29 amino acid oligopeptide coupled to an immunogenic carrier protein (e.g., diphtheria toxoid, tetanus toxoid, pertussin, etc. ) Tetanus toxoid is the preferred immunogenic carrier in this "progastrin releasing peptide" (proGRP) mimetic with indicated residues derived from the 1-148 peptide of a human preproGRP protein [Accession: NP_002082.2 G1:315428601 SEQ ID NO:4 (ONKO-5d).

The sequence identified as SEQ ID NO.: 42 in the Sequence Listing is GLN-PRO-LYS-ALA-LEU-GLY-ASN-GLN-GLN—PRO-SER-TRP-ASP-SER-GLU-ASP-SER-SER-ASN-PHE-LYS-ASP-SER-SER—PRO-SER-SER-pro-pro-pro-pro-CYS; This sequences identified as a proGRP oligopeptide immunogen moiety with a C-terminal 7 amino acid spacer sequences included, capable of engendering antibodies targeting isoforms I, II, and III is a 29 amino acid oligopeptide coupled to an immunogenic carrier protein ( amino acids are the L-isomer form; SEQ ID NO.: 13 that is coupled to an immunogenic carrier protein (e.g., diphtheria toxoid, tetanus toxoid, pertussin, etc.). Tetanus toxoid is the preferred immunogenic carrier in this "gastrin releasing peptide mimetic" (huGRP) with an included N-terminal 7 amino acid spacer with indicated residues derived from the 1-148 peptide of a human preproGRP protein [Accession: NP_002082.2 GI:31542860] SEQ ID NO: 13 (ONKO-7e).

Another peptide sequence is a portion of the human gastrin releasing peptide identified as SEQ ID NO.: 14 in the Sequence Listing, (where lower case pro=D isomer of Proline & all upper case letters=L isomer of the amino acids in three letter code.) as: CYS-pro-pro-pro-pro-SER-SER-GLY-THR-VAL-LEU-THR-LYS-MET-TYR-PRO-ARG-GLY-ASN-HIS-TRP-ALA-VAL-GLY-HIS-LEU. This sequence identified as a 26 amino acid oligopeptide moiety capable of engendering antibodies targeting internal epitopes of GRP after it is coupled to an FDA approved immunogenic carrier protein such as diphtheria toxoid, tetanus toxoid, pertussin, etc. Tetanus toxoid is the preferred immunogenic carrier in this gastrin releasing peptide (GRP) targeting immunogen with an included 7 N-terminal amino acid spacer with indicated residues derived from the 1-148 peptide of a human preproGRP protein [Acccssion: NP_002082.2 GiI:315428601 SEQ ID NO: 14 (ONKO-7f).

Another peptide sequence is a portion of the human gastrin releasing peptide identified as SEQ ID NO.: 15 in the Sequence Listing, (where lower case pro=D isomer of Proline & all upper case letters=L isomer of the amino acids in three letter code.) as: CYS-pro-pro-pro-pro-SER-SER-ALA-GLY-GLY-GLY-THR-VAL-LEU-THR-LYS-MET-TYR-PRO-ARG-GLY-ASN-HIS-TRP-ALA-VAL-GLY-HIS-LEU. This sequence identified as a 29 amino acid oligopeptide moiety capable of engendering antibodies targeting internal epitopes of GRP after it is coupled to an immunogenic carrier protein (e.g., diphtheria toxoid, tetanus toxoid, pertussin, etc.). Tetanus toxoid is the preferred immunogenic carrier in this gastrin releasing peptide (GRP) targeting immunogen with an included N-terminal 7 amino acid spacer with indicated residues derived from the 1-148 peptide of a human preproGRP protein [Accession: NP_002082. 2 GI:315428601 SEQ ID NO: 15 (ONKO-7g).

Another peptide sequence is a portion of the human gastrin releasing peptide identified as SEQ ID NO.: 16 in the Sequence Listing, (where all upper case letters are L- isomer of the amino acids in three letter code and hPRO is the hydroxylated form of L-Proline.) as: CYS-hPRO-hPRO-hPRO-hPRO-SER-SER-ALA-GLY-GLY-GLY-THR-VAL-LEU-THR-LYS-MET-TYR-PRO-ARG-GLY-ASN-HIS-TRP-ALA-VAL-GLY-HIS-LEU. This sequence identified as a 29 amino acid oligopeptide moiety capable of engendering antibodies targeting internal epitopes of GRP after it is coupled to an immunogenic carrier protein (e.g., diphtheria toxoid, tetanus toxoid, pertussin, etc.). Tetanus toxoid is the preferred immunogenic carrier in this gastrin releasing peptide (GRP) targeting immunogen mimetic with an included N-terminal 7 amino acid spacer with indicated residues derived from the 1-148 peptide of a human preproGRP protein [Accession: NP_M2082.2 GI:31542860] SEQ ID NO: 16 (ONKO-7h).

Another peptide sequence is a portion of the human gastrin releasing peptide identified as SEQ ID NO.: 17 in the Sequence Listing, (where lower case pro=D isomer of Proline & all upper case letters=L isomer of the amino acids in three letter code.) as: CYS-pro-pro-pro-pro-SER-SER-VAL-PRO-LEU-PRO-ALA-GLY-GLY-GLY-THR-VAL-LEU-THR-LYS-MET-TYR-PRO-ARG-GLY-ASN-HIS. This sequence identified as a 27 amino acid oligopeptide moiety capable of engendering antibodies targeting internal epitopes of GRP after it is coupled to an immunogenic carrier protein (e.g., diphtheria toxoid, tetanus toxoid, pertussin, etc.). Tetanus toxoid is the preferred immunogenic carrier in this gastrin releasing peptide (GRP) targeting immunogen with an included N-terminal 7-amino acid spacer with indicated residues derived from the 1-148 peptide of a human preproGRP protein [Accession: NP_002082.2 G1:31542860] SEQ ID NO: 17 (ONKO-7i).

SEQ ID NO.: 18 in the Sequence Listing, (where lower case pro and arg=D isomers of Proline Arginine respectively; all upper case letters=L isomer of the amino acids in three letter code where nPHE is a L-nitrophenylalanine mimetic residue.) as: CYS-pro-pro-pro-pro-SER-SER-ALA-nPHE-GLY-TRP-MET-ASP-PHE-GLY-arg-ARG-SER-ALA-GLU-ASP-GLU-ASN. This sequence identified as a 23 amino acid oligopeptide moiety capable of engendering antibodies targeting internal epitopes of processed Progastrin after it is coupled to an FDA approved immunogenic carrier protein such as diphtheria toxoid, tetanus toxoid, pertussin, etc. Tetanus toxoid is the preferred immunogenic carrier in this progastrin precursor peptide (ProG) targeting immunogen with an included N-terminal 7 amino acid spacer with indicated residues derived from the 1-101 peptide of a human preprogastrin protein [Accession: AAH69724.1 G31: 474809691 SEQ ID NO: 18 (ONKO-la).

SEQ ID NO.: 19 in the Sequence Listing, (where lower case pro and arg=D isomers of Proline Arginine respectively; =D isomer of Proline & all upper case letters=L isomer of the amino acids in three letter code where nPHE is a L-nitrophenylalanine mimetic residue.) as: CYS-pro-pro-pro-Pro-SER-SER-ALA-nPHE-GLY-TRP-MET-ASP-PHE-GLY-arg-ARG-SER-ALA-GLU-ASP-GLU-ASN. This sequence identified as a 23 amino acid oligopeptide moiety capable of engendering antibodies targeting internal epitopes of processed Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with an included N-terminal 7-amino acid spacer with indicated residues derived from the 1-101 peptide of a human preprogastrin protein [Accession: AA1H69724.1 GI: 47480969] SEQ ID NO: 19 (ONKO-1b).

SEQ ID NO.: 20 in the Sequence Listing, (where lower case pro and arg=D isomers of Proline Arginine respectively; =D isomer of Proline & all upper case letters=L isomer of the amino acids in three letter code where nPHE is a L-nitrophenylalanine mimetic residue.) as: CYS-pro-pro-PRO—PRO-SER-SER-ALA-nPHE-GLY-TRP-MET-ASP-PHE-GLY-arg-ARG-SER-ALA-GLU-ASP-GLU-ASN. This sequence identified as a 23 amino acid oligopeptide moiety capable of engendering antibodies targeting internal epitopes of processed Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with an included N-terminal 7 amino acid spacer with indicated residues derived from the 1-101 peptide of a human preprogastrin protein [Accession: AAH69724.1 GI: 47480969] SEQ ID NO: 20 (ONKO-1c).

SEQ ID NO.: 21 in the Sequence Listing, (where lower case pro and arg=D isomers of Proline Arginine respectively; =D isomer of Proline & all upper case letters=L isomer of the amino acids in three letter code where nPHE is a nitrophenylalanine mimetic residue.) as: CYS-pro- PRO—PRO-PRO-GLY-THR-ALA-nPHE-GLY-TRP-MET-ASP-PHE-GLY-arg-ARG-SER-ALA-GLU-ASP-GLU-ASN. This sequence identified as a 23 amino acid oligopeptide moiety capable of engendering antibodies targeting internal epitopes of processed Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with an included N-terminal 7-amino acid spacer with indicated residues derived from the 1-101 peptide of a human preprogastrin protein [Accession: AA1H69724.1 GI: 47480969] SEQ ID NO: 21 (ONKO-1d).

SEQ ID NO.: 22 in the Sequence Listing, (where all upper case letters are L isomers of the amino acids in three letter code and where nPHE is a L-nitrophenylalanine mimetic residue and hPRO is the hydroxylated form of L-Proline; lower case pro and arg=D isomers of Proline Arginine respectively; CYS-hPRO-hPRO-hPRO-hPRO-SER-SER-ALA-nPHE-GLY-TRP-MET-ASP-PHE-GLY-arg-ARG-SER-ALA-GLU-ASP-GLU-ASN. This sequence identified as a 23 amino acid oligopeptide moiety capable of engendering antibodies targeting internal epitopes of processed Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with an included N-terminal 7-amino acid spacer with indicated residues derived from the 1-101 peptide of a human preprogastrin protein [Accession: AAH69724.1GI: 474809691 SEQ ID NO: 22 (ONKO-1e).

SEQ ID NO.: 48 in the Sequence Listing, (where lower case pro=D isomer of Proline & all upper case letters=L isomer of the amino acids in three letter code where pyroGlu is the cyclic derivative of glutamine.) as: pyroGLU-GLY-PRO-TRP-ILE-GLU-GLU-GLU-GLU-GLU-ALA-TYR-GLY-SER-pro-pro-pro-pro-CYS. This sequence identified as a 19 amino acid oligopeptide moiety capable of engendering antibodies targeting internal epitopes of processed progastrin after it is coupled to an immunogenic carrier (e.g., diphtheria toxoid, tetanus toxoid, pertussin, etc.). Tetanus toxoid is the preferred immunogenic carrier in this progastrin precursor peptide (ProG) targeting immunogen with a C-terminal 6 amino acid spacer and with ProG indicated residues derived from the 1-101 peptide of a human preprogastrin protein [Accession: AA169724.1 GI: 47480969] SEQ ID NO: 48_(ONKO-2a).

SEQ ID NO.: 24 in the Sequence Listing, (where lower case pro=D isomer of Proline & all upper case letters=L isomer of the amino acids in three letter code and nPHE is a L-nitrophenyalanine mimetic and where pyroGLU is the cyclic derivative of glutamine.) as: pyroGLU-GLY-PRO-TRP-LEU-GLU-GLU-GLU-GLU-GLU-ALA-nPHE-GLY-SER-pro-pro-pro-pro-CYS. This sequence identified as a 19 amino acid oligopeptide moiety capable of engendering antibodies targeting internal epitopes of processed progastrin (ProG) after it is coupled to an immunogenic carrier protein (e.g., diphtheria toxoid, tetanus toxoid, pertussin, etc.). Tetanus toxoid is the preferred immunogenic carrier in this progastrin precursor peptide targeting immunogen with a C-terminal 6-amino acid spacer included; with (ProG) indicated residues derived from the 1-101 peptide of a human preprogastrin protein [Accession: AA1H69724.1 GI: 47480969] SEQ ID NO: 24 (ONKO-2b).

SEQ ID NO.: 25 in the Sequence Listing, (where lower case pro=D isomer of Proline & all upper case letters=L isomer of the amino acids in three letter code and nPHE is a L-nitrophenyalanine mimetic and where pyroGLU is the cyclic derivative of glutamine.) as: pyroGLU-GLY-PRO-TRP-LEU-GLU-GLU-GLU-GLU-GLU-ALA-nPHE-GLY-SER-PRO-pro-pro-pro-CYS. This sequence identified as a 19 amino acid oligopeptide moiety capable of engendering antibodies targeting internal epitopes of processed progastrin (ProG) after it is coupled to an immunogenic carrier protein (e.g., diphtheria toxoid, tetanus toxoid, pertussin, etc.). Tetanus toxoid is the preferred immunogenic carrier in this progastrin precursor peptide targeting immunogen with a C-terminal 6- amino acid spacer included; with (ProG) indicated residues derived from the 1-101 peptide of a human preprogastrin protein [Accession: AAI169724.1 GI: 47480969] SEQ ID NO: 25 (ONKO-2c).

SEQ ID NO.: 49 in the Sequence Listing, (where lower case pro=D isomer of Proline & all upper case letters=L isomer of the amino acids in three letter code and nPHE is a L-nitrophenyalanine mimetic and where pyroGLU is the cyclic derivative of glutamine.) as: pyroGLU-GLY-PRO-TRP-ILE-GLU-GLU-GLU-GLU-GLU-ALA-nPHE-GLY-SER-PRO-PRO-pro-pro-CYS.

This sequence identified as a 19 amino acid oligopeptide moiety capable of engendering antibodies targeting internal epitopes of processed progastrin (ProG) after it is coupled to an immunogenic carrier protein (e.g., diphtheria toxoid, tetanus toxoid, pertussin, etc.). Tetanus toxoid is the preferred immunogenic carrier in this progastrin precursor peptide targeting immunogen with a C-terminal 6- amino acid spacer included; with (ProG) indicated residues derived from the 1-101 peptide of a human preprogastrin protein [Accession: AAI169724.1 GI: 47480969] SEQ ID NO: 49 (ONKO-2d).

SEQ ID NO.: 27 in the Sequence Listing, (where lower case pro=D isomer of Proline & all upper case letters=L isomer of the amino acids in three letter code and nPHE is a L-nitrophenyalanine mimetic and where pyroGLU is the cyclic derivative of glutamine.) as: pyroGLU-GLY-PRO-TRP-ILE-GLU-GLU-GLU-GLU-GLU-ALA-nPHE-GLY-SER—PRO—PRO-PRO-pro-CYS. This sequence identified as a 19 amino acid oligopeptide moiety capable of engendering antibodies targeting internal epitopes of processed progastrin (ProG) after it is coupled to an immunogenic carrier protein (e.g., diphtheria toxoid, tetanus toxoid, pertussin, etc.). Tetanus toxoid is the preferred immunogenic carrier in this progastrin precursor peptide targeting immunogen with a C-terminal 6- amino acid spacer included; with (ProG) indicated residues derived from the 1-101 peptide of a human preprogastrin protein [Accession: AA1H69724.1 GI: 47480969] SEQ ID NO: 27 (ONKO-2e).

SEQ ID NO.: 51 in the Sequence Listing, (where lower case pro and arg=D isomers of Proline and Arginine, and all upper case letters=L isomer of the amino acids in three letter code.) as: CYS-pro-pro-pro-pro-SER-SER-GLU-GLU-GLU-GLU-GLU-ALA-nPHE-GLY-TRP-MET-ASP-PHE-GLY-arg-ARG-SER-ALA-GLU-ASP-GLU-ASN. This sequence identified as a 28 amino acid oligopeptide moiety capable of engendering antibodies targeting internal epitopes of Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with an N-terminal 7 amino acid spacer; with indicated ProG residues derived from the 1-101 peptide of a human preprogastrin protein [Accession: AAH69724.1 GI: 47480969] SEQ ID NO: 51 (ONKO-1f).

SEQ ID NO.: 52 in the Sequence Listing, (where lower case pro and arg=D isomers of Proline and Arginine, and all upper case letters=L isomer of the amino acids in three letter code.) as: CYS-PRO-pro-pro-pro-SER-SER-GLU-GLU-GLU-GLU-GLU-ALA-nPHE-GLY-TRP-MET-ASP-PHE-GLY-arg-ARG-SER-ALA-GLU-ASP-GLU-ASN. This sequence identified as a 28 amino acid oligopeptide moiety capable of engendering antibodies targeting internal epitopes of Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with an N-terminal 7 amino acid spacer; with indicated ProG residues derived from the 1-101 peptide of a human preprogastrin protein [Accession: AAH69724.1 GI: 47480969] SEQ ID NO: 52 (ONKO-1g).

SEQ ID NO.: 53 in the Sequence Listing, (where lower case pro and arg=D isomers of Proline and Arginine, and all upper case letters=L isomer of the amino acids in three letter code.) as: CYS-PRO-PRO-pro-pro-SER-SER-GLU-GLU-GLU-GLU-GLU-ALA-nPHE-GLY-TRP-MET-ASP-PHE-GLY-arg-ARG-SER-ALA-GLU-ASP-GLU-ASN. This sequence identified as a 28 amino acid oligopeptide moiety capable of engendering antibodies targeting internal epitopes of Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with an N-terminal 7 amino acid spacer; with indicated ProG residues derived from the 1-101 peptide of a human preprogastrin protein [Accession: AA1H69724.1 G1: 47480969] SEQ ID NO: 53 (ONKO-1h).

SEQ ID NO.: 54 in the Sequence Listing, (where lower case pro and arg=D isomers of Proline and Arginine, and all upper case letters=L isomer of the amino acids in three letter code.) as: CYS-PRO-PRO-PRO-pro-SER-SER-GLU-GLU-GLU-GLU-GLU-ALA-nPHE-GLY-TRP-MET-ASP-PHE-GLY-arg-ARG-SER-ALA-GLU-ASP-GLU-ASN. This sequence identified as a 28 amino acid oligopeptide moiety capable of engendering antibodies targeting internal epitopes of Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with an N-terminal 7 amino acid spacer; with indicated ProG residues derived from the 1-101 peptide of a human preprogastrin protein [Accession: AAH69724.1 GI: 474809691 SEQ ID NO: 54 (ONKO-li).

SEQ ID NO.: 55 in the Sequence Listing, (where lower case arg=D isomers of Proline and Arginine, and all upper case letters=L isomer of the amino acids in three letter code.) as: CYS—PRO-PRO-PRO—PRO-SER-SER-GLU-GLU-GLU-GLU-GLU-ALA-nPHE-GLY-TRP-MET-ASP-PHE-GLY-arg-ARG-SER-ALA-GLU-ASP-GLU-ASN. This sequence identified as a 28 amino acid oligopeptide moiety capable of engendering antibodies targeting internal epitopes of Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with an N-terminal 7-amino acid spacer; with indicated ProG residues derived from the 1-101 peptide of a human preprogastrin protein [Accession: AAH69724.1 GI: 47480969] SEQ ID NO: 55 (ONKO-1j).

SEQ ID NO.: 33 in the Sequence Listing, (where lower case pro=D isomer of Proline and all upper case letters=L isomer of the amino acids in three letter code.) as: CYS-pro-pro-pro-pro-SER-SER-PRO-ARG-SER-GLN-GLN-PRO-ASP-ALA-PRO-LEU-GLY-THR-GLY-ALA-ASN-ARG. This sequence identified as a 23 amino acid oligopeptide moiety capable of engendering antibodies targeting internal epitopes of Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with an N-terminal 7-amino acid spacer; with indicated ProG residues derived from the 1-101 peptide of a human preprogastrin protein [Accession: AA-169724.1 GII: 47480969] SEQ ID NO: 33 (ONKO-1k).

SEQ ID NO.: 34 in the Sequence Listing, (where lower case pro=D isomer of Proline and all upper case letters=L isomer of the amino acids in three letter code.) as: PRO-ARG-SER-GLN-GLN-PRO-ASP-ALA-PRO-LEU-GLY-THR-GLY-ALA-ASN-ARG-SER-SER-pro-pro-pro-pro-CYS. This sequence identified as a 23 amino acid oligopeptide moiety capable of engendering antibodies targeting internal epitopes of Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with a C-terminal 7-amino acid spacer; with indicated ProG residues derived from the 1-101 peptide of a human preprogastrin protein [Accession: AAH69724.1 GI: 47480969] SEQ ID NO: 34 (ONKO-1L).

SEQ ID NO.: 35 in the Sequence Listing, (where lower case pro=D isomer of Proline and all upper case letters=L isomer of the amino acids in three letter code.) as: CYS-pro-pro-pro-pro-SER-SER-ALA-SER-TRP-LYS-PRO-ARG-SER-GLN-GLN-PRO-ASP-ALA-PRO-LEU-GLY-THR-GLY-ALA-ASN-ARG. This sequence identified as a 27 amino acid oligopeptide moiety capable of engendering antibodies targeting internal epitopes of Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with an N-terminal 7-amino acid spacer; with indicated ProG residues derived from the 1-101 peptide of a human preprogastrin protein [Accession: AA[169724.1 GI: 47480969] SEQ ID NO: 35 (ONKO-1m).

SEQ ID NO.: 36 in the Sequence Listing, (where lower case pro=D isomer of Proline and all upper case letters=L isomer of the amino acids in three letter code.) as: ALA-SER-TRP-LYS-PRO-ARG-SER-GLN-GLN-PRO-ASP-ALA-PRO-LEU-GLY-THR-GLY-ALA-ASN-ARG-SER-SER-pro-pro-pro-pro-CYS. This sequence identified as a 27 amino acid oligopeptide moiety capable of engendering antibodies targeting internal epitopes of Progastrin after it is coupled to an FDA approved immunogenic carrier protein such as diphtheria toxoid, tetanus toxoid, pertussin, etc. Tetanus toxoid is the preferred immunogenic carrier in this progastrin precursor peptide (ProG) targeting immunogen with a C-terminal 7-amino acid spacer; with indicated ProG residues derived from the 1-101 peptide of a human preprogastrin protein [Accession: AAH69724.1 GI: 47480969] SEQ ID NO: 36 (ONKO-In).

SEQ ID NO.: 37 in the Sequence Listing, (where lower case pro=D isomer of Proline & all upper case letters=L isomer of the amino acids in three letter code.) as: Cys-pro-pro-pro-pro-SER-SER-GLY-THR-GLY-ALA-ASN-ARG-ASP-LEU-GLU-LEU-PRO-TRP-LEU-GLU-GLN. This sequence identified as a 22 amino acid oligopeptide moiety capable of engendering antibodies targeting internal epitopes of Progastrin after it is coupled to an immunogenic carrier protein (e.g., diphtheria toxoid, tetanus toxoid, pertussin, etc.).

Tetanus toxoid is the preferred immunogenic carrier in this progastrin precursor peptide (ProG) targeting immunogen with an N-terminal 7-amino acid spacer with indicated ProG residues derived from the 1-101 peptide of a human preprogastrin protein [Accession: AAH69724.1 GI: 474809691 SEQ ID NO: 37 (ONKO-1o).

SEQ ID NO.: 9[[38]] in the Sequence Listing, (where lower case pro=D isomer of Proline & all upper case letters=L isomer of the amino acids in three letter code.) as: SER-SER-GLY-THR-GLY-ALA-ASN-ARG-ASP-LEU-GLU-LEU-PRO-TRP-LEU-GLU-GLN-SER-SER-pro-pro-pro-pro-CYS. This sequence identified as a 22 amino acid oligopeptide moiety capable of engendering antibodies targeting internal epitopes of Progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with a C-terminal 7-amino acid spacer with indicated ProG residues derived from the 1-101 peptide of a human preprogastrin protein [Accession: AA-69724.1 G1: 47480969] SEQ ID NO: 9[[38]] (ONKO-1p).

SEQ ID NO.: 39 in the Sequence Listing, (where lower case pro=D isomer of Proline & all upper case letters=L isomer of the amino acids in three letter code and nPHE is a L-nitrophenyalanine mimetic and where pyroGlu is the cyclic derivative of glutamine.) as: pyroGLU-GLY-PRO-TRP-LEU-GLU-GLU-GLU-GLU-GLU-ALA-nPHE-GLY-SER-SER—PRO—PRO-PRO-pro-CYS. This sequence identified as a 20 amino acid oligopeptide moiety capable of engendering antibodies targeting internal epitopes of processed progastrin after it is coupled to an immunogenic carrier protein (e.g., diphtheria toxoid, tetanus toxoid, pertussin, etc.). Tetanus toxoid is the preferred immunogenic carrier in this progastrin precursor peptide (ProG) targeting immunogen with an N-terminal 7-amino acid spacer with indicated residues derived from the 1-101 peptide of a human preprogastrin protein [Accession: AAH69724.1 GI: 47480969] SEQ ID NO: 39 (ONKO-2f).

SEQ ID NO.: 40 in the Sequence Listing, (where lower case pro=D isomer of Proline and arg=D isomer of Arginine and all upper case letters=L isomer of the amino acids in three letter code.) as: CYS-pro-pro-pro-pro-pro-pro-arg-ARG-SER-ALA-ASP-GLU-ASN. This sequence identified as a 15 amino acid oligopeptide moiety capable of engendering antibodies targeting internal epitopes of Progastrin after it is coupled to an immunogenic carrier (e.g., diphtheria toxoid, tetanus toxoid, pertussin, etc.). Tetanus toxoid is the preferred immunogenic carrier in this progastrin precursor peptide (ProG) targeting immunogen with an N-terminal 6 amino acid spacer with indicated residues derived from the 1-101 peptide of a human preprogastrin protein [Accession: AA1H69724.1 G1: 47480969] SEQ ID NO: 40 (ONKO-1q).

Typically, the induction of effective antibody responses by immunization with immunomimic-carrier complexes requires two or more administrations of immunogen and takes several weeks or months for the antibody titers to rise to the desired levels. The improved immunogens of the present invention induce effective levels of antibody shortly after the administration of initial course of immunogen. Levels of antibody elicited stay elevated for several months and readily elevate to higher levels upon subsequent boosting by a single injection of immunogen. Importantly, the immunogen is necessary to be used periodically to generate therapeutic antibodies from the host as otherwise cross-reacting antibody titers decline and disappear unless immunogen is administered. This declining effect is necessary to preclude engendering autoimmunity and the continual generation of antibody in the absence of exogenous stimulation.

In the present invention, the immunogenic carrier can be any suitable, high molecular weight carrier, typically a protein or a large (i.e., greater than 6,000 Dalton) molecule of sufficient molecular complexity that can aid in engendering an immune response for a hapten or peptide sequence that is covalently linked to it. The category of suitable immunogenic carriers is exemplified by but not limited to tetanus toxoid (TT), diphtheria toxoid (DT), pertussin toxoid (PT), tuberculin pure protein derivative (PPD), or their subunit polypeptides and combinations thereof. Among these, tetanus toxoid is a preferred immunogenic carrier. The category also encompasses particulate carriers as nano-beads and carbon nano-tubes as described by Fifis et al., J. Immunol. 173:3148-54 (2004) as well as commercially available dendrimers, e.g., PAMAM and MAP dendrimers (see: Aguilar et al., J. Pept. Sci. 15: 78-88 (2009).

In the present context, the phrase "pharmaceutically acceptable vehicle" denotes a medically safe, non-toxic substance that will convey an immunogen without diminishment of its immunogenic effect. A suitable vehicle can be a liquid emulsion, as further described below, or it can be a stable particulate substance, e.g., as a pharmaceutically safe lyophilized powder or pharmaceutically acceptable silica gel or synthetic, non-infectious virus like particle (VLP). See FIELDS VIROLOGY, Vol. 1, D. M. Knipe & P. Howley (eds.), Lippincott Williams & Wilkins (2007).

For this invention, a preferred form of pharmaceutically acceptable vehicle is an emulsion of an aqueous phase, containing the polypeptide immunogen, and an oily phase. The oily phase comprises at least one biodegradable oil, immiscible with the aqueous phase, that is non-toxic in the dosage range of intended administration. The oil can be natural or synthetic, and there are a variety of such oils available that are generally recognized as meeting international regulatory norms for therapeutic use. Illustrative of such suitable oils are squalene, squalene, sorbitan monooleate, Polysorbate 40, alpha-tocopherol, and Polysorbate 80. A preferred oily phase comprises all six of these oils.

In addition; the oily phase may contain a separate emulsifier, such as aluminum monostearate or an adjuvant-active saccharide oleate or saccharide stearate ester.

In accordance with another aspect of the invention, either the oily or aqueous phase of an emulsion as described above, contains at least one adjuvant that is distinct from the immunogenic carrier component of the polypeptide immunogen. There is a wide range of known adjuvants, any one or more which may be considered for use in this invention.

Illustrative of such known adjuvants are: Imiquimod, cyclic diguanylate, threonyl- N-acetyl-muramyl-L-alanyl-D-isoglutamine, Isoprinosine, trehalose dimycolate, QS-21, Poly I-C, alpha-galactosylceramide (a-GalCer), Nor-MDP and alpha-glucosylceramide (a-GluCer). For this adjuvant role, moreover, the present invention comprehends the use of a material that, if not typically deemed an adjuvant per se, is immunostimulatory nevertheless. Exemplary of these materials are Poly IC, Ergamisol, Cimetidine, Praziquantel, uric acid, mannan and derivatives of mannan, and natural vitamin E.

Another embodiment that can be employed to retain and enhance immunogen's immunogenicity as well as to maintain required asepsis of the final compositional materials, includes a short 10 minute exposure of the peptide-conjugated immunogen to a mild solution of 3% USP hydrogen peroxide and/or 0.01M perchloric acid, followed by its removal by cassette dialysis or diafiltration.

EXAMPLES

Peptides were prepared by standard solid-state synthesis methods. Each peptide was characterized as to amino acid content and purity.

Peptides with the following amino acid sequences were synthesized: (All peptides were described using the standard 3-letter amino acid code or one letter code and were of the L-isomer conformations (in capital letters) unless designated as a lower case three letter or single letter amino acid and is thus a D-isomer amino acid residue)

[ref: en.wikipedia.org/wiki/Amino_acid].

Peptide Designation Amino Acid Sequence:

Peptide 1 comprises a 22 amino acid immunomimic of Progastrin releasing peptide GLN-PRO-LYS-ALA-LEU-GLY-ASN-GLN-GLN—PRO-SER-TRP-ASP-SER-GLU-ASP-SER-SER-ASN-PHE-LYS-ASP (SEQ ID NO: 63) preceded by the spacer sequences (CYS-pro-pro-pro-pro-SER-SER) attached to preprogastrin releasing peptide residues 100-121 to constitute (SEQ ID No.: 1). Peptide 2 comprises a 22 amino acid immunomimic of Progastrin releasing peptide GLN-PRO-LYS-ALA-LEU-GLY-ASN-GLN-GLN—PRO-SER-TRP-ASP-SER-GLU-ASP-SER-SER-ASN-PHE-LYS-ASP (SEQ ID NO: 63) preceded by the spacer sequence (CYS-pro-pro-pro-PRO-SER-SER ) attached to preprogastrin releasing peptide residues 100-121 to constitute (SEQ ID No.: 2). Peptide 3 comprises a 22 amino acid immunomimic of Progastrin releasing peptide GLN-PRO-LYS-ALA-LEU-GLY-ASN-GLN-GLN—PRO-SER-TRP-ASP-SER-GLU-ASP-SER-SER-ASN-PHE-LYS-ASP (SEQ ID NO: 63) preceded by the spacer sequence (CYS-pro-pro-PRO—PRO-SER-SER) attached to preprogastrin releasing peptide residues 100-121 to constitute (SEQ ID NO.: 3). Peptide 4 comprises a 22 amino acid immunomimic of Progastrin releasing peptide GLN-PRO-LYS-ALA-LEU-GLY-ASN-GLN-GLN—PRO-SER-TRP-ASP-SER-GLU-ASP-SER-SER-ASN-PHE-LYS-ASP (SEQ ID NO: 63) preceded by the spacer sequence (CYS-pro-PRO—PRO—PRO-SER-SER) attached to preprogastrin releasing peptide residues 100-121 to constitute (SEQ ID NO.: 4). Peptide 5 comprises a 22 amino acid immunomimic of Progastrin releasing peptide GLN-PRO-LYS-ALA-LEU-GLY-ASN-GLN-GLN—PRO-SER-TRP-ASP-SER-GLU-ASP-SER-SER-ASN-PHE-LYS-ASP (SEQ ID NO: 63) followed by the spacer sequence (SER-SER-pro-pro-pro-pro-CYS) attached to preprogastrin releasing peptide residues 100-121 to constitute (SEQ ID NO.: 41). Peptide 6 comprises a 22 amino acid immunomimic of Progastrin releasing peptide GLN-PRO-LYS-ALA-LEU-GLY-ASN-GLN-GLN—PRO-SER-TRP-ASP-SER-GLU-ASP-SER-SER-ASN-PHE-LYS-ASP (SEQ ID NO: 63) followed by the spacer sequence (SER-SER-PRO-pro-pro-pro-CYS) attached to preprogastrin releasing peptide residues 100-121 to constitute (SEQ ID NO.: 6). Peptide 7 comprises a 22 amino acid immunomimic of Progastrin releasing peptide GLN-PRO-LYS-ALA-LEU-GLY-ASN-GLN-GLN—PRO-SER-TRP-ASP-SER-GLU-ASP-SER-SER-ASN-PHE-LYS-ASP (SEQ ID NO: 63) followed by the spacer sequence (SER-SER—PRO-PRO-pro-pro-CYS) attached to preprogastrin releasing peptide residues 100-121 to constitute (SEQ ID NO.: 7). Peptide 8 comprises a 22 amino acid immunomimic of Progastrin releasing peptide GLN-PRO-LYS-ALA-LEU-GLY-ASN-GLN-GLN—PRO-SER-TRP-ASP-SER-GLU-ASP-SER-SER-ASN-PHE-LYS-ASP (SEQ ID NO: 63) followed by the spacer sequence (SER-SER—PRO-PRO-PRO-pro-CYS) attached to preprogastrin releasing peptide residues 100-121 to constitute (SEQ ID NO.: 8). Peptide 9 comprises a C-terminal amidated13 amino acid immunomimic of the processed human gastrin releasing peptide (huGRP) oligopeptide TYR-PRO-ARG-GLY-ASN-HIS-TRP-ALA-VAL-GLY-HIS-LEU-MET-NH$_2$ (SEQ ID NO: 64) preceded by the spacer sequences (CYS-pro-pro-pro-pro-SER-SER) attached at preprogastrin residue 38-50 to constitute (SEQ ID NO.: 9). Peptide 10 comprises a C-terminal amidated13 amino acid immunomimic of the processed human gastrin releasing peptide (huGRP) oligopeptide TYR-PRO-ARG-GLY-ASN-HIS-TRP-ALA-VAL-GLY-HIS-LEU-MET-NH$_2$ (SEQ ID NO: 64) preceded by the spacer sequences (CYS-pro-pro-pro-PRO-SER-SER) attached at preprogastrin residue 38-50 to constitute (SEQ ID NO.:10). Peptide 11 comprises a C-terminal amidated13 amino acid immunomimic of the processed human gastrin releasing peptide (huGRP) oligopeptide TYR-PRO-ARG-GLY-ASN-HIS-TRP-ALA-VAL-GLY-HIS-LEU-MET-NH$_2$ (SEQ ID NO: 64) preceded by the spacer sequences (CYS-pro-pro-PRO—PRO-SER-SER) attached at preprogastrin residue 38-50 to constitute (SEQ ID NO.:11). Peptide 12 comprises a C-terminal amidated13 amino acid immunomimic of the processed human gastrin releasing peptide (huGRP) oligopeptide TYR-PRO-ARG-GLY-ASN-HIS-TRP-ALA-VAL-GLY-HIS-LEU-MET-NH$_2$ (SEQ ID NO: 64) preceded by the spacer sequences (CYS-pro-PRO—PRO-PRO-SER-SER) attached at preprogastrin residue 38-50 to constitute (SEQ ID NO.:12). Peptide 13 comprises a C-terminal amidated 13 amino acid immunomimic of the processed human gastrin releasing peptide (huGRP) oligopeptide nPHE-PRO-ARG-GLY-ASN-HIS-TRP-ALA-VAL-GLY-HIS-LEU-MET-NH$_2$ (SEQ ID NO: 65) preceded by the spacer sequences (CYS-pro-PRO—PRO—PRO-SER-SER) attached at preprogastrin residue 38-50 to constitute (SEQ ID NO.:13). Peptide 14 comprises a 19 amino acid immunomimic of Progastrin releasing peptide GLY-THR-VAL-LEU-THR-LYS-MET-TYR-PRO-ARG-GLY-ASN-HIS-TRP-ALA-VAL-GLY-HIS-LEU (SEQ ID NO: 66) preceded by the spacer sequence (CYS-pro-pro-pro-pro-SER-SER) attached to preprogastrin releasing peptide residues 31-49 to constitute (SEQ ID NO.: 14). Peptide 15 comprises a 22 amino acid immunomimic of Progastrin releasing peptide ALA-GLY-GLY-GLY-THR-VAL-LEU-THR-LYS-MET-TYR-PRO-ARG-GLY-ASN-HIS-TRP-ALA-VAL-GLY-HIS-LEU (SEQ ID NO: 67) preceded by the spacer sequence (CYS-pro-pro-pro-pro-SER-SER) attached to preprogastrin releasing peptide residues 28-49 to constitute (SEQ ID NO.: 15). Peptide 16 comprises a 22 amino acid immunomimic of Progastrin releasing peptide ALA-GLY-GLY-GLY-THR-VAL-LEU-THR-LYS-MET-TYR-PRO-ARG-GLY-ASN-HIS-TRP-ALA-VAL-GLY-HIS-LEU (SEQ ID NO: 67) preceded by the spacer sequence (CYS-hPRO-hPRO-hPRO-hPRO-SER-SER (SEQ ID NO: 68)) attached to preprogastrin releasing peptide residues 28-49 to constitute (SEQ ID NO.: 16). Peptide 17 comprises a 20 amino acid immunomimic of Progastrin releasing peptide VAL-PRO-LEU-PRO-ALA-GLY-GLY-GLY-THR-VAL-LEU-THR-LYS-MET-TYR-PRO-ARG-GLY-ASN-HIS (SEQ ID NO: 69) preceded by the spacer sequence (CYS-pro-pro-pro-pro-SER-SER) attached to preprogastrin releasing peptide residues 28-49 to constitute (SEQ ID NO.: 17). Peptide 18 comprises a 16 amino acid immunomimic of Progastrin (ProG) ALA-nPHE-GLY-TRP-MET-ASP-PHE-GLY-ARG-ARG-SER-ALA-GLU-ASP-GLU-ASN (SEQ ID NO: 70) preceded by the spacer sequences (CYS-pro-pro-pro-pro-SER-SER) attached to preprogastrin residues 86-101 to constitute (SEQ ID NO.: 18). Peptide 19 comprises a 16 amino acid immunomimic of Progastrin (ProG) ALA-nPHE-GLY-TRP-MET-ASP-PHE-GLY-arg-ARG-SER-ALA-GLU-ASP-GLU-ASN preceded by the spacer sequences (CYS-pro-pro-pro-PRO-SER-SER) attached to preprogastrin residues 86-101 to constitute (SEQ ID NO.: 19). Peptide 20 comprises a 16 amino acid immunomimic of Progastrin (ProG) ALA-nPHE-GLY-TRP-MET-ASP-PHE-GLY-arg-ARG-SER-ALA-GLU-ASP-GLU-ASN preceded by the spacer sequences (CYS-pro-pro-PRO—PRO-SER-SER) attached to preprogastrin residues 86-101 to constitute (SEQ ID NO.: 20). Peptide 21 comprises a 16 amino acid immunomimic of Progastrin (ProG) ALA-nPHE-GLY-TRP-MET-ASP-PHE-GLY-arg-ARG-SER-ALA-GLU-ASP-GLU-ASN preceded by the spacer sequences (CYS-pro-PRO—PRO-PRO-SER-SER) attached to preprogastrin residues 86-101 to constitute (SEQ ID NO.: 47). Peptide 22 comprises a 16 amino acid immunomimic of Progastrin (ProG) ALA-nPHE-GLY-TRP-MET-ASP-PHE-GLY-arg-ARG-SER-ALA-GLU-ASP-GLU-ASN preceded by the spacer sequences (CYS-hPRO-hPRO-hPRO-hPRO-SER-SER (SEQ ID NO: 68)) attached to preprogastrin residues 86-101 to constitute (SEQ ID NO.: 22). Peptide 23 comprises a 13 amino acid immunomimic of a Progastrin (ProG) pyroGLU-GLY-PRO-TRP-ILE-GLU-GLU-GLU-GLU-GLU-ALA-TYR-GLY (SEQ ID NO: 71) followed by the spacer sequence (SER-pro-pro-pro-pro-CYS) attached to preprogastrin residues 76-88 to constitute (SEQ ID NO.: 48). Peptide 24 comprises a 13 amino acid immunomimic of Progastrin (ProG) pyroGLU-GLY-PRO-TRP-LEU-GLU-GLU-GLU-GLU-GLU-ALA-nPHE-GLY (SEQ ID NO: 72) followed by the spacer sequence (SER-pro-pro-pro-pro-CYS) attached to preprogastrin residues 76-88 to constitute (SEQ ID NO.: 24). Peptide 25 comprises a 13 amino acid immunomimic of Progastrin (ProG) pyroGLU-GLY-PRO-TRP-LEU-GLU-GLU-GLU-GLU-GLU-ALA-nPHE-GLY (SEQ ID NO: 72) followed by the spacer sequence (SER-PRO-pro-pro-pro-CYS) attached to preprogastrin residues 76-88 to constitute (SEQ ID NO.: 25). Peptide 26 comprises a 13 amino acid immunomimic of Progastrin (ProG) pyroGLU-GLY-PRO-TRP-LEU-GLU-GLU-GLU-GLU-GLU-ALA-nPHE-GLY (SEQ ID NO: 72) followed by the spacer sequence (SER—PRO-PRO-pro-pro-CYS) attached to preprogastrin residues 76-88 to constitute (SEQ ID NO.: 26). Peptide 27 comprises a 13 amino acid immunomimic of Progastrin (ProG) pyroGLU-GLY-PRO-TRP-LEU-GLU-GLU-GLU-GLU-GLU-ALA-nPHE-GLY (SEQ ID NO: 72) followed by the spacer sequence (SER—PRO-PRO-PRO-pro-CYS) attached to preprogastrin residues 76-88 to constitute (SEQ ID NO.: 50).

Peptide 28 comprises a 21 amino acid immunomimic of Progastrin (ProG) GLU-GLU-GLU-GLU-GLU-ALA-nPHE-GLY-TRP-MET-ASP-PHE-GLY-arg-ARG-SER-ALA-GLU-ASP-GLU-ASN preceded by the spacer sequences (CYS-pro-pro-pro-SER-SER) attached to preprogastrin residues 81-101 to constitute (SEQ ID NO.: 51).

Peptide 29 comprises a 21 amino acid immunomimic of Progastrin (ProG) GLU-GLU-GLU-GLU-GLU-ALA-nPHE-GLY-TRP-MET-ASP-PHE-GLY-arg-ARG-SER-ALA-GLU-ASP-GLU-ASN preceded by the spacer sequences (CYS-pro-pro-pro-PRO-SER-SER) attached to preprogastrin residues 81-101 to constitute (SEQ ID NO.: 52).

Peptide 30 comprises a 21 amino acid immunomimic of Progastrin (ProG) GLU-GLU-GLU-GLU-GLU-ALA-nPHE-GLY-TRP-MET-ASP-PHE-GLY-arg-ARG-SER-ALA-GLU-ASP-GLU-ASN preceded by the spacer sequences (CYS-pro-pro-PRO—PRO-SER-SER) attached to preprogastrin residues 81-101 to constitute (SEQ ID NO.: 53).

Peptide 31 comprises a 21 amino acid immunomimic of Progastrin (ProG) GLU-GLU-GLU-GLU-GLU-ALA-nPHE-GLY-TRP-MET-ASP-PHE-GLY-arg-ARG-SER-ALA-GLU-ASP-GLU-ASN preceded by the spacer sequences (CYS-pro-PRO—PRO-PRO-SER-SER) attached to preprogastrin residues 81-101 to constitute (SEQ ID NO.: 54).

Peptide 32 comprises a 21 amino acid immunomimic of Progastrin (ProG) GLU-GLU-GLU-GLU-GLU-ALA-nPHE-GLY-TRP-MET-ASP-PHE-GLY-arg-ARG-SER-ALA-GLU-ASP-GLU-ASN preceded by the spacer sequences (CYS—PRO-PRO-PRO—PRO-SER-SER (SEQ ID NO: 73)) attached to preprogastrin residues 81-101 to constitute (SEQ ID NO.: 55). Peptide 33 comprises a 16 amino acid immunomimic of Progastrin (ProG) Pro-Arg-Ser-Gln-Gln-Pro-Asp-Ala-Pro-Leu-Gly-Thr-Gly-Ala-Asn-Arg (SEQ ID NO: 74) preceded by the spacer sequences (CYS-pro-pro-pro-pro-SER-SER) attached to preprogastrin residues 25-40 to constitute (SEQ ID NO.: 57). Peptide 34 comprises a 16 amino acid immunomimic of Progastrin (ProG) PRO-ARG-SER-GLN-GLN-PRO-ASP-ALA-PRO-LEU-GLY-THR-GLY-ALA-ASN-ARG (SEQ ID NO: 74) followed by the spacer sequences (CYS-pro-pro-pro-pro-SER-SER) attached to preprogastrin residues 25-40 to constitute (SEQ ID NO.: 56). Peptide 35 comprises a 20 amino acid immunomimic of Progastrin (ProG) PRO-ARG-SER-GLN-GLN-PRO-ASP-ALA-PRO-LEU-GLY-THR-GLY-ALA-ASN-ARG (SEQ ID NO: 74) preceded by the spacer sequences (CYS-pro-pro-pro-pro-SER-SER) attached to preprogastrin residues 21-40 to constitute (SEQ ID NO.: 57). Peptide 36 comprises a 20 amino acid immunomimic of Progastrin (ProG) PRO-ARG-SER-GLN-GLN-PRO-ASP-ALA-PRO-LEU-GLY-THR-GLY-ALA-ASN-ARG (SEQ ID NO: 74) followed by the spacer sequences (CYS-pro-pro-pro-pro-SER-SER) attached to preprogastrin residues 21-40 to constitute (SEQ ID NO.: 56). Peptide 37 comprises a 13 amino acid immunomimic of Progastrin (ProG) GLY-THR-GLY-ALA-ASN-ARG-ASP-LEU-GLU-LEU-PRO-TRP-LEU-GLU-GLU-GLN (SEQ ID NO: 75) preceded by the spacer sequences (CYS-pro-pro-pro-SER-SER) attached to preprogastrin residues 35-49 to constitute (SEQ ID NO.: 37). Peptide 38 comprises a 13 amino acid immunomimic of Progastrin (ProG) GLY-THR-GLY-ALA-ASN-ARG-ASP-LEU-GLU-LEU-PRO-TRP-LEU-GLU-GLN (SEQ ID NO: 75) followed by the spacer sequences (CYS-pro-pro-pro-pro-SER-SER) attached to preprogastrin residues 35-49 to constitute (SEQ ID NO.: 58). Peptide 39 comprises a 13 amino acid immunomimic of Progastrin (ProG) PyroGLU-GLY-PRO-TRP-LEU-GLU-GLU-GLU-GLU-GLU-ALA-nPHE-GLY-(SEQ ID NO: 72) followed by the spacer sequences (CYS-pro-pro-pro-pro-SER-SER) attached to preprogastrin residues 76-88 to constitute (SEQ ID NO.: 60). Peptide 40 comprises a 8 amino acid immunomimic of Progastrin (ProG) arg-ARG-SER-ALA-GLU-ASP-GLU-ASN preceded by the spacer sequences (CYS-pro-pro-pro-pro-pro-pro) attached to preprogastrin residues 94-101 to constitute (SEQ ID NO.:40)in the Sequence Listing.

In accordance with a preferred aspect of the invention, each of these peptides was conjugated to amino groups present on the tetanus toxoid (TT) immunogenic carrier. The linkage was via the terminal peptide cysteine residue, utilizing heterobifunctional linking agents, employed as those skilled in the arts utilize, such as conjugating agents containing a succinimidyl ester at one end and maleimide at the other end of the linking agent. To accomplish the linkage between either of the peptides 1 through 40 of the above and the carrier, the cysteine of the peptides was first reduced. Typically the dry peptide was dissolved in 0.1 M sodium phosphate buffer, pH 7-9, with a 5-50 molar excess of dithiothreitol. The peptide was lyophilized and stored under vacuum until used.

The TT was activated by treatment with the heterobifunctional linking agent such as epsilon-maleimidocaproic acid N-hydroxysuccinimide ester (EMCS), in proportions sufficient to achieve activation of approximately 25 free amino groups per $10^5$ molecular weight of TT.

Preparation of Purified Tetanus Toxoid: TT was purified by ultra-filtration. Final concentration of recovered purified TT was expected to be 5-40 mg/ml. The purity was determined by chromatography (SEC HPLC), protein concentration (Lowry, BCA, or Bradford), and free amino- groups (ninhydrin).

Peptides were obtained commercially (Biosyn Corp, USA), and reduced peptide with known purity and content was used for conjugation. Peptides were reduced with tris (2-carboxyethyl)-phosphine-HCl (TCEP), and the mixture was used in the conjugation. Ellman's assay can be used to determine free sulfhydryl groups.

Activation of Tetanus Toxoid (TT): Dilute purified TT to 5-50 mg/ml in Activation buffer. The desired amount of TT was transferred to a glass vial containing a Teflon-coated stir bar, and EMCS (50-90 mg/ml DMF) was added to the TT solution. The molar ratio of EMCS/DT determines the activation level. In the final concentration step, the total volume was reduced to give>−5-50 mg TT/ml. The TT solution was determined by SEC HPLC, the protein concentration by Lowry, BCA or Bradford and the activation level by Ellman's.

Conjugation of Peptide-TT: After calculating the quantity of peptide to react with the maleimido-TT, the peptide was added to the M-TT solution.. The peptide-TT conjugate was purified by ultrafiltration. The conjugates of the peptides were linked to TT via EMCS and were separated from other components of the mixture by low pressure chromatography at 4° C. over a G-50 Sephadex column equilibrated with 0.1 M-0.5M ammonium bicarbonate. In each case the conjugate was eluted in the column void volume and was lyophilized and stored, desiccated, at 4-0° C. until use.

Example 1

The conjugate may be characterized as to immunomimic peptide content by a number of methods known to those skilled in the art including weight gain, amino acid analysis, etc. Conjugates of peptides Onko-5a and Onko-7a to TT produced by these methods were determined by amino acid analysis to have 10-30 moles of peptide per $10^4$-$10^6$ MW of TT and all were considered suitable as immunogens for immunization of test animals. Similarly, TT conjugates of Onko-5a and Onko-7a, were prepared in the same manner to determine ELISA titers using huGRP peptide as the substrate for assay of antibody binding.

Example 2

The peptide-TT conjugates of Example 1 were administered in emulsions of aqueous and oily phase components that were prepared as follows. The conjugate and adjuvant were dissolved in phosphate buffered saline (PBS) to produce the aqueous phase. The aqueous phase is prepared so that the concentrations of conjugate are double the concentration that these components will have in the final emulsion. In order to prepare the immunogens used in Example 4 below, the conjugate was dissolved in PBS, pH 6.5-8.0, to a concentration of 5-12 mg/ml. (Indeed it can be over this broad range, and we use it to control extent of carrier we want conjugated).

The aqueous phase was combined 1:1 (vol:vol) with the oily vehicle phase to create an emulsion that comprised the final immunogen formulation. One such vehicle is a mixture of 20-60 parts squalene, 70-30 parts 58qualene, 2-12 parts sorbitan monooleate, 0.6-2.0 parts alpha-tocopherol, 0.1-1 parts Polysorbate 80, and 0.2-1.2 parts Polysorbate 40. The aqueous phase and oily phase vehicle can be mixed by any known method for forming a stable emulsified mixture. The emulsion must be stable upon storage, i.e., it should not undergo a significant degree of separation into aqueous and vehicle phases for a minimal storage time of several weeks to months. The emulsion also must be of a consistency that allows it to be injected readily through an acceptable size of hypodermic needle. The aqueous phase containing the immunogen was emulsified 1: 1 (vol:vol) with the oily vehicle mixture of the two solutions through an 18 gauge double-coupled needle between two glass syringes. The mixture was pressed through the needle 50 times. (Larger volumes, >1L were processed with a commercial microfluidizer). The emulsified mixture then was drawn into disposable syringes for injection into animals. The final immunogen concentration in the emulsion, for in Example 4, was conjugated: Onko5a-TT ranging in concentration from about 1 to about 5 mg per milliliter.

Example 3

The inventors constructed conjugates comprising each of the Onko-5a and Onko-7a peptides listed in Example 1 linked to TT and DT, as described in Examples 1 and 2.

Figure 1B:
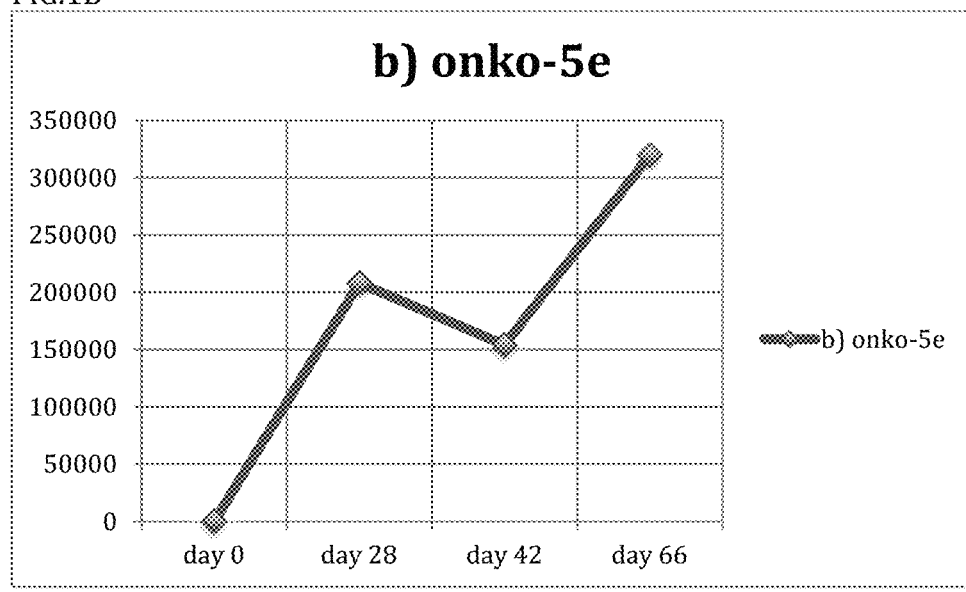
Figure 1C:
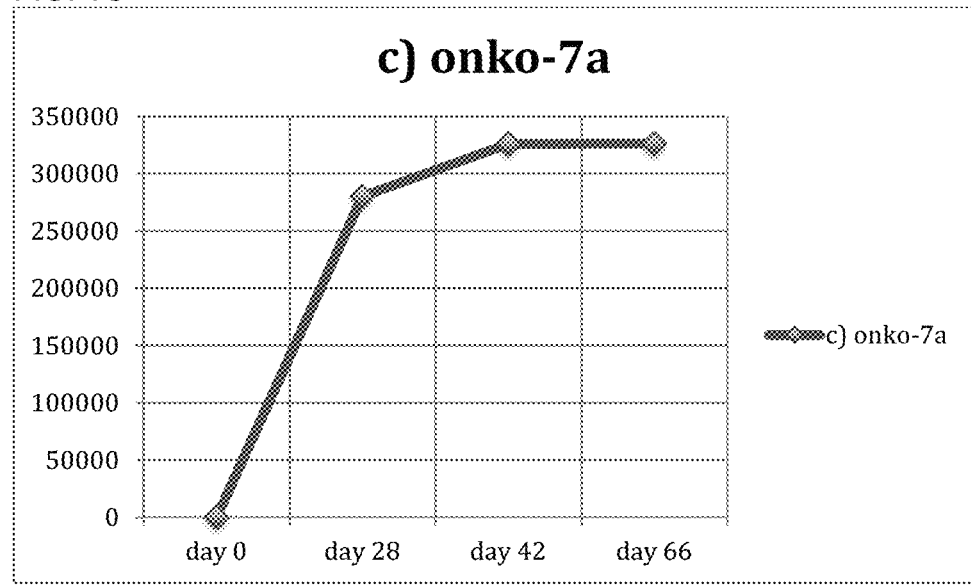
Figure 1D:
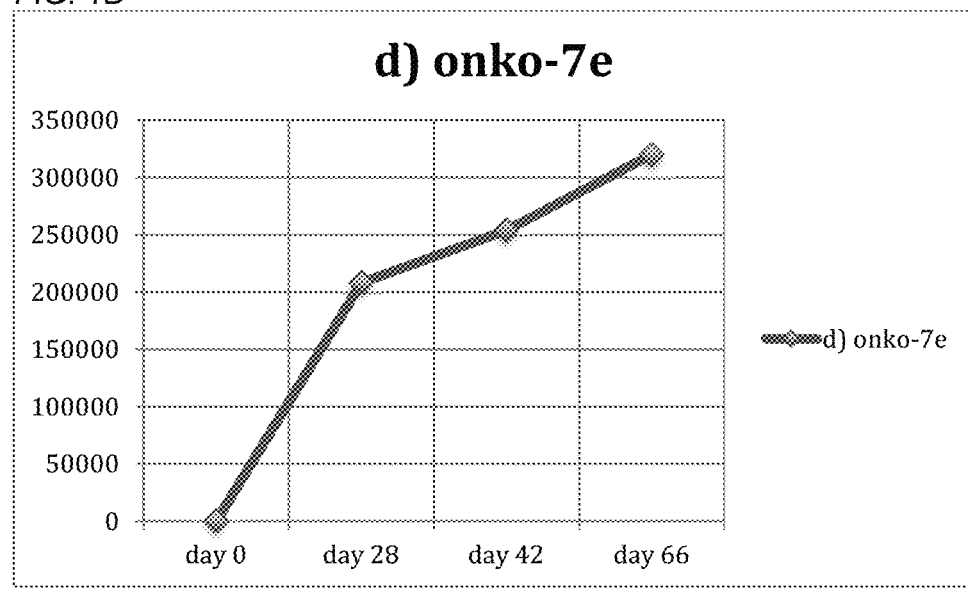

They then immunized six mice with the peptide Onko-5a immunogen (FIG. 1A and FIG. 1B) and six mice with the peptide Onko-7a immunogen (FIG. 1C and FIG. 1D).

Example 4

Figure 2A:
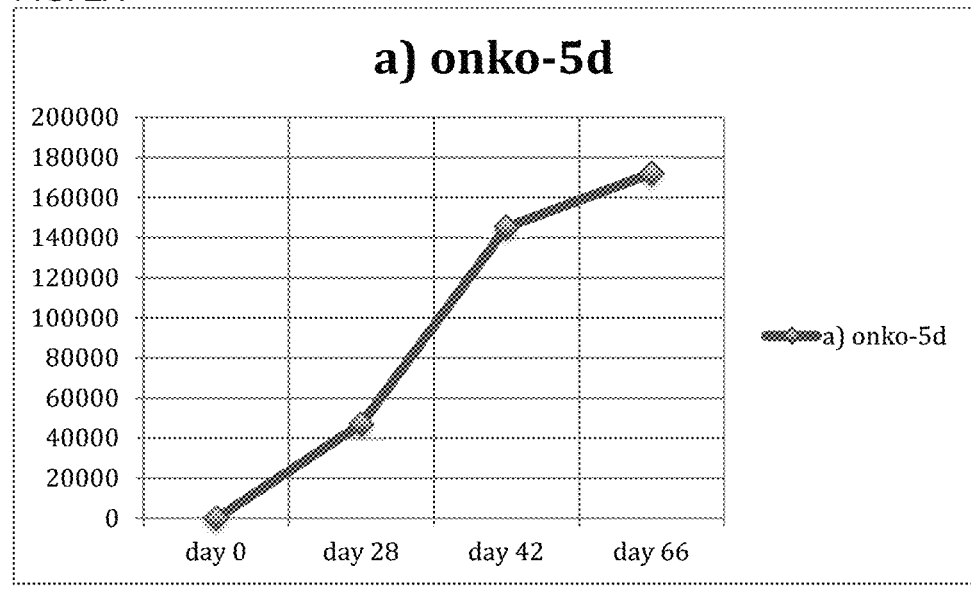
FIG. 2B) Onko-5h-TT.
FIG. 2C) Onko-7d-TT.
FIG. 2D) Onko-1a-TT.
FIG. 2E) Onko1d-TT FIG. 3A to FIG. 3B depicts antibody responses in mice and kinetics as measured by ELISA and are in responses to three immunizations with an equal immunogen mix (25 ug:25 ug) comprising both FIG. 3A) Onko5a-TT+Onko7a-TT and FIG. 3B) Onko-5d-TT+Onko7d-TT FIG. 4A to FIG. 4B depicts antibody responses and kinetics in rabbits as measured by ELISA and are in response to three immunizations with immunogens comprising each of the conjugates FIG. 4A) Onko-5a-TT.
Figure 2B:
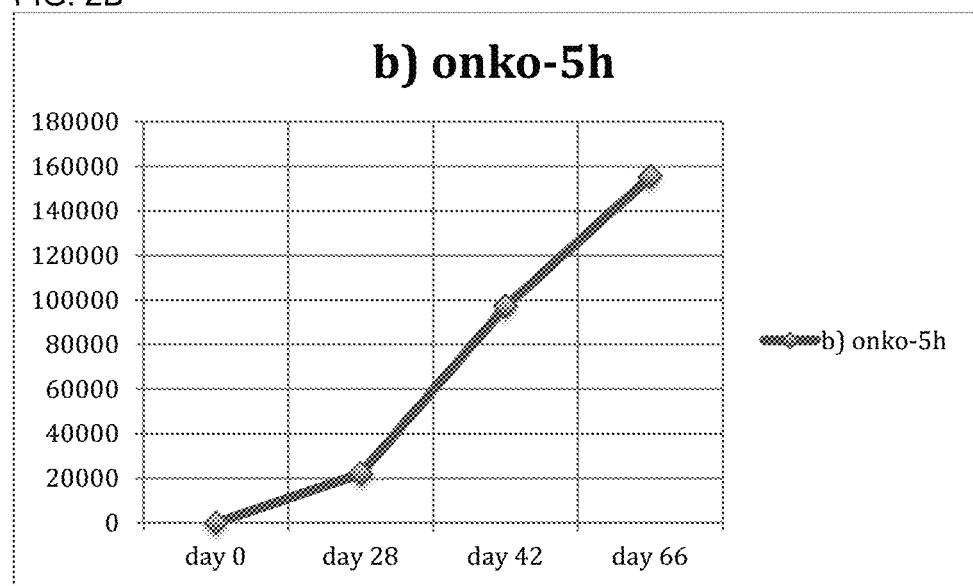
Figure 2C:
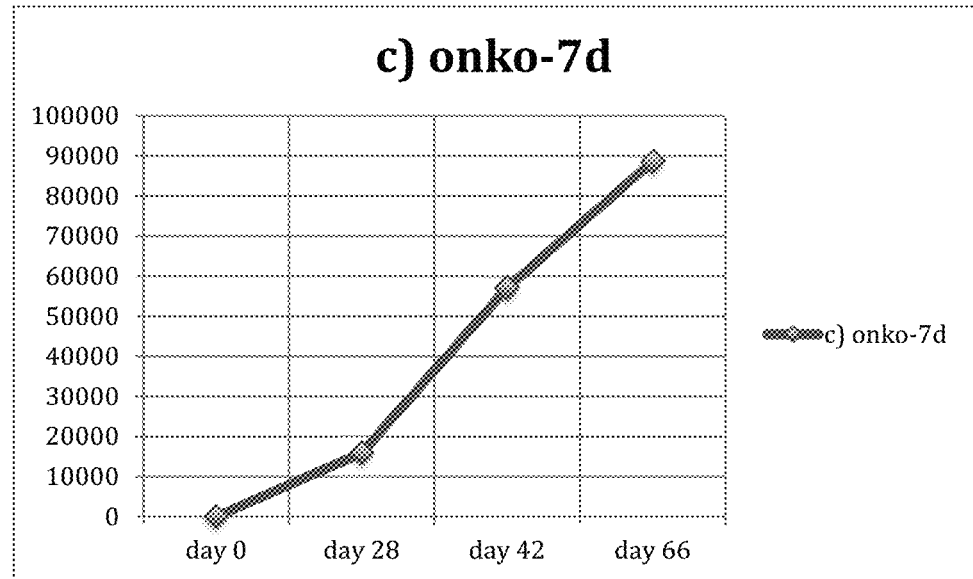
Figure 2D:
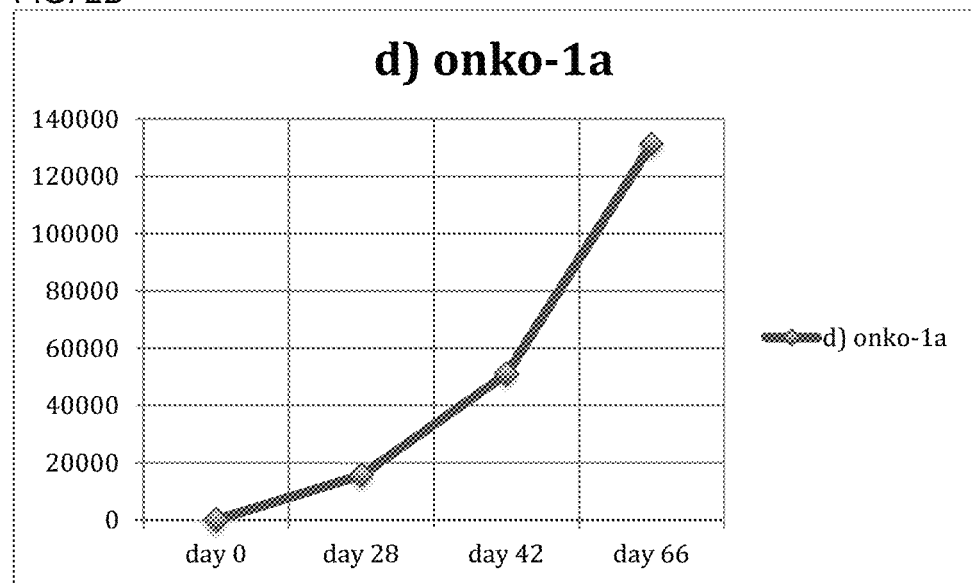
Figure 2E:
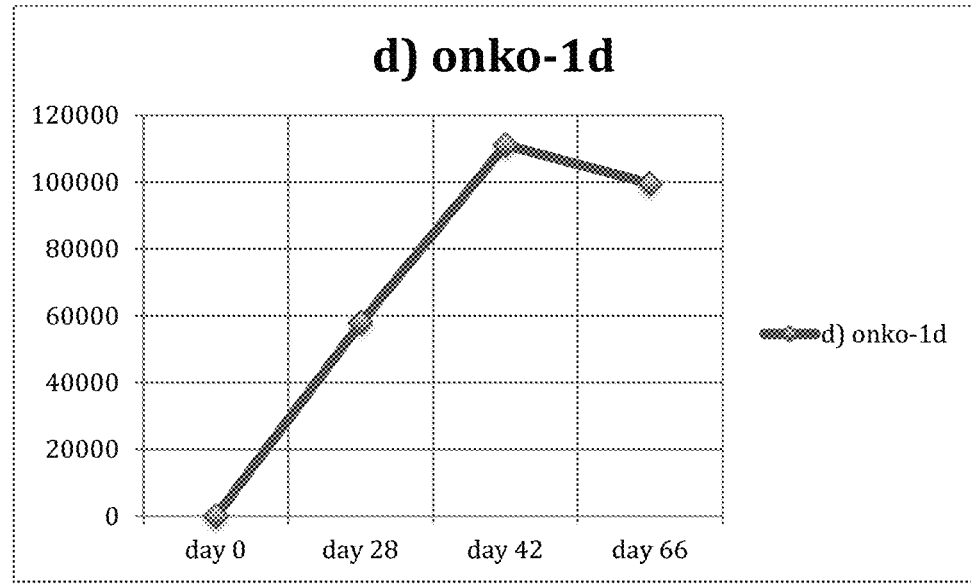

The inventors constructed conjugates comprising each of the Onko-5a and Onko-7a peptides, linked to TT as described in Examples 1 and 2. They then immunized four rabbits with theOnko-5a immunogen (FIG. 2A) and four rabbits with the Onko-7a immunogen (FIG. 2B).

The results of these ELISA tests, as presented in FIGS. 1A to 2E, show that immunogens 1 and 2 (Onko-5a and Onko-7a of Example 1 and 2) were effective in terms of both their potency and, their eliciting of antibody in several animals species, as well as in the duration of the antibody responses induced.

Example 5

The inventors constructed conjugates comprising each of the Onko-5a and Onko-7a peptides linked to TT, as described above. They then immunized six mice with the Onko-5a-TT immunogen and, the Onko-7aTT immunogen. At peak titers (Day 42) all mice received sterile, intraperitoneal hollow fiber implants containing 50,000 human gastric cancer cells/1-2 implant tube (BCG-823 cells) for 5 days in situ. Hollow fiber tubules permit penetration of <500 KD molecules but not of CTL or NK cells, enabling survival of human cancer cells in immunocompetent mice. At end of 5 days each mouse had the implants removed, and the viable cells were counted by MTT assay, comparing them to control implants in non-immunized mice. As indicated, some animals also were treated with single administrations of 10 mg/kg cisplatin (CP) or 20 mg/kg 5-fluorouracil (5-FU) or a combination of 10 mg/mg each of CP+5-FU (FUP) and at 50% lower dosages as well.

Figure 3A:
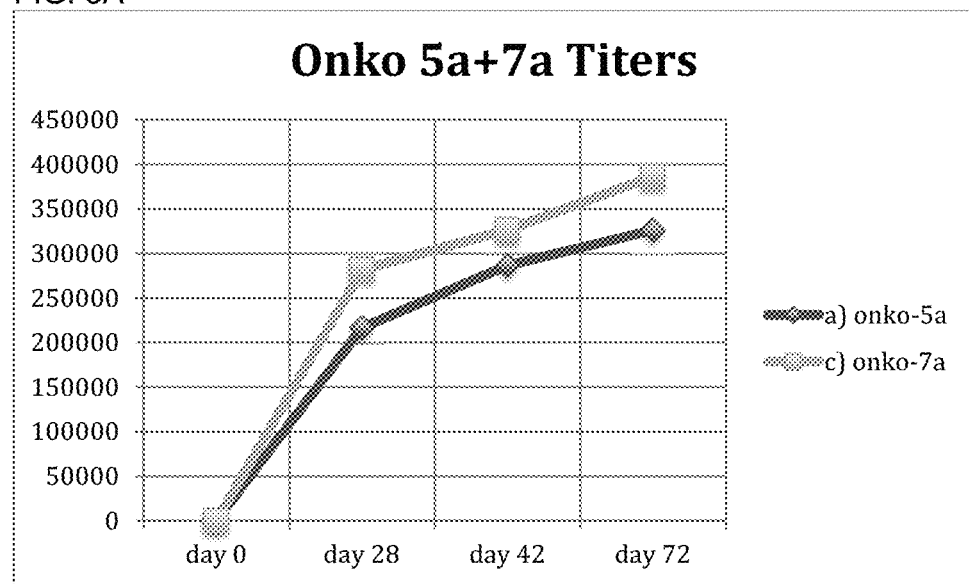
Figure 3B:
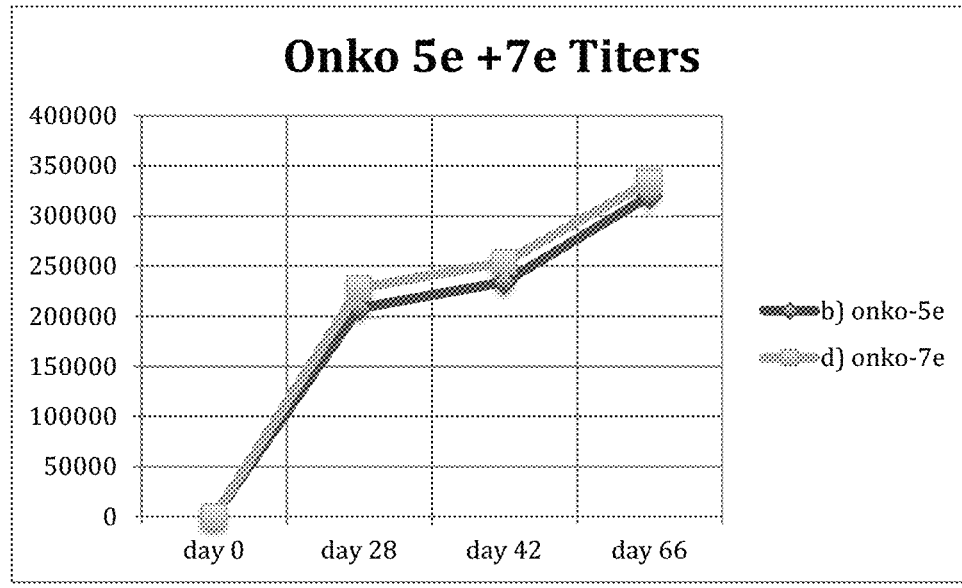

The results of this test are presented in FIG. 3A and FIG. 3B. There is can be seen that immunogens 1 and 2 (of Example 1, and 2) were effective in terms of inhibiting the growth of human lung cancer cells, using either of the anti-gastrin releasing peptide+/−human progastrin (Onko-5a; Onko-7a immunogens), as well as in inducing sufficient antibody responses that were effective in the presence of conventional lung cancer chemotherapies. At standard or low dosages.

Example 6

Figure 4A:
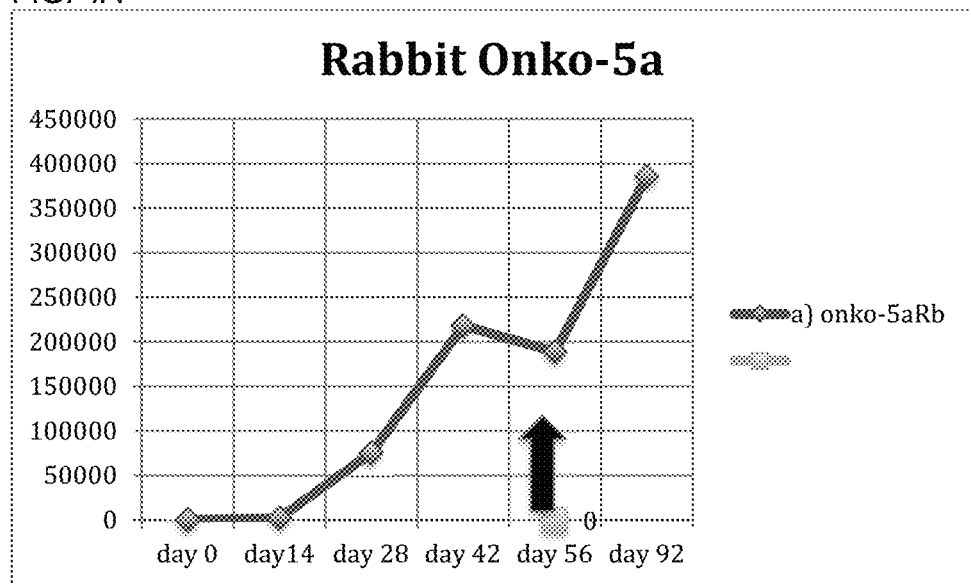
FIG. 4B)Onko-7a-TT; and after boost injections at day 56 and titers measured after 90 days.
Figure 4B:
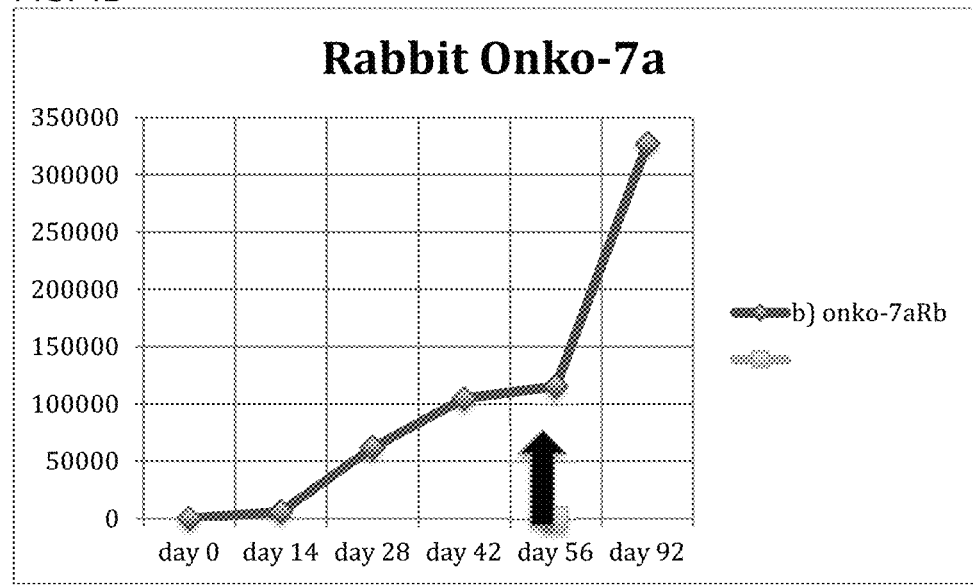
Figure 5:
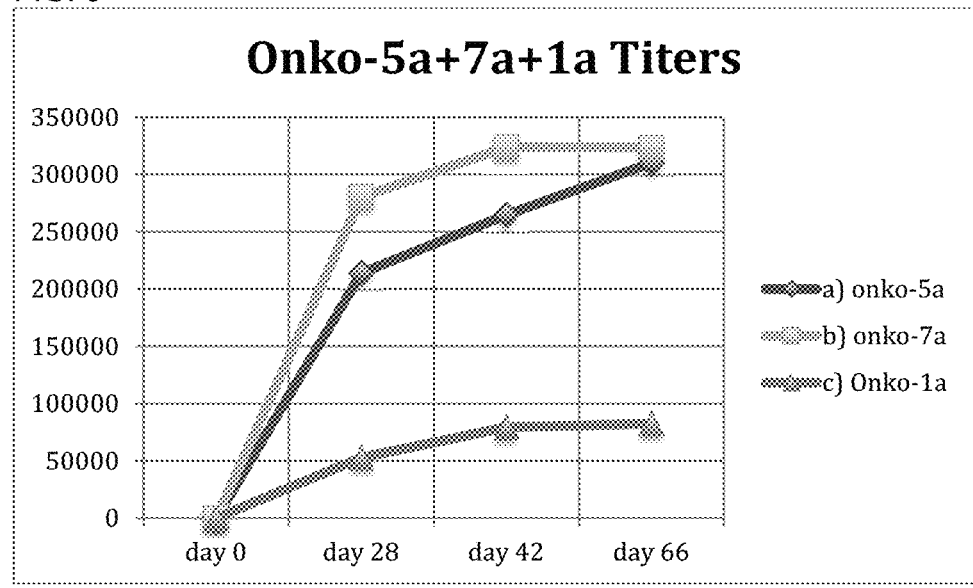
FIG. 5 depicts the antibody response in mice as measured by ELISA with three initial administrations of an immunogen conjugate constructed with three peptides 25ug each of Onko5a-TT+Onko-7a-TT+Onko1a-TT

The inventors constructed conjugates comprising each of the above-mentioned Onko-5a and analogs (Seq ID 1-8 and 41-46) and Onko-7a peptides (SEQ ID NO.: 9-17, respectively) and compared them to Onko-5a and Onko-7a (SEQ ID NO.: 1 and 9 respectively). They were all linked to TT, as described in Examples 1 and 2. The inventors then immunized six mice each with these immunogens (see FIG. 4A to FIG. 4B) and six mice with the Onko-5A immunogen, for similar comparisons.

The improvements thus demonstrated arise from modifications embodied in the immunomimics and the unique spacer regions of the immunogen peptides according to the invention. The inventive peptide immunogens were tested against immunogens that did not incorporate any of the above-described immunogenic mimics and spacers, and the latter were found less effective. Accordingly, the conventional immunogens were improved by the inventors' modifying their immunogens using the above described mimics, spacers and emulsification procedures incorporating ancillary immune stimulating substances as adjuvants, such as described below.

Items

1. A pharmaceutical immunogenic composition, comprising at least an oligopeptide comprising an amino acid sequence selected from the group consisting of SEQ ID NO 1 to SEQ ID NO 75, and/or comprising a variant amino acid sequence that is at least 90% identical to that of SEQ ID NO 1 to SEQ ID NO 75, and a pharmaceutically acceptable carrier, wherein the polypeptide immunogen comprises a mimetic peptide comprised of (i) the amino acid sequence of a progastrin releasing peptide and/or a N-terminal and/or C-terminal species of a progastrin-family peptide joined to (ii) sequence specified D-amino-acid peptide segment functioning as a spacer region and (iii) an immunogenic carrier coupled to said mimetic peptide.

2. The pharmaceutical immunogenic composition according to item 1, further comprising at least oligopeptides comprising of amino acid sequence selected from the group consisting of SEQ ID NO 1 to SEQ ID NO 75, and/or a mimetic peptide sequences corresponding to SEQ ID NO 1 to SEQ ID NO 75, and a pharmaceutically acceptable carrier. A preferred polypeptide immunogen according to item 1, wherein the amino acids and mimetic peptide residues consists of an equal mixture of the amino acid sequences:

```
(ONKO-5a)
                                    (SEQ ID NO.: 1)
CYS-pro-pro-pro-pro-SER-SER-GLN-PRO-LYS-ALA-LEU-
GLY-ASN-GLN-GLN-PRO-SER-TRP-ASP-SER-GLU-ASP-SER-
SER-ASN-PHE-LYS-ASP
and
                                    (SEQ ID NO.: 9)
Cys-pro-pro-pro-pro-SER-SER-TYR-PRO-ARG-GLY-ASN-
HIS-TRP-ALA-VAL-GLY-HIS-LEU-MET-NH₂.
```

3. The pharmaceutical immunogenic composition according to item 1, wherein said immunogen peptide comprises at least one or more oligopeptides having an overall length of from 8 to 100, optionally from 8 to 30 selected from: a peptide immunogen according to item 1, wherein said mimetic peptides comprises one or more oligopeptides as amino acid sequences that is selected from the group consisting of: SEQ ID No.: 1 to SEQ ID NO.: 75.

4. The pharmaceutical composition according to item 1, comprising at least one or more peptides consisting of D-amino acid sequences according to SEQ ID NO.:1 to SEQ ID NO.: 75.

5. The pharmaceutical immunogenic composition according to item 1, wherein at least the immunogen administered may include a defined mixture of immunogens. The preferred pharmaceutical immunogenic composition according to item 1, wherein at least the immunogen administered may include a defined mixture of one or more immunogens selected from oligopeptide sequences: SEQ ID NO.:1 to SEQ ID NO.:75.

6. The pharmaceutical composition according to item 1, wherein immunogenic peptide is conjugated to an immunogenic proteinaceous carrier component; a preferred pharmaceutical immunogenic substance(s), generally greater than 6000 Daltons in size, such as diphtheria toxoid (DT); tetanus toxoid (TT) pertussis toxoid (PT) or any of their commercially approved combinations (eg., TD, DPT, T-dap, BCG, etc.).

7. A method of inhibiting malignant growth by using an immunogen generating specific anti-growth stimulating factors of Lung, GI and other cancer cells in a mammal, comprising the step of generating patient immune cells to produce a growth-inhibitory amount of antibody(s) and immune activated T-cells, wherein said antibody(s) is/are stimulated in patients administered with said immunogens that:

(i) binds the family of gastrins and gastrin releasing peptides, or bombesin-like peptide specifically and its precursor peptides which are not cross-reactive with substance P;

(ii) has singly and/or in combination, specificity for a peptide having the amino acid sequences of carboxyl terminal heptapeptide region Trp-Ala-Val-Gly-His-Leu-Met (SEQ ID NO: 61) of bombesin; and/or for the type I II and III of progastrin releasing peptide (ProGRP) family peptides;

(iii) has singly and/or in combination, immunogens with specificity for other gastrin-family peptides having amino acid sequences sharing similarity and/or identity to carboxy-terminal hexapeptide region SER-ALA-GLU-ASP-GLU-ASN (SEQ ID NO: 62) of Progastrin family of peptides;

(iv) has in combination, immunogens with specificity for other gastrin-family peptides having amino acid sequences sharing similarity and/or identity to unprocessed precursors of the preprohormone prohormone or such members that are partially convertase processed belonging to the Progastrin family and the Progastrin Releasing Peptide family of peptides;

(v) has in combination, immunogens with specificity for other gastrin-family peptides having amino acid sequences sharing similarity and/or identity to the proconvertase processed precursors of the preprohormone Progastrin family and Progastrin Releasing Peptide family of peptides;

(vi) immunogens engender antibodies in mammals that blocks the binding of said Gastrin Family and Gastrin Releasing Peptide Family and their precursors to their receptor and/or said binding proteins present on small cell lung cancer cells (SCLC), neuroendocrine, non-small cancer lung (NSCLC) cancer cells and other cancers, such as the GI cancers, pulmonary cancers, reproductive cancers, brain and bone and urothelial cancers.

(vii) immunogens engender antibodies in mammals that blocks the binding of said gastrin and/or gastrin-family peptides and its precursors to receptor and/or said binding proteins present on small cell lung cancer cells (SCLC), neuroendocrine, non-small cancer lung (NSCLC) cancer cells and other cancers, such as the GI cancers, pulmonary cancers, reproductive cancers, brain and bone and urothelial cancers.

8. The immunogenic composition according to item 6, wherein said pharmaceutically acceptable carrier comprises an emulsion of an aqueous phase, in which said immunogen is present, and an oily phase.

9. The immunogenic composition according to item 6, wherein said oily phase comprises at least one of squalene, squalane, sorbitan monooleate, Polysorbate 40, Polysorbate 80, and one or more of the vitamin E family of tocopherols.

10. The immunogenic composition according to claim 6, wherein said oily phase comprises at least one or more emulsifier components.

11. The immunogenic composition according to item 6, comprises a pharmaceutical composition wherein either said oily phase and/or said aqueous phase contains at least one adjuvant.

12. The pharmaceutical composition according to item 11, further comprising at least one or more suitable adjuvant(s), designed to stimulate the innate and adaptive immune arms by selecting individually or in combination from the group consisting of: colony-stimulating factors, optionally comprising (R)-enantiomer of Biltricidc (Praziquantcl), imiquimod, resiquimod, STINGVax and/or Granulocyte Macrophage Colony Stimulating Factor (GM-CSF), 1018 ISS, aluminium salts, mixed tocopherols, cholecalciferol, Amplivax™, AS15, BCG, CP-870,893, CpG7909, CyaA, dSLIM, GM-CSF, IC30, IC31, Cyclic dinucleotides, such as cyclic diguanylate monophosphate (c-di-GMP) or other such innate immune agonists (e.g., Poly ICLC, GLA, MEDI9197, VTX2337, CpG(SD-101); Chitosan nanoparticles, ImuFact™ IMP321, IS Patch, ISCOMATRIX™, JuvImmune™, LipoVac™, MF59, monophosphoryl lipid A, Montanide™ IMS 1312, Montanide™ ISA 206, Montanide™ ISA 50V, Montanide™ ISA-51, OK-432, OM-174, OM-197-MP-EC, ONTAK®, PepTel® vector system, PLG microparticles, resiquimod, SRL172, Virosomes and other Virus-like particles, YF-17 DBCG, Aquila's QS21 stimulon, Ribi's Detox. Quil, Superfos, cholera toxin, and/or immunological adjuvants, MF59, and cytokines, as well as anti-check point antibody inhibitors (e.g., anti-PD-1L, anti-PD-L2, anti-PD-1, anti-CTLA-4) singly or in combination; The preferred immunogenic composition according to claim 1, wherein said adjuvant(s) is/are selected from the group consisting of Ergamisol, cyclic diguanylate Chitosan, Praziquantel, uric acid, mannan and derivatives of mannan, and vitamin D3, Nor-MDP, imiquimod, cyclic diguanylate, threonyl- N-acetyl-muramyl-L-alanyl-D-isoglutamine, Isoprinosine, trehalose dimycolate, QS-21, alpha-galactosylceramide, and alpha-glucosylceramide.

13. The pharmaceutical composition according to item 1, wherein said immunogen(s) is/are used with non-immunosuppressive chemotherapeutics that are selected from the group consisting of (but not limited to): cyclophosphamides, anthracyclins; doxorubicin, platinums; cisplatins, thalidomides; revlimid, fluropyrimidines; pemetrexed etc. (i.e., capable of inducing immune cell death in malignant cells, L. Galluzzi et., al., *Nature Reviews Immunology* 17, pp. 97-111 (2017)).

14. The pharmaceutical composition according to claim 1, wherein said composition comprises a nano-sized (i.e., less than 1 micron) emulsified immunogen that is capable of being administered intramuscularly, intradermally, intratumorally, orally, dermally, nasally, buccally, rectally, intravenously, intra-arterially, intra-peritoneally, vaginally, by inhalation, and/or by topical administration.

15. A method for treating and/or preventing a cancer in a patient comprising administering to the patient a therapeutically effective amount of said nano-emulsified immunogenic pharmaceutical composition of item 1, either alone or in combination with standard of care chemotherapeutic agents and/or radiation therapeutics at full strength or metronomically at lower dosages;

16. The method according to item 15, wherein said nano-emulsified immunogenic pharmaceutical composition can be used as an anti-cancer vaccine treatment designed to reduce initial and/or recurrent malignant disease.

17. The method of item 16, wherein the cancer is preferably, small cell lung cancer (SCLC), non-small-cell lung cancer (NSCLC), bronchogenic large-cell lung carcinoma (LCLC), squamous cell carcinomas or carcinomatous, gastric cancers, prostate cancer, colon cancer, pancreatic cancers, pancreato-biliary ductal adenocarcinoma, breast, ovarian cancer, urothelial, brain, bone or hepatocellular carcinoma, or malignant solid tumors of the GI tract, lung, reproductive organs and/or metastasis thereof.

18. The method according to item 17, wherein said cancers are of pulmonary or gastro-intestinal origin disseminated into lung, liver or peritoneum.

19. The method according to item 17, wherein said cancers are of pulmonary, reproductive or urothelial origin disseminated into brain, bone or mesothelium.

20. The pharmaceutical composition according to item 1, wherein said immunogen is used with non-immunosuppressive and/or targeted chemotherapeutics that are selected from the group consisting of (but not limited to): kinase inhibitors, receptor tyrosine kinase inhibitors, cyclophosphamides, anthracyclins;doxorubicin, folate inhibitors, taxols, abraxane, platinums; oxaliplatin, cisplatins, thalidomides; revlimid, fluropyrimidines; oral fluoropyridimines pemetrexed etc. (i.e., those FDA approved chemotherapies capable of inducing immune cell death in malignant cells);complementary FDA approved monoclonal antibodies that do not interfere with immunogen induced antibody titers.

21. The pharmaceutical composition according to item 1, wherein said composition comprises a vaccine-like agent or immunogen that is emulsified with particulates (alum adjuvants, calcium polyphosphates, nanoparticulated chitosan) suspensions, capable of being administered intramuscularly, intradermally, intratumorally, orally, dermally, nasally, buccally, rectally, intravenously, intra-arterially, intra-peritoneally, vaginally, by inhalation, and/or by topical administration.

22. A method for treating and/or preventing a cancer in a patient comprising administering to the patient a therapeutically effective amount of said immunogenic pharmaceutical composition of item 21, either alone or in combination with standard of care FDA approved chemotherapeutic agents and/or combined with radiation therapeutics.

23. The method according to item 21, wherein said immunogenic pharmaceutical composition can be an anti-cancer therapeutic or prophylactic vaccine treatment.

24. The method of item 21, wherein the cancer is preferably, small cell lung cancer (SCLC), non-small-cell lung cancer (NSCLC), bronchogenic large-cell lung carcinoma (LCLC), squamous cell carcinomas or carcinomatous, gastric cancers, prostate cancer, colon cancer, pancreatic cancers, pancreato-biliary ductal adenocarcinoma, ovarian cancer, hepatocellular carcinoma, brain, bone, urothelial and/or malignant solid tumors of the lung and/or metastasis of the stated cancers thereof.

25. The method according to item 16, wherein said cancers are of haematogenous or lymphatic malignancies; in conjunction with FDA standard of care chemotherapeutics at standard or metronomic lower dosages or FDA approved targeted therapeutics.

The invention claimed is:

1. A pharmaceutical immunogenic composition comprising a pharmaceutically acceptable carrier and an effective amount of at least one immunogenic oligopeptide of a progastrin releasing peptide, wherein the oligopeptide comprises an amino acid sequence selected from the group consisting of SEQ ID NO: 1, SEQ ID NO: 9, SEQ ID NO: 28, SEQ ID NO: 36, SEQ ID NO: 40 and SEQ ID NO: 51, wherein the at least one immunogenic oligopeptide is linked to a D-amino acid peptide spacer sequence and conjugated to an immunogenic carrier.

2. The pharmaceutical immunogenic composition of claim 1, wherein the at least one immunogenic oligopeptide consists of an equal mixture of the amino acid sequences of SEQ ID NO: 1 and SEQ ID NO: 9.

3. The pharmaceutical immunogenic composition of claim 1, wherein the immunogenic carrier is an immunogenic proteinaceous carrier greater than 6000 Daltons in size.

4. The pharmaceutical immunogenic composition of claim 1, wherein the pharmaceutically acceptable carrier comprises an emulsion of an aqueous phase and an oily phase, wherein the at least one immunogenic oligopeptide is present in the aqueous phase.

5. The pharmaceutical immunogenic composition of claim 4, wherein the oily phase comprises at least one of squalene, squalene, sorbitan monooleate, Polysorbate 40, Polysorbate 80, and one or more of the vitamin E family of tocopherols.

6. The pharmaceutical immunogenic composition of claim 4, wherein said oily phase and/or said aqueous phase contains at least one adjuvant.

7. The pharmaceutical immunogenic composition of claim 5, further comprising one or more suitable adjuvants.

8. The pharmaceutical immunogenic composition of claim 1, wherein the composition comprises cyclophosphamides, anthracyclins, doxorubicin, platinums, cisplatins, thalidomides, revlimid, fluropyrimidines and pemetrexed.

9. The pharmaceutical immunogenic composition of claim 1, wherein the composition comprises a nano-sized emulsified immunogen that is capable of being administered intramuscularly, intradermally, intratumorally, orally, dermally, nasally, buccally, rectally, intravenously, intra-arterially, intra-peritoneally, vaginally, by inhalation, or by topical administration.

10. The pharmaceutical immunogenic composition of claim 3, wherein the immunogenic proteinaceous carrier is diphtheria toxoid (DT), tetanus toxoid (TT), pertussis toxoid (PT), or any combination thereof.

11. A method of inhibiting the growth of cancer cells in a patient comprising administering to the patient a growth-inhibitory amount of the pharmaceutical immunogenic composition of claim 9 either alone or in combination with standard care chemotherapeutic agents and/or radiation therapeutics at full strength or metronomically at lower dosages.

12. The method of claim 11, wherein the cancer is small cell lung cancer (SCLC), non-small cell lung cancer (NSCLC), bronchogenic large-cell lung carcinoma (LCLC), gastric cancer, prostate cancer, colon cancer, pancreatic cancer, pancreato-biliary ductal adenocarcinoma, breast cancer, ovarian cancer, urothelial cancer, hepatocellular carcinoma, or malignant solid tumor of the GI tract, lung, reproductive organs and/or metastasis thereof.

13. The method of claim 11, wherein the method comprises administering the patient with cisplatin, 5-fluorouracil, or a combination thereof.

* * * * *